US008969366B2

(12) United States Patent
Marchionni et al.

(10) Patent No.: US 8,969,366 B2
(45) Date of Patent: Mar. 3, 2015

(54) SUBSTITUTED PYRIMIDINYLPYRROLOPYRIDINONE DERIVATIVES, PROCESS FOR THEIR PREPARATION AND THEIR USE AS KINASE INHIBITORS

(71) Applicants: Chiara Marchionni, Milan (IT); Fabio Zuccotto, Milan (IT); Alessandra Badari, Vedano al Lambro (IT); Mauro Angiolini, Gavirate (IT); Davide Carenzi, Travedona Monate (IT); Marina Caldarelli, Milan (IT); Maurizio Pulici, Caponago (IT)

(72) Inventors: Chiara Marchionni, Milan (IT); Fabio Zuccotto, Milan (IT); Alessandra Badari, Vedano al Lambro (IT); Mauro Angiolini, Gavirate (IT); Davide Carenzi, Travedona Monate (IT); Marina Caldarelli, Milan (IT); Maurizio Pulici, Caponago (IT)

(73) Assignee: Nerviano Medical Sciences S.R.L., Nerviano (MI) (IT)

(*) Notice: Subject to any disclaimer, the term of this patent is extended or adjusted under 35 U.S.C. 154(b) by 0 days.

(21) Appl. No.: 14/010,734

(22) Filed: Aug. 27, 2013

(65) Prior Publication Data

US 2013/0345245 A1 Dec. 26, 2013

Related U.S. Application Data

(62) Division of application No. 13/377,854, filed as application No. PCT/EP2010/058223 on Jun. 11, 2010, now Pat. No. 8,546,413.

(30) Foreign Application Priority Data

Jun. 15, 2009 (EP) .................................. 09162719

(51) Int. Cl.
| *A01N 43/54* | (2006.01) |
| *A61K 31/505* | (2006.01) |
| *C07D 471/04* | (2006.01) |
| *A61K 31/506* | (2006.01) |
| *A61K 45/06* | (2006.01) |
| *A61N 5/00* | (2006.01) |

(52) U.S. Cl.
CPC ............ *C07D 471/04* (2013.01); *A61K 31/506* (2013.01); *A61K 45/06* (2013.01); *A61N 5/00* (2013.01)
USPC ............................ 514/275; 544/242; 544/331

(58) Field of Classification Search
USPC .................................................. 544/242, 331
See application file for complete search history.

(56) References Cited

U.S. PATENT DOCUMENTS

2012/0178770 A1 7/2012 Marchionni et al.

FOREIGN PATENT DOCUMENTS

| JP | 2007501827 A | 2/2007 |
| JP | 2009519919 A | 5/2009 |
| WO | WO 2005/014572 | 2/2005 |
| WO | WO 2007068728 A2 * | 6/2007 |
| WO | WO 2007071621 A1 | 6/2007 |

OTHER PUBLICATIONS

A.M. Traynor et al., Drugs of Today, 40(8), 697-710, 698 (2004).*
F.F. De Arruda, et al., Int. J. Radiation Oncology Biol. Phys., 64(2), 363-373 (2006).*
B.C. Bastian, Genetic Progression, in From Melanocytes to Melanoma the Progression to Malignancy 197, 201 (V. J. Hearing et al., eds., 2006).*
J. Tsai et al., 105 PNAS 3041-3046, 3041 (2008).*
S.K. Libutti, Colon Cancer in, 1 Cancer Principles & Practice of Oncology 1232, 1243 (V.T. DeVita, Jr. et al. eds., 8th ed., 2008).*
T. Carling et al., Thyroid Tumors in, 2 Cancer Principles & Practice of Oncology 1503 (V.T. DeVita, Jr. et al. eds., 8th ed., 2008).*
J. L. Raizer, Journal of Neuro-Oncology, 74(1), 77-86 (2005).*
R.G.W. Verhaak et al., Cancer Cell, 17(1), 1-24 (2010).*
L. Pusztai, Histopathologic and Molecular Markers of Prognosis and Response to Therapy, in Breast Cancer 324, 326-328 (Kelly k. Hunt et al., ed., 2nd ed., 2008).*
A. Kamb, Nature Reviews Drug Discovery 2, 161-165 (2005).*
F. Smith, Molecular Cancer Therapeutics, 6, 428-440, 428 (2007).*
N.E. Sharpless et al., Nature Reviews Drug Discovery 5, 741-754, 742 (2006).*
C. Abad-Zapatero, Drug Discovery Today, 1-8 (2010).*
K.P. Olive et al., Clinical Cancer Research 12, 5277-5287 (2006).*
Y. Song et al., Cancer a Conceptual Framework in, 1 Cancer Principles & Practice of Oncology 1, 5-6 (V.T. DeVita, Jr. et al. eds., 8th ed., 2008).*
B. Hann et al., Current Opinion in Cell Biology, 13, 778-784 (2001).*
A-M Bleau et al., 8 Cell Cycle 2937-2945 (2009).*
T. Leung et al., Liver International, 1315-1323 (2010).*
S. H. Lee et al., 22 Oncogene, 6942-6945 (2003).*
F. Selcukbircik et al., 18 JBUON, 116-123 (2012).*
N. Ishimura et al., 199 Cancer Letters, 169-173 (2008).*
H. Davles et al., 417 Nature 949-954 (2002).*
D. Bell, 18 Modern Pathology, 519-532 (2005).*
Cohen Y. et al., "BRAF Mutation in Papillary Thyroid Carcinoma", Journal of the National Cancer Institute 95 (8):625-627 (Apr. 16, 2003).
Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).

(Continued)

*Primary Examiner* — Alexander R Pagano
(74) *Attorney, Agent, or Firm* — Scully, Scott, Murphy & Presser, P.C.

(57) ABSTRACT

Pyrimidinylpyrrolopyridinone derivatives of formula (I) as defined in the specification, and pharmaceutically acceptable salts thereof, process for their preparation and pharmaceutical compositions comprising them are disclosed; the compounds of the invention may be useful, in therapy, in the treatment of diseases associated with a disregulated protein kinase activity, like cancer.

5 Claims, No Drawings

(56) References Cited

OTHER PUBLICATIONS

Davies H. et al., "Mutations of the BRAF Gene in Human Cancer", Nature 417:949-954 (Jun. 27, 2002).
Hagemann C. et al., "Isotype-Specific Functions of Raf Kinases", Experimental Cell Research 253:34-46 (1999).
Hingorani S.R. et al., "Suppression of BRAFV599E in Human Melanoma Abrogates Transformation", Cancer Research 63:5198-5202 (Sep. 1, 2003).
Hoshino R. et al., "Constitutive Activation of the 41-/43-kDa Mitogen-Activated Protein Kinase Signaling Pathway in Human Tumors", Oncogene 18:813-822 (1999).
Kolch W. et al., "The Role of Raf Kinases in Malignant Transformation", Expert Reviews in Molecular Medicine 18 pages (Apr. 25, 2002).
Mercer K.E. et al., "Raf Proteins and Cancer: B-Raf is Identified as a Mutational Target", Biochimica et Biophysica Acta 1653:25-40 (2003).
Peyssonnaux C. et al., "The Raf/MEK/ERK Pathway: New Concepts of Activation", Biology of the Cell 93:53-62 (2001).
Tannapfel A. et al., "Mutations of the BRAF Gene in Cholangiocarcinoma But Not in Hepatocellular Carcinoma", Gut 52 (5):706-712 (2003).
Vanotti E. et al., "Cdc7 Kinase Inhibitors: Pyrrolopyridinones as Potential Antitumor Agents. 1. Synthesis and Structure-Activity Relationships", J. Med. Chem. 51:487-501 (2008).
Wellbrock C. et al., "V599EB-RAF is an Oncogene in Melanocytes", Cancer Research 64:2338-2342 (Apr. 1, 2004).
Wojnowski L. et al., "Endothelial Apoptosis in Braf-Deficient Mice", Nature Genetics 16:293-297 (Jul. 1997).
International Search Report dated Jul. 30, 2010 received from the European Patent Office in related International Application No. PCT/EP2010/058223 from related U.S. Appl. No. 13/377,854.
International Search Report dated Jul. 30, 2010 received from related Application No. PCT/EP2010/058223.

* cited by examiner

SUBSTITUTED PYRIMIDINYLPYRROLOPYRIDINONE DERIVATIVES, PROCESS FOR THEIR PREPARATION AND THEIR USE AS KINASE INHIBITORS

CROSS REFERENCE TO RELATED APPLICATIONS

The present application is a divisional of co-pending application having U.S. Ser. No. 13/377,854, filed on Mar. 12, 2012, which is a 371 of International application having Serial No. PCT/EP2010/058223, filed on Jun. 11, 2010, which claims priority of European Patent Application No. 09162719.0, filed on Jun. 15, 2009, the contents of all of which are incorporated herein by reference.

The present invention relates to certain substituted pyrimidinylpyrrolopyridinone compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The classical Ras, Raf, MEK (mitogen activated protein kinase/extracellular signal-regulated kinase kinase), ERK (extracellular signal-regulated kinase) pathway plays a central role in the regulation of a variety of cellular functions dependent upon cellular context, including cellular proliferation, differentiation, survival, immortalization and angiogenesis (reviewed in Peyssonnaux and Eychene, Biology of the Cell, 2001, 93, 3-62). In this pathway, Raf family members are recruited to the plasma membrane upon binding to guanosine triphosphate (GTP) loaded Ras resulting in the phosphorylation and activation of Raf proteins. Activated Rafs then phosphorylate and activate MEKs, which in turn phosphorylate and activate ERKs. Upon activation, ERKs translocate from the cytoplasm to the nucleus resulting in the phosphorylation and regulation of activity of transcription factors such as Elk-I and Myc. The Ras/Raf/MEK/ERK pathway has been reported to contribute to the tumorigenic phenotype by inducing immortalisation, growth factor-independent growth, insensitivity to growth-inhibitory signals, ability to invade and metastasize, by stimulating angiogenesis and by inhibiting apoptosis (reviewed in Kolch et al., Exp. Rev. Mol. Med., 2002, 25 April, http://www.expertreviews.org/02004386h.htm). In fact, ERK phosphorylation is enhanced in approximately 30% of all human tumours (Hoshino et al., Oncogene, 1999, 18, 813-822). This may be a result of over-expression and/or mutation of key members of the pathway.

Three Raf serine/threonine protein kinase isoforms have been reported Raf-1/c-Raf, B-Raf and A-Raf (reviewed in Mercer and Pritchard, Biochim. Biophys. Acta, 2003, 1653, 25-40), the genes for which are thought to have arisen from gene duplication. All three Raf genes are expressed in most tissues but with differences: c-Raf is expressed ubiquitously at high levels, whereas B-Raf high-level expression is found in neuronal tissue and A-Raf in urogenital tissue. The highly homologous Raf family members have overlapping but distinct biochemical activities and biological functions (Hagemann and Rapp, Expt. Cell Res. 1999, 253, 34-46). Expression of all three Raf genes is required for normal murine development however both c-Raf and B-Raf are required to complete gestation. B-Raf −/− mice die at E12.5 due to vascular hemorrhaging caused by increased apoptosis of endothelial cells (Wojnowski et al, Nature Genet., 1997, 16, 293-297). B-Raf is reportedly the major isoform involved in cell proliferation and the primary target of oncogenic Ras. Activating 5 somatic missense mutations have been identified exclusively for B-Raf, occurring with a frequency of 66% in malignant cutaneous melanomas (Davies et al., Nature, 2002, 417, 949-954) and also present in a wide range of human cancers, including but not limited to papillary thyroid tumours (Cohen et al., J. Natl. Cancer Inst., 2003, 95, 625-627), cholangiocarcinomas (Tannapfel et al., Gut, 2003, 52, 706-712), colon and ovarian cancers (Davies et al., Nature, 10 2002, 417, 949-954). The most frequent mutation in B-Raf (80%) is a glutamic acid for valine substitution at position 600. These mutations increase the basal kinase activity of B-Raf and are thought to uncouple Raf/MEK/ERK signalling from upstream proliferation drives including Ras and growth factor receptor activation resulting in constitutive activation of ERK. Mutated B-Raf proteins are transforming in NIH3T3 cells (Davies et al., Nature, 2002, 15 417, 949-954) and melanocytes (Wellbrock et al., Cancer Res., 2004, 64, 2338-2342) and have also been shown to be essential for melanoma cell viability and transformation (Hingorani et al., Cancer Res., 2003, 63, 5198-5202). As a key driver of the Raf/MEK/ERK signalling cascade, B-Raf represents a likely point of intervention in tumours dependent on this pathway Pyrrolopyridinones derivatives for the treatment of hyperproliferative diseases such as cancer have been disclosed in WO 2007/068728 and in WO 2007/071621 in the name of Pfizer Italia Srl.

Despite these developments, there is still need for effective agents for said disease.

The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted pyrimidinylpyrrolopyridinone compound represented by formula (I),

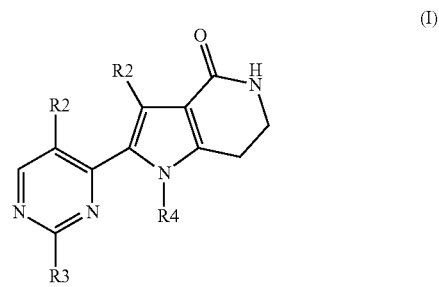

wherein:
R1 is hydrogen or R1', wherein R1 is

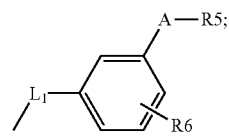

R2 is hydrogen or R2', wherein R2' is

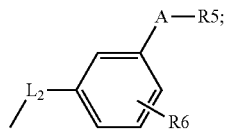

R3 is NH2 or R3', wherein R3' is L$_3$-R5,
wherein
L$_1$ is direct bond, CH$_2$, CH=CH, O, NH or N(CH$_3$);
L$_2$ is CH$_2$CH$_2$, CH=CH or C≡C;
L$_3$ is NHCO, NHCH$_2$, NHCONH, CH=CH or C≡C;
A is direct bond, O, OCH2, OCO, CON(Y), CON(Y)O, CON(Y)N(Y), CON(Y)SO$_2$, N(Y), N(Y)CO, N(Y)SO$_2$—, N(Y)CON(Y), N(Y)CSN(Y), N(Y)CON(Y)N(Y), N(Y)COO, N(Y)CON(Y)SO$_2$ or N(Y)SO$_2$N(Y);
Y is hydrogen or an optionally substituted straight or branched (C$_1$-C$_3$) alkyl;
R5 is hydrogen or an optionally substituted group selected from straight or branched (C$_1$-C$_8$) alkyl, (C$_2$-C$_8$) alkenyl, (C$_2$-C$_8$) alkynyl, (C$_3$-C$_8$) cycloalkyl, heterocyclyl, aryl and heteroaryl;
R6 is selected from hydrogen, halogen, trifluoromethyl, (C$_1$-C$_3$) alkyl and (C$_1$-C$_3$) alkoxy;
R4 is an optionally substituted group selected from straight or branched C$_1$-C$_6$ alkyl, C$_2$-C$_6$ alkenyl, C$_2$-C$_6$ alkynyl, C$_3$-C$_6$ cycloalkyl and heterocyclyl;
with the proviso that
only one of R1, R2 and R3 is respectively R1', R2' or R3' as defined above, and
and pharmaceutically acceptable salts.

The present invention also provides methods of preparing the substituted pyrimidinylpyrrolopyridinone compounds, represented by formula (I), prepared through a process consisting of standard synthetic transformations.

The present invention also provides a method for treating diseases caused by and/or associated with dysregulated protein kinase activity, particularly RAF family, protein kinase C in different isoforms, RET, Met, PAK-4, PAK-5, ZC-1, STLK-2, DDR-2, Aurora A, Aurora B, Aurora C, Bub-1, Chk1, Chk2, HER2, MEK1, MAPK, EGF-R, PDGF-R, FGF-R, IGF-R, PI3K, weel kinase, Src, Abl, Akt, MAPK, ILK, MK-2, IKK-2, Cdc7, Nek, Cdk/cyclin kinase family, including PLK-1 and PLK-3, which comprises administering to a mammal, in need thereof, an effective amount of a substituted pyrimidinylpyrrolopyridinone compound represented by formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

In a further preferred embodiment, the method of the present invention further comprises subjecting the mammal in need thereof to a radiation therapy or chemotherapy regimen in combination with at least one cytostatic or cytotoxic agent.

Moreover the invention provides an in vitro method for inhibiting the RAF family protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

With the term "straight or branched $C_1$-$C_8$ alkyl", we intend any of the groups such as, for instance, methyl, ethyl, n-propyl, isopropyl, n-butyl, isobutyl, tert-butyl, sec-butyl, n-pentyl, n-hexyl, n-heptyl, n-octyl and the like.

With the term "straight or branched $C_1$-$C_8$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_1$-$C_3$ alkyl", we intend any of the groups such as, for instance, methyl, ethyl, n-propyl, isopropyl.

With the term "$C_3$-$C_8$ cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_2$-$C_8$ alkenyl" we intend an aliphatic $C_2$-$C_8$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$C_2$-$C_8$ alkynyl" we intend an aliphatic $C_2$-$C_8$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above R1, R2, R3, R4, R5, R6 and Y group may be optionally substituted, in any of their free positions, by one or more groups, for instance 1 to 6 groups, independently selected from: halogen, nitro, oxo groups (=O), cyano, $C_1$-$C_8$ alkyl, polyfluorinated alkyl, polyfluorinated alkoxy, $C_2$-$C_8$ alkenyl, $C_2$-$C_8$ alkynyl, hydroxyalkyl, aryl, arylalkyl, heteroaryl, heteroarylalkyl, heterocyclyl, heterocyclylalkyl, $C_3$-$C_8$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term halogen atom we intend a fluorine, chlorine, bromine or iodine atom.

With the term polyfluorinated alkyl or polyfluorinated alkoxy we intend any of the above straight or branched $C_1$-$C_8$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_8$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_8$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:
R1 is R1', wherein:
$L_1$ is direct bond or $CH_2$;
A is N(Y)CON(Y), wherein Y is hydrogen;
R5 is an optionally substituted group selected from heterocyclyl, aryl and heteroaryl and
R6 is as defined above;
R2 is hydrogen;
R3 is $NH_2$ and
R4 is as defined above.

Another preferred class of compounds of formula (I) are the compounds wherein:
R1 is R1', wherein:
$L_1$ is direct bond or $CH_2$;
A is —O—;
R5 is hydrogen and
R6 is as defined above;
R2 is hydrogen;
R3 is $NH_2$ and
R4 is as defined above.

A further preferred class of compounds of formula (I) are the compounds wherein:
R1 is hydrogen;
R2 is R2', wherein:
$L_2$ is C≡C;
A is —N(Y)CON(Y)—, wherein Y is hydrogen;
R5 is an optionally substituted group selected from heterocyclyl, aryl and heteroaryl and
R6 is as defined above;
R3 is $NH_2$ and
R4 is as defined above.

Another further preferred class of compounds of formula (I) are the compounds wherein:
R1 is hydrogen;
R2 is R2', wherein:
$L_2$ is C≡C;
A is —O—;
R5 is hydrogen and
R6 is as defined above;
R3 is $NH_2$ and
R4 is as defined above.

Another further preferred class of compounds of formula (I) are the compounds wherein:
R1 and R2 are hydrogen;
R3 is R3', wherein:
$L_3$ is NHCO, NHCH—, CH═CH or C≡C and
R4 and R5 are as defined above.

Preferred specific compounds of formula (I) are the compounds listed below:
1) 1-{3-[2-(2-Amino-pyrimidin-4-yl)-1-methyl-4-oxo-4,5,6,7-tetrahydro-1H-pyrrolo[3,2-c]pyridin-3-yl]-phenyl}-3-(4-trifluoromethyl-phenyl)-urea;
2) 2-[2-Amino-5-(3-hydroxy-phenylethynyl)-pyrimidin-4-yl]-1-methyl-1,5,6,7-tetrahydro-pyrrolo[3,2-c]pyridin-4-one;
3) 2-[2-Amino-5-(3-hydroxy-phenylethynyl)-pyrimidin-4-yl]-1-(2-fluoro-ethyl)-1,5,6,7-tetrahydro-pyrrolo[3,2-c]pyridin-4-one;
4) 4-Bromo-thiophene-2-carboxylic acid [4-(1-methyl-4-oxo-4,5,6,7-tetrahydro-1H-pyrrolo[3,2-c]pyridin-2-yl)-pyrimidin-2-yl]-amide;
5) Thiophene-2-carboxylic acid {4-[1-(2-fluoro-ethyl)-4-oxo-4,5,6,7-tetrahydro-1H-pyrrolo[3,2-c]pyridin-2-yl]-pyrimidin-2-yl}-amide;
6) 2-[2-(3-Chloro-benzylamino)-pyrimidin-4-yl]-1-methyl-1,5,6,7-tetrahydro-pyrrolo[3,2-c]pyridin-4-one hydrochloride;
7) 2-{2-[(4-Bromo-thiophen-2-ylmethyl)-amino]-pyrimidin-4-yl}-1-methyl-1,5,6,7-tetrahydro-pyrrolo[3,2-c]pyridin-4-one hydrochloride;
8) 2-[2-(3-Chloro-phenylethynyl)-pyrimidin-4-yl]-1-methyl-1,5,6,7-tetrahydro-pyrrolo[3,2-c]pyridin-4-one;
9) 2-{2-[(E)-2-(3-Chloro-phenyl)-vinyl]-pyrimidin-4-yl}-1-methyl-1,5,6,7-tetrahydro-pyrrolo[3,2-c]pyridin-4-one;
10) 3-Chloro-N-[4-(1-methyl-4-oxo-4,5,6,7-tetrahydro-1H-pyrrolo[3,2-c]pyridin-2-yl)-pyrimidin-2-yl]-benzamide;
11) Thiophene-2-carboxylic acid [4-(1-methyl-4-oxo-4,5,6,7-tetrahydro-1H-pyrrolo[3,2-c]pyridin-2-yl)-pyrimidin-2-yl]-amide;
12) Thiophene-3-carboxylic acid [4-(1-methyl-4-oxo-4,5,6,7-tetrahydro-1H-pyrrolo-[3,2-c]pyridin-2-yl)-pyrimidin-2-yl]-amide;
13) Furan-2-carboxylic acid {4-[1-(2-fluoro-ethyl)-4-oxo-4,5,6,7-tetrahydro-1H-pyrrolo[3,2-c]pyridin-2-yl]-pyrimidin-2-yl}-amide;
14) 4-Methyl-thiophene-2-carboxylic acid [4-(1-methyl-4-oxo-4,5,6,7-tetrahydro-1H-pyrrolo[3,2-c]pyridin-2-yl)-pyrimidin-2-yl]-amide;
15) 2-(2-Amino-pyrimidin-4-yl)-3-(4-chloro-3-hydroxy-phenyl)-1-methyl-1,5,6,7-tetrahydro-pyrrolo[3,2-c]pyridin-4-one;
16) 2-(2-Amino-pyrimidin-4-yl)-3-(4-fluoro-3-hydroxy-phenyl)-1-methyl-1,5,6,7-tetrahydro-pyrrolo[3,2-c]pyridin-4-one;
17) 2-(2-Amino-pyrimidin-4-yl)-3-(3-fluoro-5-hydroxy-phenyl)-1-methyl-1,5,6,7-tetrahydro-pyrrolo[3,2-c]pyridin-4-one;
18) 2-(2-Amino-pyrimidin-4-yl)-3-(3-chloro-5-hydroxy-phenyl)-1-methyl-1,5,6,7-tetrahydro-pyrrolo[3,2-c]pyridin-4-one;
19) 2-(2-Amino-pyrimidin-4-yl)-3-(3-hydroxy-benzyl)-1-methyl-1,5,6,7-tetrahydro-pyrrolo[3,2-c]pyridin-4-one;
20) 2-(2-Amino-pyrimidin-4-yl)-3-(4-chloro-3-hydroxy-benzyl)-1-methyl-1,5,6,7-tetrahydro-pyrrolo[3,2-c]pyridin-4-one;
21) 2-(2-Amino-pyrimidin-4-yl)-3-(3-chloro-5-hydroxy-benzyl)-1-methyl-1,5,6,7-tetrahydro-pyrrolo[3,2-c]pyridin-4-one;

22) 2-[2-Amino-5-(4-fluoro-3-hydroxy-phenylethynyl)-pyrimidin-4-yl]-1-methyl-1,5,6,7-tetrahydro-pyrrolo[3,2-c]pyridin-4-one;
23) 2-[2-Amino-5-(3-fluoro-5-hydroxy-phenylethynyl)-pyrimidin-4-yl]-1-methyl-1,5,6,7-tetrahydro-pyrrolo[3,2-c]pyridin-4-one;
24) 2-[2-Amino-5-(3-chloro-5-hydroxy-phenylethynyl)-pyrimidin-4-yl]-1-methyl-1,5,6,7-tetrahydro-pyrrolo[3,2-c]pyridin-4-one, and
25) 2-[2-Amino-5-(4-chloro-3-hydroxy-phenylethynyl)-pyrimidin-4-yl]-1-methyl-1,5,6,7-tetrahydro-pyrrolo[3,2-c]pyridin-4-one.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The reported Scheme 1 shows the preparation of a compound of formula (I).

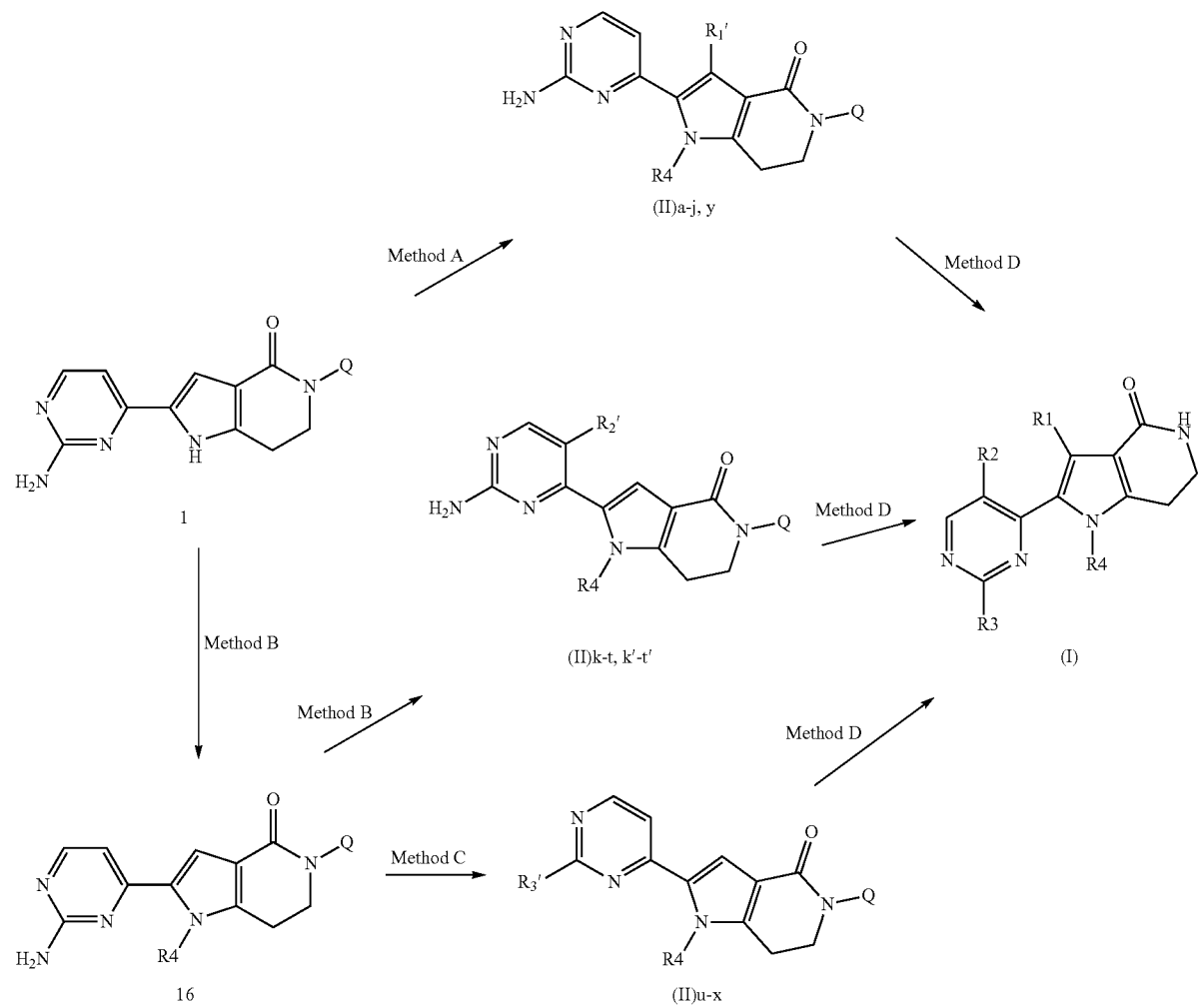

In the above scheme, Q is a suitable protecting amino group such as t-butoxycarbonyl and R1, R2, R3, R4, R1', R2' and R3' are as defined above.

All those with ordinary skills in the art will appreciate that any transformation performed according to said methods may require standard modifications such as, for instance, protection of interfering groups, change to other suitable reagents known in the art, or make routine modifications of reaction conditions.

The intermediate compound of formula (II)a-j,y is prepared according to Method A reported below.

The intermediate compound of formula (II)k-t, k'-t' is prepared according to method B reported below.

The intermediate compound of formula (II)u-x is prepared according to method C reported below.

The compound of formula (I) is prepared according to Method D reported below.

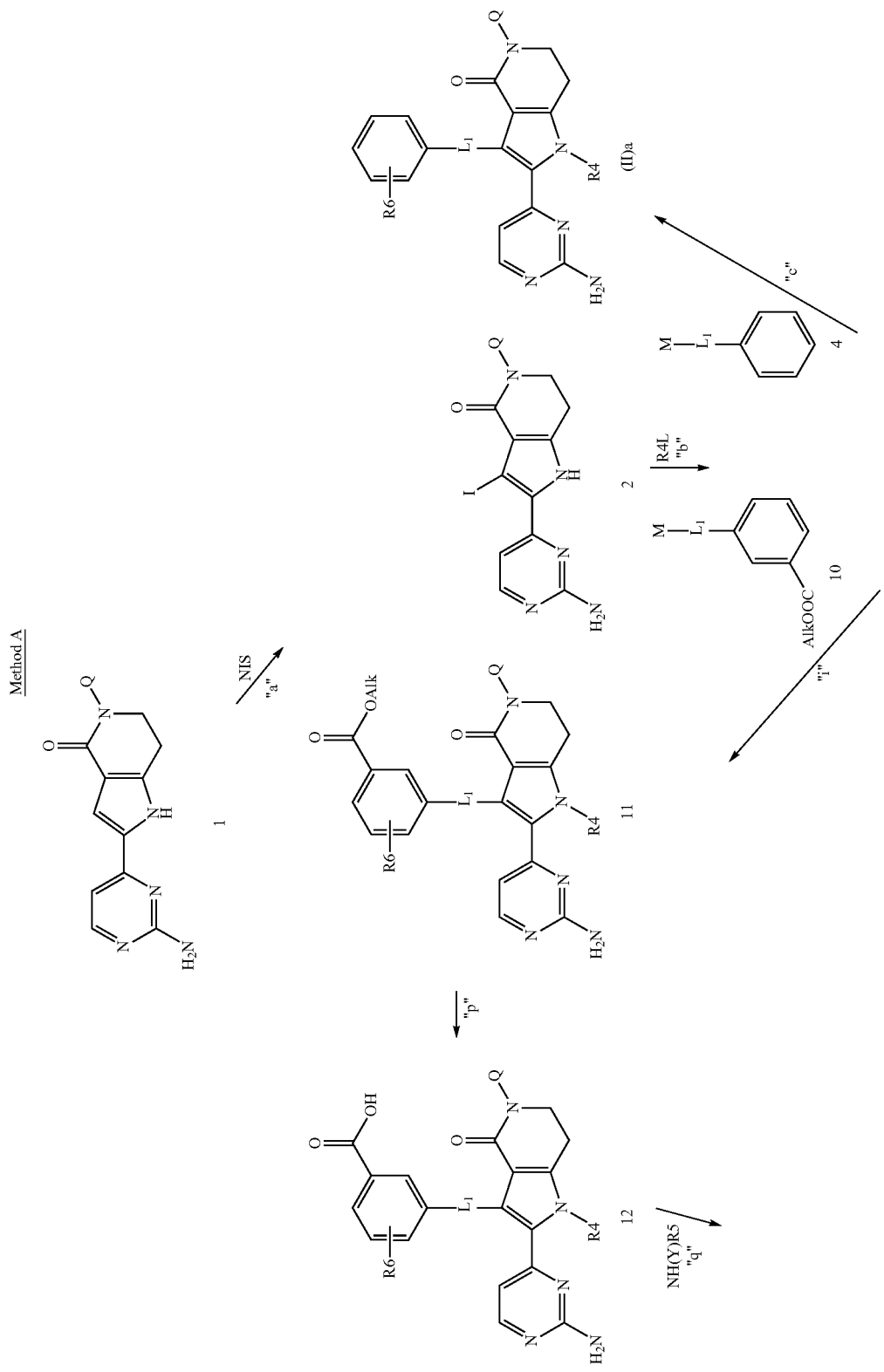

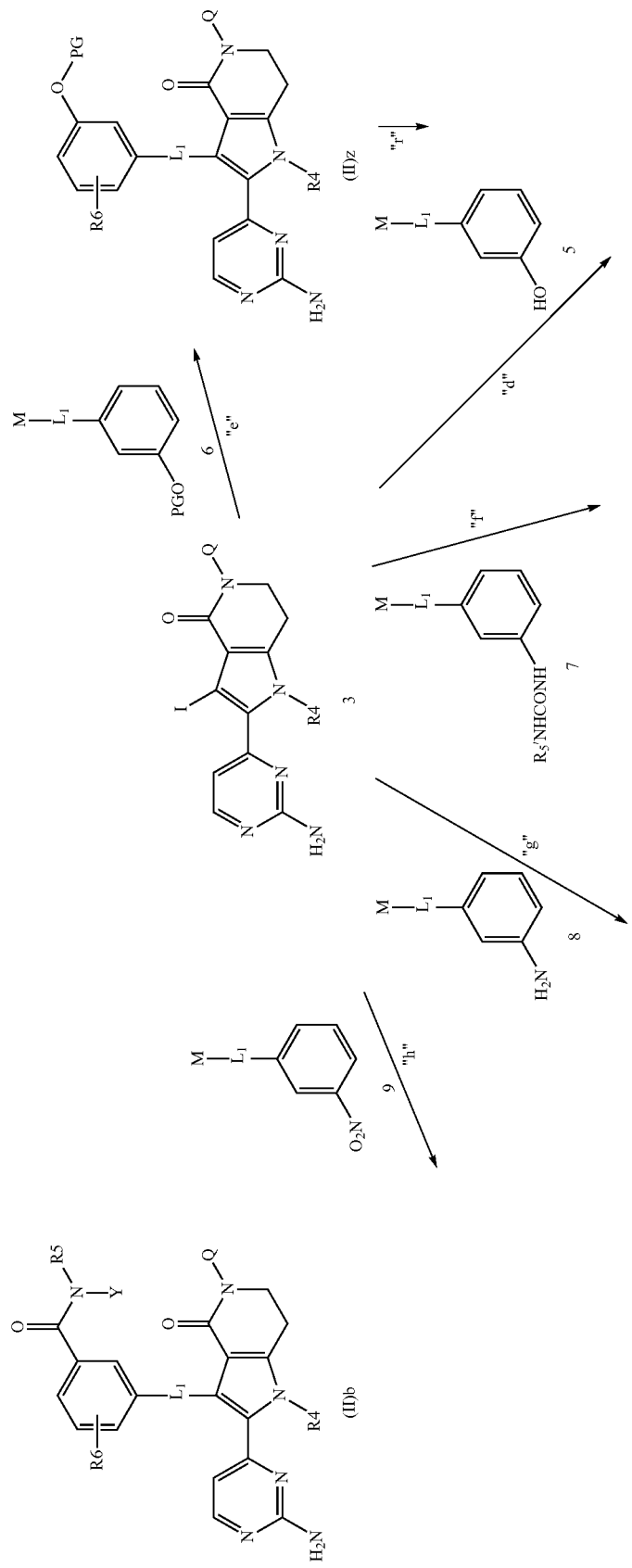

-continued
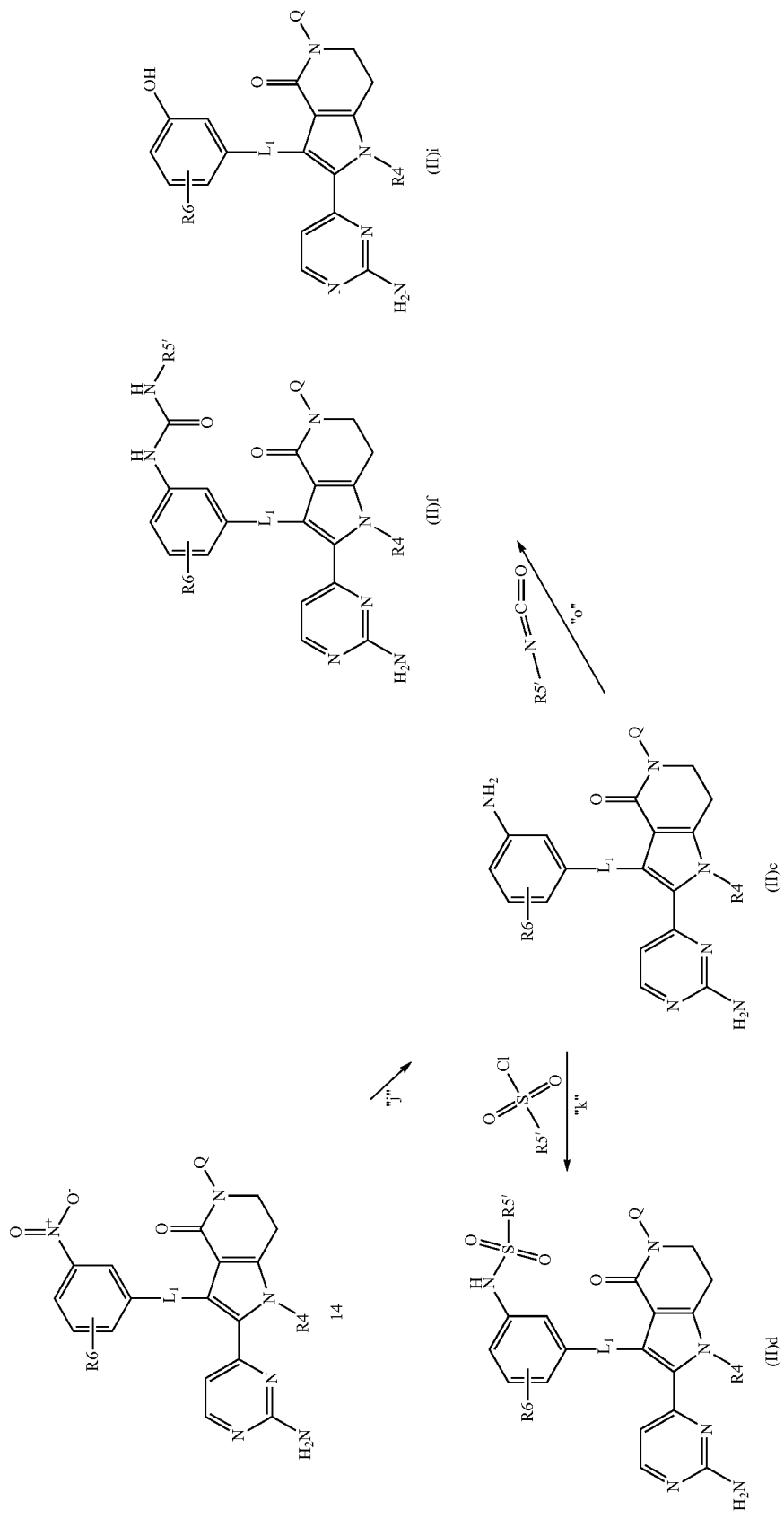

-continued
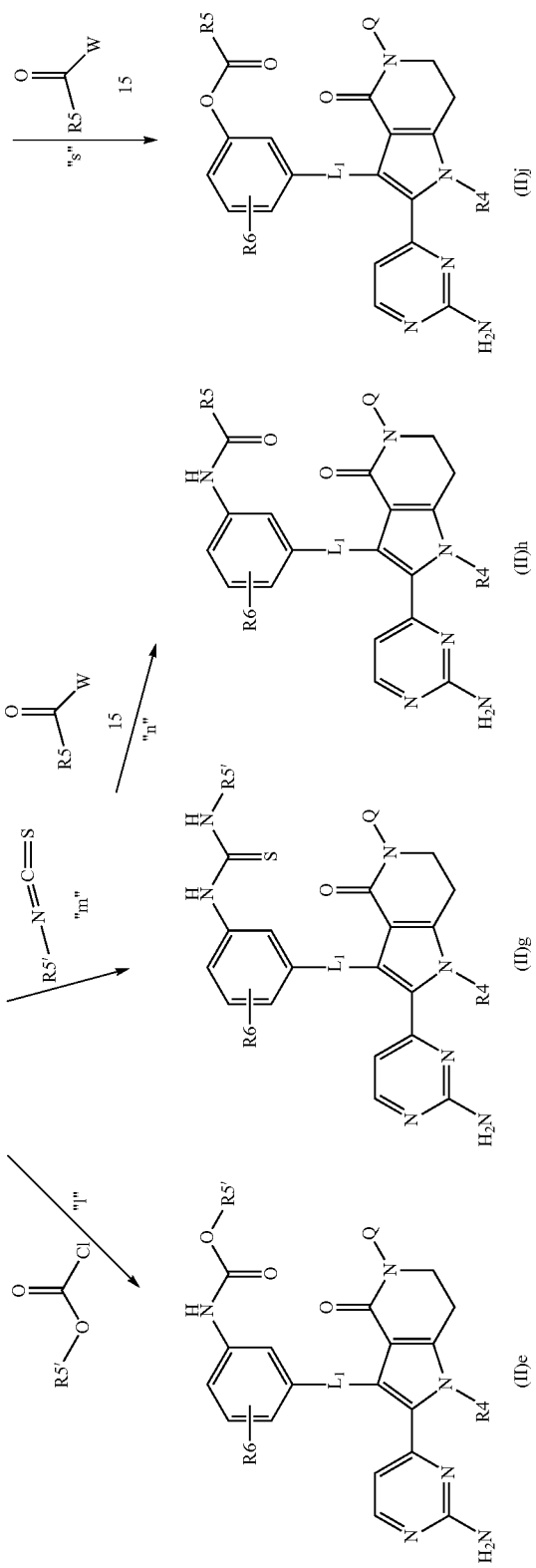

In the above scheme $L_1$, R4, R5, R6, Y and Q are as defined above, R5' is as R5 but not hydrogen, PG represents a protecting group of the hydroxyl moiety, such as methyl, benzyl, p-methoxybenzyl, trityl and the like, M is $B(OH)_2$, $B(OAlk)_2$, $Sn(Alk)_3$, $Al(Alk)_2$, ZnHal, MgHal, $ZrCp_2Hal$, or an hydrogen atom, W is a suitable leaving group such as hydroxy or halogen, L is OH, or a group that optionally upon activation may work as a leaving group, such as a halogen atom, a tosylate, mesylate or triflate, and ALK is $(C_1-C_6)$alkyl.

In a synthetic process for the preparation of a compound of formula (II), which is described in method A, in step "a" a compound of formula 1, which is prepared according to methods reported in WO 2007068728 cited above, is reacted with N-iodo succinimide (NIS) to form a compound of formula 2, which, in step "b" is treated with a suitable alkylating agent of formula R4L to afford a compound of formula 3. In step "c" such a compound is cross-coupled with a suitable electrophile of general formula 4 to give a compound of general formula (II)a. Alternatively, when such a cross coupling reaction is performed using an electrophile of general formula 5, 6, 7, 8, 9, or 10, a compound of formula (II)i, (II)z, (II)f, (II)c, 14, or 11 are respectively obtained, as described in step "d", "e", "f", "g", "h" and "i". The compound of formula 11 can be hydrolyzed according to step "p" and the carboxylic acid of general formula 12 so obtained can be condensed with a suitable amine to form a compound of formula (II)b according to step "q". The compound of formula 14 can be reduced to form an amino derivative of formula (II)c according to step T. The compound (II)c can be further elaborated reacting it with different types of electrophiles to provide respectively a compound of formula (II)d, (II)e, (II)g, (II)h or (II)f, according to step "k", "l", "m", "n", and "o". Yet, according to another meaning of the present invention a compound of formula (II)i can also be obtained in step "r" by removal of the protecting group PG from a compound of formula (II)z. It is readily understood by those skilled in the art, that a variety of methods, which are well known in the art, can be used to remove such a protecting group depending on the nature of the PG. According to step "s" a compound of formula (II)i can further be transformed into another compound of formula (II)j by condensation with a compound of formula 15.

According to step "a" of method A, the reaction between a compound of formula 1 and N-iodosuccinimide can be carried out in a variety of solvents such as, for instance, dichloromethane, tetrahydrofuran, 1,4-dioxane, acetone, acetonitrile, N,N-dimethylformamide, at a temperature ranging from −40° C. to reflux and for a time ranging from 30 minutes to about 24 hours.

According to step "b" of method A the N-alkylation of a compound of formula 2 can be accomplished using a compound of formula LR4 wherein L is OH, in which case the Mitsunobu conditions can be employed, or L is a group that optionally upon activation, may work as a leaving group, such as a halogen atom, a tosylate, mesylate or triflate. In the former instance, that is, when a Mitsunobu protocol is employed, the reaction can be accomplished using a dialkyl azodicarboxylate, such as diethyl azodicarboxylate (DEAD), diisopropyl azodicarboxylate (DIAD) or the like, in the presence of a trialkyl or triaryl phosphine, preferably triphenyl phosphine in a suitable solvent such as tetrahydrofuran, 1,4-dioxane, 1,2-dimethoxyethane, acetonitrile. When L is a halogen atom or a group such as tosylate, mesylate or triflate or the like the conversion can be accomplished using a suitable base such as, for instance, NaH, $K_2CO_3$, $Cs_2CO_3$, NaOH, DBU, LiHMDS and the like, in a suitable solvent such as dichloromethane, tetrahydrofuran, 1,4-dioxane, 1,2-dimethoxyethane, methanol, ethanol, isopropanol, acetonitrile, acetic acid, N,N-dimethylformamide, N,N-dimethylacetamide, dimethylsulfoxide and the like. Said reactions can be carried out at temperatures ranging from 0° C. to reflux and for a time ranging from 30 minutes to about 48 hours.

According to step "c" of method A, the intermediate of formula 3 is cross-coupled with a suitable organometal of formula 4, such as, for instance, an organoboron compound (Suzuki reaction), an organotin compound (Stille reaction), an organozinc, organoalluminium or organozirconium compound (Negishi reaction), and the like, or with an olefin derivative (Mizoroki-Heck reaction). Said reactions are well known among those with ordinary skills in the art. One preferred reaction is the Stille reaction where an appropriate organotin compound is used in the presence of a palladium-based catalyst, such as, for instance, bis(triphenylphosphine) palladium dichloride, optionally in the presence of CuI and a tetraalkylammonium salt, such as tetraethylammonium chloride, and a suitable base such as CsF or the like. Another preferred reaction is the Mizoroki-Heck reaction where an appropriate olefin derivative is used in the presence of a palladium-based catalyst, such as, for instance, palladium tetrakis triphenyl phosphine, and a suitable base, such as triethylamine and the like.

According to steps "d", "e", "f", "g", "h", "i" of method A, the conversion of the compound of formula 3 into compounds of formula (II)i, (II)z, (II)f, (II)c, 14, or 11 is accomplished as described under step "c" of method A using compounds of formula 5, 6, 7, 8, 9, or 10 as electrophiles.

According to step "p" of method A, a compound of formula 11 can be hydrolyzed according to well-known methods, for instance in the presence of aqueous alkaline solutions such as aqueous sodium hydroxide or lithium hydroxide in solvents such as tetrahydrofuran, methanol water and mixtures thereof. Said reaction typically requires from 30 minutes to 96 hours and is carried out at a temperature ranging from 0° C. to reflux.

According to step "q" of method A a compound of formula 12 is then transformed in an amide of formula (II)b by the condensation with a suitable amine. It is clear to the skilled person that this reaction can be accomplished in a variety of ways and operative conditions, which are widely known in the art for the preparation of carboxamides. As an example, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. Said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step "j" of method A, a compound of formula 14 can be reduced to an amino derivative of formula (II)c. The reaction may be carried out in a variety of ways and operative conditions, which are widely known in the art for reducing a nitro to an amino group. Preferably, this reaction is carried out in a suitable solvent such as, for instance, water, methanol, tetrahydrofuran, 1,4-dioxane, N,N-dimethylformamide, ethyl acetate, or a mixture thereof, in the presence of a suitable reducing agent, such as, for instance, hydrogen and a hydrogenation catalyst, or by treatment with cyclohexene or cyclohexadiene and a hydrogenation catalyst, or by treatment with tin (II) chloride, or by treatment with zinc or zinc(II) chloride and aqueous hydrochloric acid or acetic acid or ammonium chloride, at a temperature ranging from 0° C. to reflux and for a time varying from about 1 hour to about 96 hours. The hydrogenation catalyst is usually a metal, most often palladium, which can be used as such or supported on carbon.

According to step "k" of method A, a compound of formula (II)c is reacted with a sulfonyl chloride to afford a compound of formula (II)d. Such a reaction is carried out in the presence of a suitable base, such as for instance, pyridine, N-methyl morpholine, diisopropyl ethylamine, in the appropriate solvent such as pyridine, dichloromethane or tetrahydrofuran, at a temperature ranging from 0° C. to reflux and for a time varying from about 1 hour to about 7 days.

According to step "l" of method A, a compound of formula (II)c is reacted with a chloroformate to afford a compound of formula (II)e. Such a reaction is carried out in the appropriate solvent such as tetrahydrofuran, N,N-dimethylformamide, dichloromethane, chloroform, acetonitrile, toluene or mixtures thereof, at a temperature ranging from about −10° C. to reflux and for a time varying from about 30 minutes to about 96 hours. The reaction is normally carried out in the presence of an opportune proton scavenger such as triethylamine, N,N-diisopropylethylamine or pyridine.

According to step "o" of method A, a compound of formula (II)c is reacted with the appropriate isocyanate to afford an urea of formula (II)f. Such a reaction is carried out in a suitable solvent such as dichloromethane or tetrahydrofuran, normally at a temperature ranging from about −10° C. to reflux and for a time varying from about 30 minutes to about 96 hours.

According to step "m" of method A, a compound of formula (II)c is reacted with an appropriate thioisocyanate to afford a thiourea of formula (II)g. Such a reaction is carried out in a suitable solvent such as dichloromethane or tetrahydrofuran, normally at a temperature ranging from about −10° C. to reflux and for a time varying from about 30 minutes to about 96 hours.

According to step "n" of method A, a compound of general formula (II)c is transformed into an amide of formula (II)h by condensation with any derivative of formula 15. It is clear to the skilled person that this reaction can be accomplished in a variety of ways and operative conditions, which are widely known in the art for the preparation of carboxamides. As an example, when W is an halogen such as chloride, the reaction is performed in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction is carried out in the presence of an opportune proton scavenger such as triethylamine, N,N-diisopropylethylamine or pyridine. When W is an hydroxy group, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. The said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step "r" of method A, a compound of formula (II)z can be transformed into a compound of formula (II)i by removing the protecting group PG. When PG is for instance a methyl group, deprotection can be accomplished using a boron or aluminum trihalide, such as $BBr_3$ or $AlCl_3$ in a suitable solvent such as dichloromethane, nitrobenzene or the like, or using hydrogen bromide or iodide in a suitable solvent such as, for instance acetic acid. Said reactions are normally carried out at a temperature ranging from about −20° C. to reflux and for a suitable time, for instance from about 30 minutes to about 96 hours. When said protecting group is, for instance, benzyl, p-methoxybenzyl or trityl, transformation of a compound of formula (II)z into a compound of formula (II)i is accomplished using strong acids such as for instance trifluoroacetic acid in a suitable cosolvent such as dichloromethane at temperature ranging from 20° C. to reflux or above, provided that the reaction is carried out in a sealed vial heating for instance with a microwave oven, for a time ranging from 30 minutes to about 24 hours. Depending on the nature of PG and on the deprotection conditions, both protecting groups PG and Q may be simultaneously removed obtaining directly a compound of formula (I).

According to step "s" of method A, a compound of formula (II)i can be transformed into a compound of formula (II)j by condensation with any derivative of formula 15. Such reaction can be carried out following the conditions reported for step "n" of method A mentioned above.

Method B
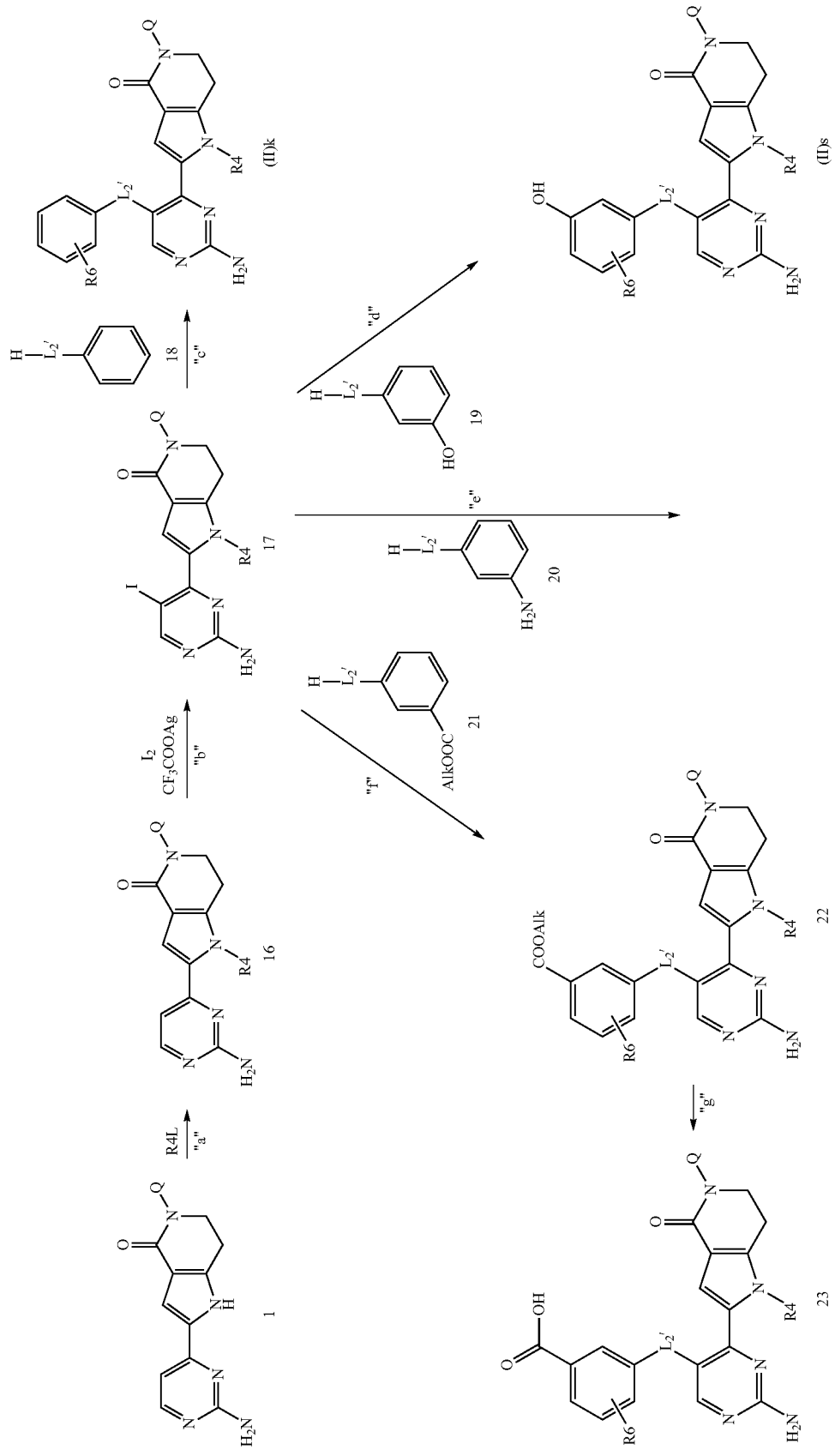

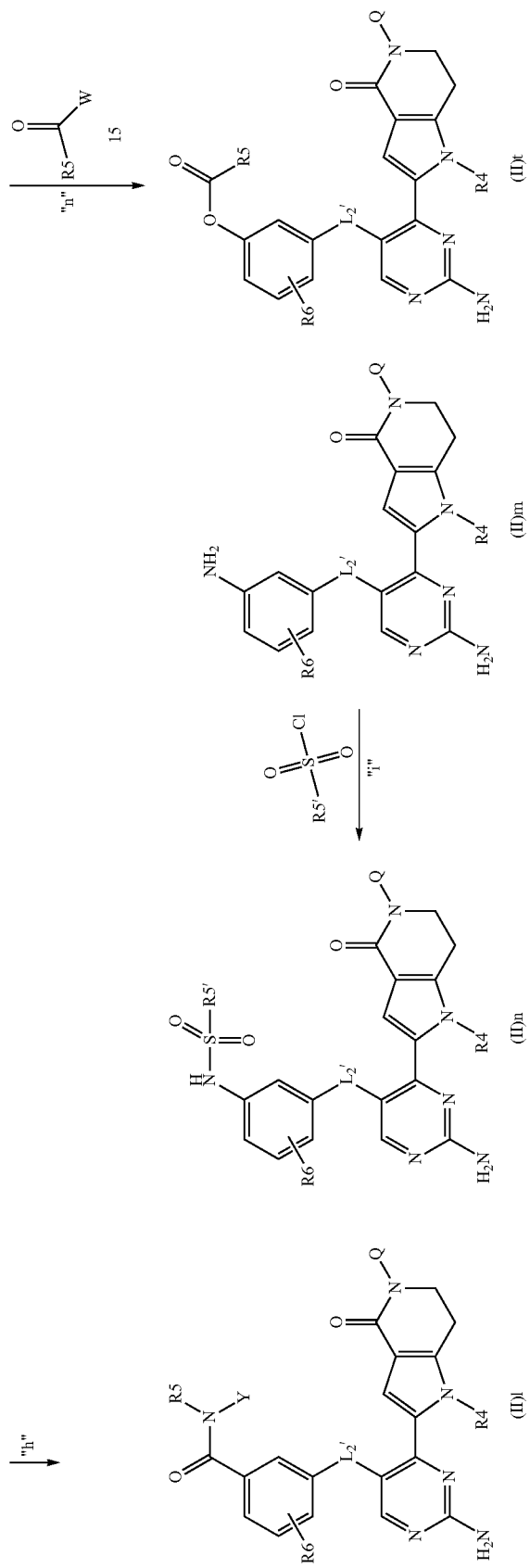

-continued
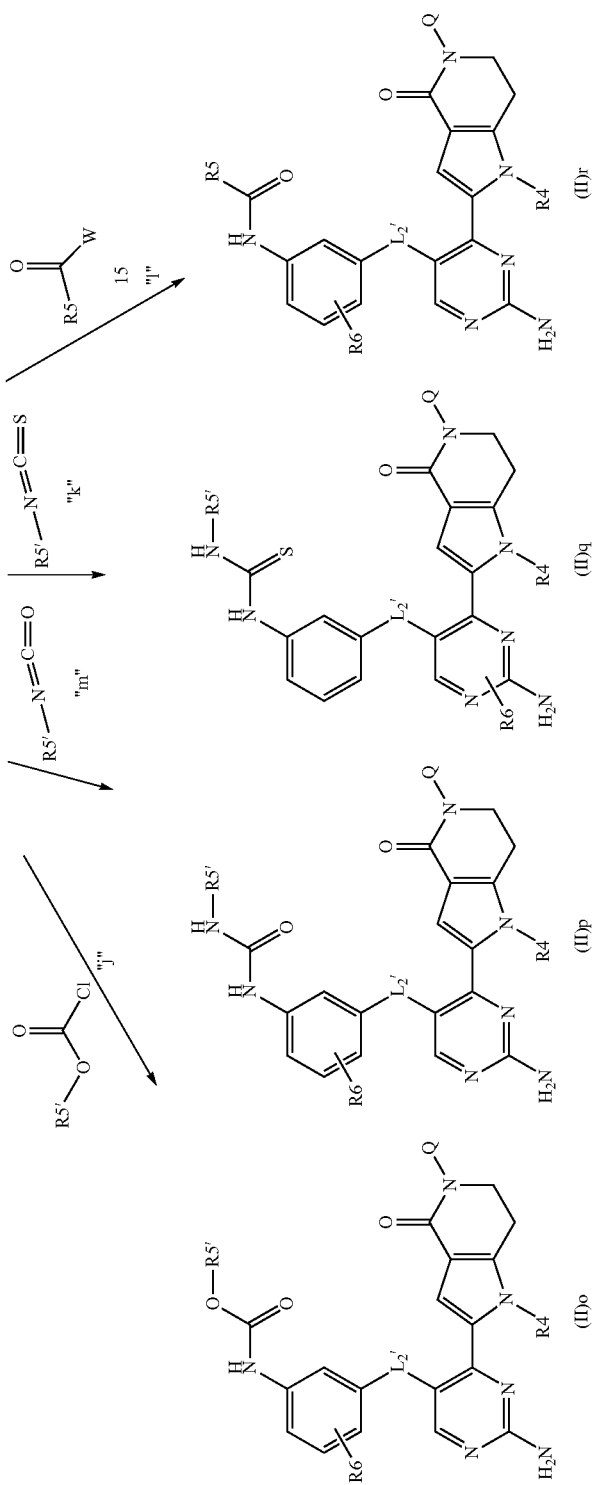

In the above scheme R4, R5, R5', R6, Y, Q, W, L and PG are as defined above and L2' is as L2 defined above except CH₂—CH₂. In a synthetic process for the preparation of a compound of formula (II), which is described in method B, in step "a" a compound of formula 1, which is prepared according to methods reported in WO 2007068728 cited above, is treated with a suitable alkylating agent of formula R4L to afford a compound of formula 16, which, in step "b" is iodinated at position 5' to afford a compound of general formula 17. In step "c" such a compound is cross-coupled with a suitable electrophile of general formula 18 to give a compound of general formula (II)k. Alternatively, when such a cross coupling reaction is performed using an electrophile of general formula 19, 20 or 21, as described in step "d", "e" and "f", compounds of formula (II)s, (II)m or 22 are obtained. The latter can be hydrolyzed according to step "g" and the carboxylic acid of general formula 23 so obtained can be condensed with a suitable amine to form a compound of formula (II)l according to step "h". A compound of general formula (II)m can be further elaborated according to steps "i", "j", "k", "l" and "m" where it is reacted with different types of electrophiles to provide respectively a compound of formula (II)n, (II)o, (II)q, (II)r and (II)p. According to step "n" a compound of formula (II)s can further be transformed into another compound of formula (II)t by condensation with a compound of formula 15.

According to step "a" of method B the N-alkylation of a compound of formula 1 can be accomplished as described under step "b" of method A.

According to step "b" of method B the iodination at position 5' of a compound of general formula 16 can be accomplished using iodine in the presence of silver trifluoroacetate. Such a reaction can be carried out in a variety of solvents such as, for instance, dimethylsulfoxide, N,N-dimethylformamide, N,N-dimethylacetamide, dichloromethane, tetrahydrofuran, 1,4-dioxane, 1,2-dimethoxyethane, acetonitrile, at a temperature ranging from 0° C. to reflux and for a time ranging from 30 minutes to about 24 hours.

According to step "c" of method B, the intermediate of formula 17 is cross-coupled with a suitable electrophile of formula 18, such as, for instance, an olefin derivative (Mizoroki-Heck reaction) or a terminal alkyne derivative (Sonogashira reaction). Said reactions are well known among those with ordinary skills in the art. The Mizoroki-Heck reaction can normally be performed in the presence of a palladium-based catalyst, such as, for instance, palladium tetrakis triphenyl phosphine, and a suitable base, such as triethylamine and the like. The Sonogashira reaction, can be carried out in the presence of a suitable palladium catalyst such as PdCl₂(PPh₃)₂, Pd(PPh₃)₄, and the like, and of a suitable copper catalyst, such as CuI. Said reaction is carried out in the presence of a suitable base, such as triethylamine, diethylamine, diisopropylamine and the like, optionally in the presence of a phosphine ligand, such as triphenylphosphine. Both reactions are normally carried out at temperatures ranging from −20° C. to reflux and for a time ranging from 30 minutes to about 48 hours.

According to steps "d", "e" and "f" of method B, the conversion of the compound of formula 17 into a compound of formula (II)s, (II)m or 22 is accomplished as described under step "c" of method B using respectively a compound of formula 19, 20 or 21 as electrophile.

Steps "g" and "h" of Method B are respectively carried out as described under steps "p" and "q" of Method A.

Steps from "i" to "m" of method B are respectively carried out as described under steps "k" to "o" of method A.

Steps "n" of Method B is carried out as described under step "s" of Method A.

The compounds of formula (II)k-t wherein L2 is CH═CH or C≡C obtained in steps "a" to "n" of Method B, can be transformed into the corresponding compounds of formula (II)k'-t' wherein L2 is CH₂—CH₂ by hydrogenation in the presence of a suitable catalyst.

The reaction may be carried out in a variety of ways and operative conditions, which are widely known in the art, preferably this reaction is carried out in a suitable solvent such as, for instance, methanol, ethanol, acetonitrile, tetrahydrofuran, 1,4-dioxane, N,N-dimethylformamide, ethyl acetate, or a mixture thereof, in the presence of a suitable reducing agent, such as, for instance, hydrogen and a hydrogenation catalyst, at a temperature between 25 and 40° C., for a time varying from about 1 hour to about 96 hours. The hydrogenation catalyst is usually a metal, most often palladium, which can be used as such or supported on carbon.

Method C

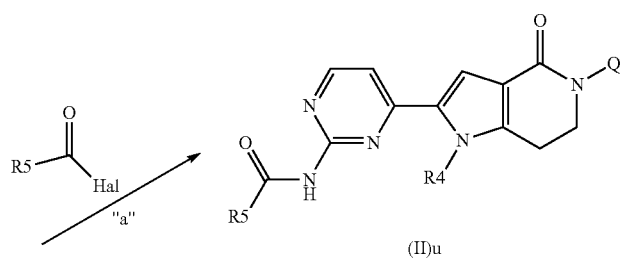

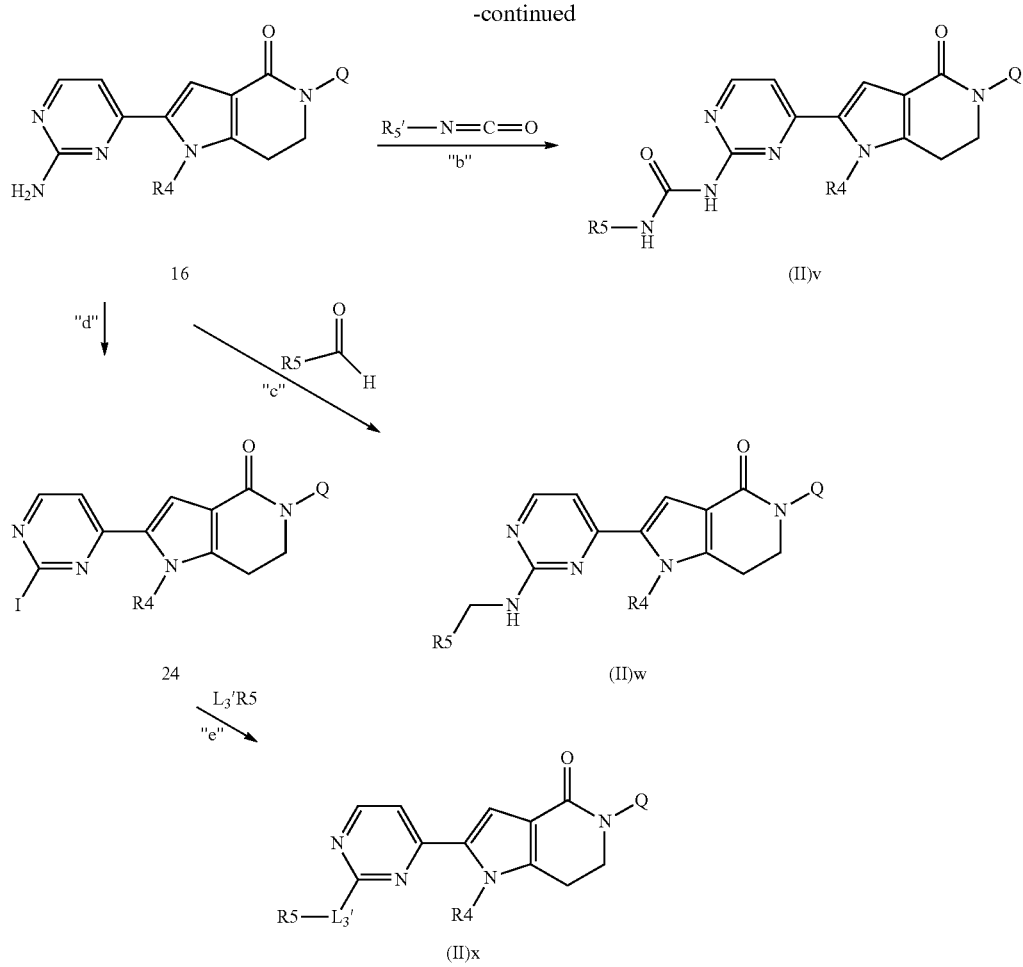

In the above scheme, R4, R5, R5' and Q are as defined above, and L₃' is a CH=CH or C≡C group and Hal is halogen.

In a synthetic process for the preparation of a compound of formula (II), which is described in method C, in step "a" a compound of formula 16, which is prepared according to step "a" of Method B, is reacted with an acylating agent to afford an amide of general formula (II)u. In step "b" a compound of formula 16 is reacted with an isocyanate to form a compound of general formula (II)v. In step "c", a compound of formula 16 is reacted with a suitable aldehyde under reductive amination conditions to afford a compound of general formula (II)w. In step "d" a Sandmeier reaction is used to convert a compound of formula 16 into a iodopyrimidine derivative of formula 24. In step "e" such a compound is cross-coupled with a suitable electrophile of general formula L₃'R5 to give a compound of general formula (II)x.

According to step "a" of method C, a compound of formula 16 is converted in a carboxamide of formula (II)u. It is clear to the skilled person that this reaction can be accomplished in a variety of ways and operative conditions, which are widely known in the art for the preparation of carboxamides. As an example, a compound of formula 16 is acylated with a compound of general formula R5COHal, wherein Hal is an halogen, such as chloride; the reaction is performed in a suitable solvent such as, for instance, dichloromethane, chloroform, tetrahydrofuran, diethyl ether, 1,4-dioxane, acetonitrile, toluene, or N,N-dimethylformamide, in the presence of a suitable base such as triethylamine, diisopropyl ethylamine, DBU and the like at a temperature ranging from about −10° C. to reflux and for a suitable time, for instance from about 30 minutes to about 96 hours. Preferred is the use of pyridine as the solvent, optionally in the presence of triethylamine and N,N-dimethylaminopyridine as a base at room temperature for approximately 24 hours.

According to step "b" of method C, a compound of formula 16 is converted in an urea derivative of formula (II)v by operating as described under step "o" of Method A.

According to step "c" of method C, a compound of formula 16 can be converted in a compound of formula (II)w according to conventional methods for carrying out reductive alkylation. Preferably, this reaction is carried out in a suitable solvent such as, for instance, methanol, N,N-dimethylformamide, dichloromethane, tetrahydrofuran, or a mixture thereof, in the presence of a suitable reducing agents such as, for instance, sodium borohydride, tetra-alkylammonium borohydride, sodium cyano borohydride, sodium triacetoxyborohydride, tetramethylammonium triacetoxy borohydride, hydrogen and a hydrogenation catalyst, and in the presence of an acid catalyst, such as, for instance, acetic acid, trifluoroacetic acid, at a temperature ranging from about 0° C. to reflux and for a time varying from about 1 hour to about 96 hours.

According to step "d" of method C, a compound of formula 16 is converted into a compound of formula 24. Said conversion is performed using sodium nitrite in water or aqueous solvents, in the presence of a mineral acid, such as hydrochloric acid, sulphuric acid and the like, or using isoamyl nitrite in a suitable solvent such as dichloromethane, dimethoxyethane, tetrahydrofuran and the like in the presence of diiodomethane or copper iodide, cesium iodide, iodine or a mixture of them at a temperature ranging from 0° C. to reflux and for a time ranging from 30 minutes to about 24 hours.

According to step "e" of method C, a compound of formula 24 may be cross-coupled with a suitable electrophile of formula $L_3'R5$ as reported above under step "c" of Method B.

Method D

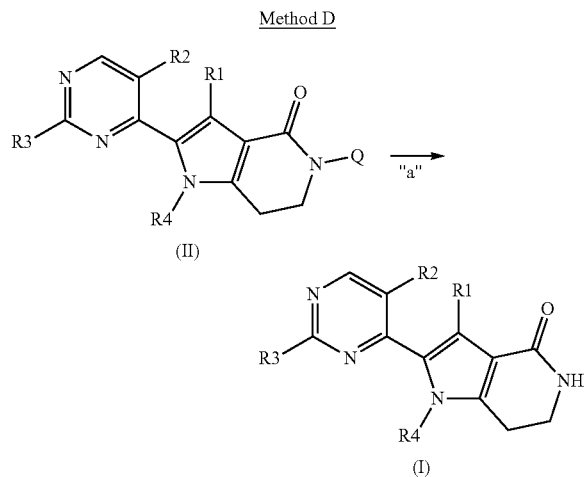

In the above scheme R1, R2, R3, R4 and Q are as defined above.

In a synthetic process for the preparation of a compound of formula (I), which is described in method D, the deprotection of a compound of formula (II) obtained in Method A, B and C, can be accomplished in a variety of ways according to conventional methods well known in the art (Green, Theodora W and Wuts, Peter G. M.—*Protective Groups in Organic Synthesis, Third Edition*, John Wiley & Sons Inc., New York (NY), 1999).

Preferably, when Q is a t-butoxycarbonyl residue is carried out in a suitable solvent such as dichloromethane or dioxane and in the presence of catalytic amounts of an acid such as hydrochloric acid or trifluoroacetic at a temperature ranging from room temperature to 90° C. and for a time ranging from about 1 to about 24 hours.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

The starting materials of the process object of the present invention, comprehensive of any possible variant, as well as any reactant thereof, are known compounds and if not commercially available per se may be prepared as described in the experimental section.

Pharmacology

Assays

In Vitro Cell Proliferation Assay Exponentially growing human melanoma cells A375 (with a mutated B-RAF) and human melanoma cells Mewo (with wild-type B-Raf) were seeded and incubated at 37° C. in a humidified 5% CO2 atmosphere. After 24 hours, scalar doses of the compound were added to the medium and cells oncubated for 72 hours. At the end of treatment, cells were washed and counted. Cell number was determined by a cellular adenosine triphosphate monitoring system. Cell proliferation was compared to control cells and the concentration inhibiting cell growth by 50% was calculated.

p-MAPK (T202/Y204) ArrayScan Assay

A375 human melanoma cells, having a mutated B-RAF, are seeded in 384-well poly-lysine coated plates (Matrix) at a density of 1000 cells/well with appropriate medium supplemented with 10% FCS and incubated for 16-24 hours. Cells are treated for 1.5 or 2 hours with increasing doses of compounds (starting dose 10 µM, dilution factor 2.5). At the end of the treatment cells are fixed with p-formaldehyde 3.7% for 15-30 min, then washed twice with D-PBS (80 □l/well) and permeabilized with D-PBS containing 0.1% Triton X-100 and 1% BSA (Sigma-Aldrich) for 15 minutes at room temperature (staining solution). Anti-phospho-MAPK (T202/Y204) monoclonal antibody E10 (Cell Signaling, cat. #9106) diluted 1:100 is added in staining solution and incubated for 1 hour at 37° C. After removal of the primary antibody solution, the anti-mouse Cy™2-conjugated (Green) secondary antibody (Amersham) diluted 1:500 in staining solution containing 2 µg/ml DAPI is added. The plate is incubated for 1 hour at 37° C., washed twice and then red with Cellomics' ArrayScan VTI (4 fields/well, CytoNucTrans algorithm).

The parameter "MEAN_RingAvgIntenCh2", which measures the mean cytoplasmatic fluorescence intensity associated to p-MAPK staining, is reported as the final result.

B-RAF mutations, that constitutively activate the kinase, have been identified in the majority of melanoma and a large fraction of colorectal and papillary thyroid carcinoma. The growth of cells with activated B-RAF strictly depends on B-RAF activity. Given the above assays, the compounds of formula (I) result to posses a remarkable activity in inhibiting cell proliferation, with $IC_{50}$ values lower than 10 µM, more potent on the cell line with mutated B-Raf (A375) than on the cell line with wild-type B-Raf (Mewo), as reported in the following table.

In the same table the data obtained with compounds of formula (I) in the ArrayScan assay are also reported and demonstrate the ability of the compounds of formula (I) to inhibit the signal transduction pathway controlled by B-RAF activation in A375 cell line with mutated B-RAF. The $IC_{50}$ values are always lower than 10 µM and are in agreement with the $IC_{50}$ values obtained in the proliferation assay on the same cell line, confirming that the antiproliferative activity of the compounds is due to the inhibition of B-RAF activity.

TABLE 1

| | | Proliferation and Array Scan data | | |
| --- | --- | --- | --- | --- |
| | | Proliferation | | Array Scan |
| Cpd. N° | Name | A375 $IC_{50}$ (µM) | Mewo $IC_{50}$ (µM) | A375 $IC_{50}$ (µM) |
| 1 | 1-{3-[2-(2-Amino-pyrimidin-4-yl)-1-methyl-4-oxo-4,5,6,7-tetrahydro-1H-pyrrolo[3,2-c]pyridin-3-yl]-phenyl}-3-(4-trifluoromethyl-phenyl)-urea | 8.22 | >10 | 5.60 |

TABLE 1-continued

Proliferation and Array Scan data

| | | Proliferation | | Array Scan |
|---|---|---|---|---|
| Cpd. N° | Name | A375 IC$_{50}$ (μM) | Mewo IC$_{50}$ (μM) | A375 IC$_{50}$ (μM) |
| 2 | 2-[2-Amino-5-(3-hydroxy-phenylethynyl)-pyrimidin-4-yl]-1-methyl-1,5,6,7-tetrahydro-pyrrolo[3,2-c]pyridin-4-one | 6.09 | 7.91 | >10 |
| 3 | 2-[2-Amino-5-(3-hydroxy-phenylethynyl)-pyrimidin-4-yl]-1-(2-fluoro-ethyl)-1,5,6,7-tetrahydro-pyrrolo[3,2-c]pyridin-4-one | 6.46 | 4.75 | 0.71 |
| 4 | 4-Bromo-thiophene-2-carboxylic acid[4-(1-methyl-4-oxo-4,5,6,7-tetrahydro-1H-pyrrolo[3,2-c]pyridin-2-yl)-pyrimidin-2-yl]-amide | 0.49 | 2.45 | 0.46 |
| 6 | 2-[2-(3-Chloro-benzylamino)-pyrimidin-4-yl]-1-methyl-1,5,6,7-tetrahydro-pyrrolo[3,2-c]pyridin-4-one hydrochloride | 1.76 | 5.79 | 2.11 |
| 7 | 2-{2-[(4-Bromo-thiophen-2-ylmethyl)-amino]-pyrimidin-4-yl}-1-methyl-1,5,6,7-tetrahydro-pyrrolo[3,2-c]pyridin-4-one hydrochloride | 2.91 | 9.76 | 2.14 |
| 8 | 2-[2-(3-Chloro-phenylethynyl)-pyrimidin-4-yl]-1-methyl-1,5,6,7-tetrahydro-pyrrolo[3,2-c]pyridin-4-one | 0.21 | 0.82 | 0.93 |
| 9 | 2-{2-[(E)-2-(3-Chloro-phenyl)-vinyl]-pyrimidin-4-yl}-1-methyl-1,5,6,7-tetrahydro-pyrrolo[3,2-c]pyridin-4-one | 0.37 | 1.22 | 0.40 |
| 10 | 3-Chloro-N-[4-(1-methyl-4-oxo-4,5,6,7-tetrahydro-1H-pyrrolo[3,2-c]pyridin-2-yl)-pyrimidin-2-yl]-benzamide | 0.45 | 1.98 | 1.60 |
| 11 | Thiophene-2-carboxylic acid [4-(1-methyl-4-oxo-4,5,6,7-tetrahydro-1H-pyrrolo[3,2-c]pyridin-2-yl)-pyrimidin-2-yl]-amide | 1.70 | 2.42 | 2.91 |
| 12 | Thiophene-3-carboxylic acid [4-(1-methyl-4-oxo-4,5,6,7-tetrahydro-1H-pyrrolo-[3,2-c]pyridin-2-yl)-pyrimidin-2-yl]-amide | 2.50 | 6.41 | 2.38 |
| 14 | 4-Methyl-thiophene-2-carboxylic acid [4-(1-methyl-4-oxo-4,5,6,7-tetrahydro-1H-pyrrolo[3,2-c]pyridin-2-yl)-pyrimidin-2-yl]-amide | 0.77 | 2.64 | 1.45 |

From all of the above, the novel compounds of formula (I) of the invention appear to be particularly advantageous in the therapy of diseases caused by dysregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 1 g per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| | |
|---|---|
| g (grams) | mg (milligrams) |
| ml (milliliters) | mM (millimolar) |
| µM (micromolar) | mmol (millimoles) |
| h (hours) | MHz (Mega-Hertz) |
| mm (millimeters) | Hz (Hertz) |
| M (molar) | min (minutes) |
| mol (moles) | TLC (thin layer chromatography) |
| r.t. (room temperature) | TEA (triethylamine) |
| TFA (trifluoroacetic acid) | DMF (N,N-dimethyl formamide) |
| DIPEA (N,N-diisopropyl-N-ethylamine) | DCM (dichloromethane) |
| THF (tetrahydrofuran) | Hex (hexane) |
| MeOH (Methanol) | DMSO (dimethylsulfoxide) |
| TIPS (triisopropylsilyl) | bs (broad singlet) |
| TBDMS (dimethyl-tert-butylsilyl) | Ac (acetyl) |
| BOC (tert-butyloxycarbonyl) | Ac$_2$O acetic anhydride |
| NaH = sodium hydride, 60% in mineral oil | ESI = electrospray ionization |
| TBTU ((2-(1H-benzotriazol-1-yl)-1,1,3,3-tetramethyluronium tetrafluoroborate) | |
| RP-HPLC (reverse phase high performance liquid chromatography) | |
| With the aim to better illustrate the present invention, without posing any limitation to it, the following examples are now given. | |

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, $CH_2Cl_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A).

Electrospray (ESI) mass spectra were obtained on a Thermo Finnigan LCQ Deca XP ion trap. HPLC-UV-MS analyses, used to assess compound purity, were carried out combining the ion trap MS instrument with HPLC system Surveyor (Thermo Finnigan) equipped with an autosampler and a diode array detector (UV detection 215-400 nm). Instrument control, data acquisition and processing were performed by using Xcalibur 1.4 SR1 software (Thermo Finnigan), HPLC chromatography was run at room temperature, and 1 ml/min flow rate, using a Phenomenex Gemini NX C18 column (4.6×50 mm; 3 µm). Mobile phase A was ammonium acetate 5 mM buffer (pH 5.5 with acetic acid): acetonitrile 95:5, and mobile phase B was ammonium acetate 5 mM buffer (pH 5.5 with acetic acid): acetonitrile 5:95; the gradient was from 0 to 100% B in 7 minutes then hold 100% B for 2 minutes before requilibration.

Exact mass data ESI(+) were obtained on a Waters Q-T of Ultima directly connected with micro HPLC 1100 Agilent as previously described [M. Colombo, F. Riccardi-Sirtori, V. Rizzo, *Rapid Commun. Mass Sectrom.* 2004, 18, 511-517].

Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 µm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min, Flow rate 20 mL/min. In alternative, mobile phase A was water-0.1% $NH_3$, and mobile phase B was acetonitrile. Gradient from 10 to 100% B in 8 min, hold 100% B 2 min, Flow rate 20 mL/min.

1H-NMR spectrometry was performed on a Mercury VX 400 operating at 400.45 MHz equipped with a 5 mm double resonance probe [1H (15N-31P) ID_PFG Varian].

Example 1

2-(2-Amino-pyrimidin-4-yl)-3-(3-methoxy-phenyl)-1-methyl-1,5,6,7-tetrahydro-pyrrolo[3,2-c]pyridin-4-one trifluoroacetate

[(I), R1=3-methoxyphenyl, R2=H, R3=$NH_2$, R4=Me]

The above compound was prepared according to Methods A and D as described below.

Step a (Method A)

tert-butyl 2-(2-aminopyrimidin-4-yl)-3-iodo-4-oxo-1,4,6,7-tetrahydro-5H-pyrrolo[3,2-c]pyridine-5-carboxylate

[(2), Q=Boc]

N-iodo succinimide (0.75 g, 3.34 mml) was added to a solution of 2-(2-amino-pyrimidin-4-yl)-4-oxo-1,4,6,7-tetrahydro-pyrrolo[3,2-c]pyridine-5-carboxylic acid tert-butyl ester [(1), Q=Boc] (1.0 g, 3.03 mmol) in dry DMF (15 mL) and the reaction mixture was stirred at room temperature overnight, in a flask surrounded by an aluminium sheet. After reaction completion, a solution of $Na_2S_2O_3$ (10%, 0.100 ml) was added and the product was extracted with DCM (3×0.100 mL). The organic layer was dried over $Na_2SO_4$ and the solvent was removed under reduced pressure to yield the crude 2-(2-amino-pyrimidin-4-yl)-3-iodo-4-oxo-1,4,6,7-tetrahydro-pyrrolo[3,2-c]pyridine-5-carboxylic acid tert-butyl ester as a yellow solid (1.240 g, 2.72 mmol, 90%).

HPLC (254 nm): Rt: 4.55 min.

$^1$H-NMR (401 MHz, DMSO-$d_6$) δ=12.25 (br. s., 1H), 8.32 (d, J=5.2 Hz, 1H), 7.49 (d, J=5.2 Hz, 1H), 6.46 (br. s., 2H), 3.93 (t, J=6.2 Hz, 2H), 2.95 (t, J=6.2 Hz, 2H), 1.51-1.46 (br.s., 9H).

HRMS (ESI) calcd for C16H19IN5O3 [M+H]+ 456.0527. found 456.0517.

Step b (Method A)

tert-butyl 2-(2-aminopyrimidin-4-yl)-3-iodo-1-methyl-4-oxo-1,4,6,7-tetrahydro-5H-pyrrolo[3,2-c]pyridine-5-carboxylate

[(3), R4=Me, Q=Boc]

Cesium carbonate (2.17 g, 6.68 mmol) was added to a solution of 2-(2-amino-pyrimidin-4-yl)-3-iodo-4-oxo-1,4,6,7-tetrahydro-pyrrolo[3,2-c]pyridine-5-carboxylic acid tert-butyl ester (1.38 g, 3.03 mmol) in DMF (60 mL) and the mixture was stirred at room temperature for 1 h. Methyl iodide (0.948 g, 6.68 mmol) was then added and after 2 h stirring at room temperature, water (0.100 mL) and DCM (0.100 mL) were poured into the reaction vessel. The organic layer was separated, dried over Na2SO4, and concentrated under vacuum to yield the crude 2-(2-amino-pyrimidin-4-yl)-3-iodo-1-methyl-4-oxo-1,4,6,7-tetrahydro-pyrrolo[3,2-c]pyridine-5-carboxylic acid tert-butyl ester as a brown solid (0.854 g, 1.8 mmol, 60%).

HPLC (254 nm): Rt: 5.44 min.

$^1$H-NMR (401 MHz, DMSO-$d_6$) δ=8.35 (d, J=5.1 Hz, 1H), 6.84 (d, J=5.0 Hz, 1H), 6.71 (s, 2H), 3.95 (t, J=6.3 Hz, 2H), 3.61 (s, 3H), 2.96 (t, J=6.3 Hz, 2H), 1.48 (s, 9H).

HRMS (ESI) calcd for C17H21IN5O3 [M+H]+ 470.0684. found 470.0688.

Step e (Method A)

2-(2-Amino-pyrimidin-4-yl)-3-(3-methoxy-phenyl)-1-methyl-4-oxo-1,4,6,7-tetrahydro-pyrrolo[3,2-c]pyridine-5-carboxylic acid tert-butyl ester

[(II)z, $L_1$=direct bond, R4=Me, R6=Hydrogen, PG=$CH_3$, Q=Boc]

To a solution of 2-(2-amino-pyrimidin-4-yl)-3-iodo-4-oxo-1,4,6,7-tetrahydro-pyrrolo-[3,2-c]pyridine-5-carboxylic acid tert-butyl ester (50 mg, 0.1 mmol) in toluene/EtOH 1:1 (2 mL), 1M aq Na2CO3 (0.25 mL, 0.25 mmol), LiCl (13 mg, 0.3 mmol), 3-methoxyphenylboronic acid (23 mg, 0.15 mmol) and (Ph3P)2PdCl2 (1.5 mg) were added and the mixture was stirred at 100° C. until disappearance of the starting material. The solvent was evaporated and the crude was purified by flash chromatography (eluant: DCM/MeOH 95:5) to afford 30 mg of 2-(2-amino-pyrimidin-4-yl)-3-iodo-1,4,6,7-tetrahydro-pyrrolo[3,2-c]pyridine-5-carboxylic acid tert-butyl ester (67% yield) as a white powder.

HPLC (254 nm): Rt: 5.10 min.

$^1$H-NMR (401 MHz, DMSO-$d_6$) δ=1.43 (s, 9H), 2.99 (t, J=6.22 Hz, 2H), 3.68 (s, 3H), 3.69 (s, 3H), 4.00 (t, J=6.22 Hz, 2H), 5.93 (d, J=5.12 Hz, 1H), 6.64 (br. s., 2H), 6.68-6.72 (m, 1H), 6.72-6.74 (m, 1H), 6.82 (dd, J=7.92 and 3.54 Hz, 1H), 7.17 (t, J=7.92 Hz, 1H), 7.97 (d, J=5.12 Hz, 1H), 7.71 (br. s., 2H), 7.93 (d, J=6.22 Hz, 1H).

HRMS (ESI) calcd for C24H28N5O4 [M+H]+ 450.2136. found 450.2119.

Operating in an analogous way the following Boc protected intermediates were obtained:

3-(3-Amino-phenyl)-2-(2-amino-pyrimidin-4-yl)-1-methyl-4-oxo-1,4,6,7-tetrahydro-pyrrolo[3,2-c]pyridine-5-carboxylic acid tert-butyl ester

[(II)c, $L_1$=direct bond, R4=Me, Q=Boc]

HPLC (254 nm): Rt: 4.40 min.

$^1$H-NMR (401 MHz, DMSO-$d_6$) δ=1.43 (s, 9H), 2.97 (t, J=6.22 Hz, 2H), 3.71 (s, 3H), 3.98 (t, J=6.22 Hz, 2H) 4.91 (br.s, 2H), 5.95 (d, J=5.24 Hz, 1H), 6.25-2.31 (m, 1H), 6.38-6.42 (m, 1H), 6.43-6.48 (m, 1H), 6.57 (br. s., 2H), 6.91 (t, J=7.80 Hz, 1H), 7.71 (br. s., 2H), 7.94 (d, J=5.24 Hz, 1H).

HRMS (ESI) calcd for C23H27N6O3 [M+H]+ 435.2139. found 435.2127.

2-(2-Amino-pyrimidin-4-yl)-3-(3-hydroxy-phenyl)-1-methyl-4-oxo-1,4,6,7-tetrahydro-pyrrolo[3,2-c]pyridine-5-carboxylic acid tert-butyl ester

[(II)i, $L_1$=direct bond, R4=Me, Q=Boc]

HPLC (254 nm): Rt: 5.28 min.

$^1$H-NMR (401 MHz, DMSO-$d_6$) δ=1.42 (s, 9H), 2.97 (t, J=6.28 Hz, 2H), 3.69 (s, 3H), 3.98 (t, J=6.22 Hz, 2H), 5.89 (d, J=5.12 Hz, 1H), 6.54 (dt, J=7.44, 1.20 Hz, 1H), 6.57 (dd, J=2.20, 1.60 Hz, 1H), 6.61 (s, 2H), 6.63 (ddd, J=8.08, 2.53, 0.85 Hz, 1H), 7.04 (t, J=7.80 Hz, 1H), 7.95 (d, J=5.12 Hz, 1H), 9.20 (s, 1H).

HRMS (ESI) calcd for C23H26N5O4 [M+H]+ 436.1980. found 436.1994.

2-(2-Amino-pyrimidin-4-yl)-1-methyl-4-oxo-3-((E)-styryl)-1,4,6,7-tetrahydro-pyrrolo[3,2-c]pyridine-5-carboxylic acid tert-butyl ester

[(II)a, $L_1$=E-ethenyl, R4=Me, Q=Boc]

HPLC (254 nm): Rt: 6.49 min.

$^1$H-NMR (401 MHz, DMSO-$d_6$) δ=1.49 (s, 9H), 2.96 (t, J=6.45 Hz, 2H), 3.58 (s, 3H), 3.99 (t, J=6.45 Hz, 2H), 6.67 (d, J=5.00 Hz, 1H), 6.76 (br. s., 2H), 7.15 (d, J=16.58 Hz, 1H), 7.19-7.25 (m, 1H), 7.26-7.38 (m, 5H), 8.30 (d, J=5.00 Hz, 1H).

HRMS (ESI) calcd for C25H28N5O3 [M+H]+ 446.2187. found 446.2169.

Step a (Method D)

2-(2-Amino-pyrimidin-4-yl)-3-(3-methoxy-phenyl)-1-methyl-1,5,6,7-tetrahydro-pyrrolo[3,2-c]pyridin-4-one trifluoroacetate

[(I), R1=3-methoxyphenyl, R2=H, R3=$NH_2$, R4=Me]

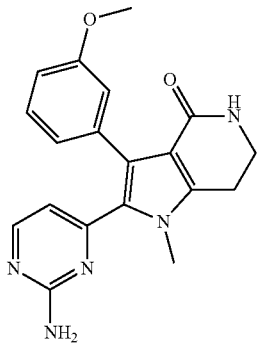 [SMILES: COc1cccc(-c2c3c(n(C)c2-c2ccnc(N)n2)CCNC3=O)c1]

To a solution of 2-(2-amino-pyrimidin-4-yl)-3-iodo-4-oxo-1,4,6,7-tetrahydro-pyrrolo-[3,2-c]pyridine-5-carboxylic acid tert-butyl ester (30 mg, 0.67 mmol) in dichloromethane (1 mL), trifluoroacetic acid was added (0.5 mL). The mixture was stirred until disappearance of the starting material. The solvent was evaporated to give 30 mg of 2-(2-Amino-pyrimidin-4-yl)-3-(3-methoxy-phenyl)-1,5,6,7-tetrahydro-pyrrolo[3,2-c]pyridin-4-one in quantitative yield.

HPLC (254 nm): Rt: 3.26 min.

$^1$H-NMR (401 MHz, DMSO-$d_6$) δ=2.94 (t, J=6.70 Hz, 2H), 3.45-3.48 (m, 2H), 3.71 (s, 3H), 3.80 (s, 3H), 5.95 (d, J=6.22 Hz, 1H), 6.75 (dd, J=7.90 and 2.68 Hz, 1H), 6.80-6.83 (m, 1H), 6.87 (dd, J=7.90 and 2.68 Hz, 1H), 7.11 (br. s., 1H), 7.21 (t, J=7.90 Hz, 1H), 7.71 (br. s., 2H), 7.93 (d, J=6.22 Hz, 1H).

HRMS (ESI) calcd for C19H20N5O2 [M+H]+ 350.1612. found 350.1609.

Operating in an analogous way the following compounds were obtained:

2-(2-Aminopyrimidin-4-yl)-1-methyl-3-phenyl-1,5,6,7-tetrahydro-4H-pyrrolo[3,2-c]pyridin-4-one hydrochloride

[(I), R1=phenyl, R2=H, R3=NH$_2$, R4=Me]

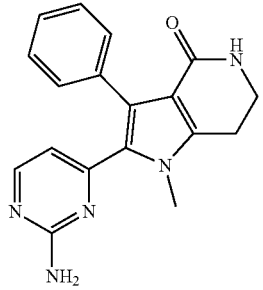 [SMILES: Cn1c2c(c(-c3ccccc3)c1-c1ccnc(N)n1)C(=O)NCC2]

HCl 4M in dioxane was used in the last step instead of trifluoroacetic acid.

HPLC (254 nm): Rt: 3.11 min.

$^1$H-NMR (401 MHz, DMSO-$d_6$) δ=7.90 (d, J=6.2 Hz, 1H), 7.18-7.35 (m, 5H), 7.11 (br. s., 2H), 5.87 (d, J=6.2 Hz, 1H), 3.80 (s, 3H), 3.35 (t, J=6.7 Hz, 2H), 2.94 ppm (t, J=6.8 Hz, 2H).

HRMS (ESI) calcd for C18H18N5O [M+H]+ 320.1506. found 320.1507.

2-(2-Amino-pyrimidin-4-yl)-3-(3-chloro-phenyl)-1-methyl-1,5,6,7-tetrahydro-pyrrolo[3,2-c]pyridin-4-one

[(I), R1=3-chlorophenyl, R2=H, R3=NH$_2$, R4=Me]

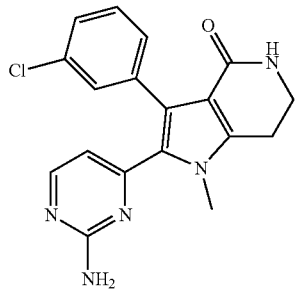 [SMILES: Cn1c2c(c(-c3cccc(Cl)c3)c1-c1ccnc(N)n1)C(=O)NCC2]

HCl 4M in dioxane was used in the last step instead of trifluoroacetic acid.

HPLC (254 nm): Rt: 3.56 min.

$^1$H-NMR (401 MHz, DMSO-$d_6$) δ=7.99 (d, J=5.9 Hz, 1H), 7.25-7.35 (m, 3H), 7.09-7.14 (m, 3H), 5.96 (d, J=5.9 Hz, 1H), 3.77 (s, 3H), 3.41 (m, 2H), 2.94 (t, J=6.8 Hz, 2H).

HRMS (ESI) calcd for C18H17ClN5O [M+H]+ 354.1116. found 354.1104.

3-(3-Amino-phenyl)-2-(2-amino-pyrimidin-4-yl)-1-methyl-1,5,6,7-tetrahydro-pyrrolo[3,2-c]pyridin-4-one hydrochloride

[(I), R1=3-aminophenyl, R2=H, R3=NH$_2$, R4=Me]

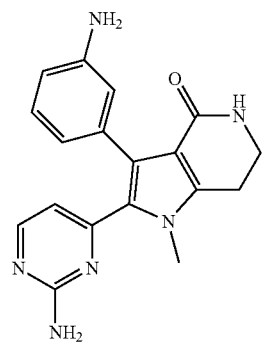

HCl 4M in dioxane was used in the last step instead of trifluoroacetic acid.

HPLC (254 nm): Rt: 2.87 min.

$^1$H-NMR (401 MHz, DMSO-$d_6$) δ=2.95 (t, J=6.75 Hz, 2H), 3.38-3.42 (m, 2H), 3.79 (s, 3H), 5.95 (d, J=6.22 Hz, 1H), 7.04-7.24 (m, 2H), 7.32-7.38 (m, 1H), 7.73 (br. s., 2H), 7.97 (d, J=6.22 Hz, 1H), 9.56 (br. s., 2H).

HRMS (ESI) calcd for C18H19N6O [M+H]+ 335.1615. found 335.1599.

2-(2-Amino-pyrimidin-4-yl)-3-(3-hydroxy-phenyl)-1-methyl-1,5,6,7-tetrahydro-pyrrolo[3,2-c]pyridin-4-one

[(I), R1=3-hydroxyphenyl, R2=H, R3=NH$_2$, R4=Me]

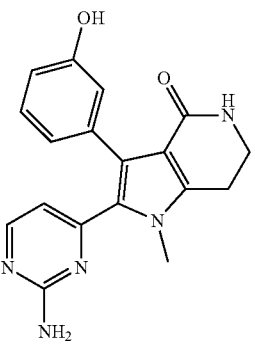 [SMILES: Cn1c2c(c(-c3cccc(O)c3)c1-c1ccnc(N)n1)C(=O)NCC2]

HPLC (254 nm): Rt: 3.72 min.

$^1$H-NMR (401 MHz, DMSO-$d_6$) δ=2.87 (t, J=6.75 Hz, 2H), 3.37-3.44 (m, 2H), 3.69 (s, 3H), 5.88 (d, J=5.12 Hz, 1H), 6.53-6.57 (m, 1H), 6.57-6.61 (m, 1H), 6.94 (br. s., 1H), 6.97-7.03 (m, 1H), 7.92 (d, J=5.12 Hz, 1H), 9.12 (s, 1H).

HRMS (ESI) calcd for C18H18N5O2 [M+H]+ 336.1455. found 336.1461.

2-(2-Amino-pyrimidin-4-yl)-1-methyl-3-((E)-styryl)-1,5,6,7-tetrahydro-pyrrolo[3,2-c]pyridin-4-one

[(I), R1=E-2-phenylethenyl, R2=H, R3=NH$_2$, R4=Me]

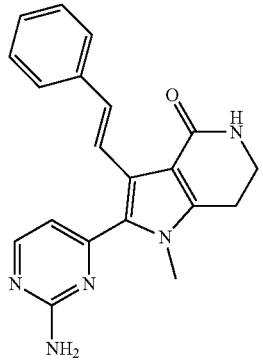 [SMILES: Cn1c2c(c(/C=C/c3ccccc3)c1-c1ccnc(N)n1)C(=O)NCC2]

HPLC (254 nm): Rt: 4.74 min.
$^1$H-NMR (401 MHz, DMSO-d$_6$) δ=2.91 (t, J=6.75 Hz, 2H), 3.48-3.54 (m, 2H), 3.70 (s, 3H), 6.95 (d, J=6.46 Hz, 1H), 7.21-7.28 (m, 2H), 7.31-7.35 (m, 2H), 7.38 (d, J=16.46 Hz, 1H), 7.42 (d, J=7.31 Hz, 2H), 7.47 (d, J=16.46 Hz, 1H), 7.96 (br. s., 2H), 8.27 (d, J=6.46 Hz, 1H).
HRMS (ESI) calcd for C20H20N5O [M+H]+ 346.1663. found 346.1652.

2-(2-Amino-pyrimidin-4-yl)-3-(4-methoxy-phenyl)-1-methyl-1,5,6,7-tetrahydro-pyrrolo[3,2-c]pyridin-4-one trifluoroacetate

[(I), R1=4-methoxyphenyl, R2=H, R3=NH$_2$, R4=Me]

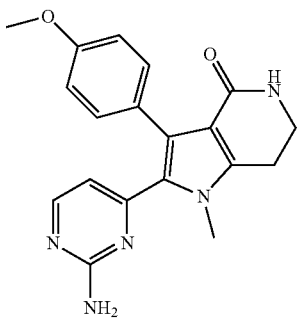 [SMILES: COc1ccc(-c2c3c(n(C)c2-c2ccnc(N)n2)CCNC3=O)cc1]

HPLC (254 nm): Rt: 3.26 min.
$^1$H-NMR (401 MHz, DMSO-d$_6$) δ=7.93 (d, J=6.3 Hz, 1H), 7.80 (br. s., 2H), 7.12-7.17 (m, 2H), 7.11 (br. s., 1H), 6.84-6.91 (m, 2H), 5.94 (d, J=6.3 Hz, 1H), 3.81 (s, 3H), 3.78 (s, 3H), 3.48 (br. s., 2H), 2.90-2.98 (m, 2H).
HRMS (ESI) calcd for C19H20N5O2 [M+H]+ 350.1612. found 350.1609.

2-(2-Amino-pyrimidin-4-yl)-3-(4-chlorophenyl)-1-methyl-1,5,6,7-tetrahydro-pyrrolo[3,2-c]pyridin-4-one trifluoroacetate

[(I), R1=4-chlorophenyl, R2=H, R3=NH$_2$, R4=Me]

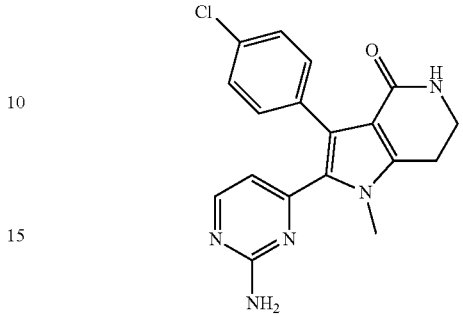

HPLC (254 nm): Rt: 3.63 min.
$^1$H-NMR (401 MHz, DMSO-d$_6$) δ=7.99 (d, J=5.9 Hz, 1H), 7.31-7.36 (m, 2H), 7.27-7.45 (br.s., 2H), 7.21-7.25 (m, 2H), 7.11 (br, s, 1H), 5.95 (d, J=5.9 Hz, 1H), 3.76 (s, 3H), 3.43 (br. s., 2H), 2.93 (t, J=6.8 Hz, 2H).
HRMS (ESI) calcd for C18H17ClN5O [M+H]+ 354.1116. found 354.1117.

Example 2

1-{3-[2-(2-Amino-pyrimidin-4-yl)-1-methyl-4-oxo-4,5,6,7-tetrahydro-1H-pyrrolo-[3,2-c]pyridin-3-yl]-phenyl}-3-(4-chloro-3-trifluoromethyl-phenyl)-urea

[(I), R1=3-[3-(4-chloro-3-trifluoromethylphenyl)-ureido]phenyl, R2=H, R3=NH$_2$, R4=Me]

The above compound was prepared according to Methods A and D as described below.

Preparation of 1-(4-chloro-3-trifluoromethyl-phenyl)-3-[3-(4,4,5,5-tetramethyl-[1,3,2]dioxaborolan-2-yl)-phenyl]-urea To a solution of 3-(4,4,5,5-Tetramethyl-[1,3,2]dioxaborolan-2-yl)-phenylamine (100 mg, 0.46 mmol) in dichloromethane (4 mL), 1-chloro-4-isocyanato-2-trifluoromethyl-benzene (100 mg, 0.46 mmol) was added. The mixture was stirred until disappearance of the starting material. The solvent was evaporated to dryness to give 200 mg of 1-(4-Chloro-3-trifluoromethyl-phenyl)-3-[3-(4,4,5,5-tetramethyl-[1,3,2]dioxaborolan-2-yl)-phenyl]urea in quantitative yield.

Step f (Method A)

2-(2-Amino-pyrimidin-4-yl)-3-{(3-[3-(4-chloro-3-trifluoro-methyl-phenyl)-ureido]-phenyl}-1-methyl-4-oxo-1,4,6,7-tetrahydro-pyrrolo[3,2-c]pyridine-5-carboxylic acid tert-butyl ester

[(II)f, L$_1$=direct bond, R4=Me, R5'=4-chloro-3-trifluoromethylphenyl, Q=Boc]

To a solution of 2-(2-amino-pyrimidin-4-yl)-3-iodo-4-oxo-1,4,6,7-tetrahydro-pyrrolo[3,2-c]pyridine-5-carboxylic acid tert-butyl ester (50 mg, 0.1 mmol) (prepared as described in Example 1) in toluene/EtOH 1:1 (2 mL), 1M aq Na2CO3 (0.25 mL, 0.25 mmol), LiCl (13 mg, 0.3 mmol), 1-(4-chloro-3-trifluoromethyl-phenyl)-3-[3-(4,4,5,5-tetramethyl-[1,3,2]dioxaborolan-2-yl)-phenyl]-urea (66 mg, 0.15 mmol) and (Ph3P)2PdCl2 (1.5 mg) were added and the mixture was stirred at 100° C. until disappearance of the starting material.

The solvent was evaporated and the crude was purified by flash chromatography (eluant: DCM/MeOH 95:5) to afford 20 mg of 2-(2-amino-pyrimidin-4-yl)-3-{3-[3-(4-chloro-3-trifluoro-methyl-phenyl)-ureido]-phenyl}-1-methyl-4-oxo-1,4,6,7-tetrahydro-pyrrolo[3,2-c]pyridine-5-carboxylic acid tert-butyl ester (30% yield) as a white powder.

HPLC (254 nm): Rt: 6.39 min.

¹H-NMR (401 MHz, DMSO-$d_6$) δ=1.42 (s, 9H), 2.99 (t, J=6.22 Hz, 2H), 3.70 (s, 3H), 4.00 (t, J=6.22 Hz, 2H), 5.91 (d, J=5.12 Hz, 1H), 6.62 (br. s., 2H), 6.77 (d, J=7.80 Hz, 1H), 7.18 (t, J=7.80 Hz, 1H), 7.22 (s, 1H), 7.43 (d, J=7.80 Hz, 1H), 7.56-7.66 (m, 2H), 7.96 (d, J=5.12 Hz, 1H), 8.06-8.10 (m, 1H), 8.78 (br. s., 1H), 9.04 (br. s., 1H).

HRMS (ESI) calcd for C31H30ClF3N7O4 [M+H]+ 656.1995. found 656.1982.

Step a (Method D)

1-{3-[2-(2-Amino-pyrimidin-4-yl)-1-methyl-4-oxo-4,5,6,7-tetrahydro-1H-pyrrolo-[3,2-c]pyridin-3-yl]-phenyl}-3-(4-chloro-3-trifluoromethyl-phenyl)-urea

[(I), R1=3-[3-(4-chloro-3-trifluoromethylphenyl)-ureido]phenyl, R2=H, R3=NH₂, R4=Me]

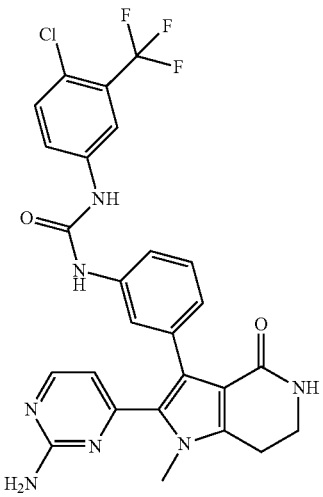 [SMILES: Cn1c2c(c(-c3cccc(NC(=O)Nc4ccc(Cl)c(C(F)(F)F)c4)c3)c1-c1ccnc(N)n1)C(=O)NCC2]

2-(2-amino-pyrimidin-4-yl)-3-{3-[3-(4-chloro-3-trifluoro-methyl-phenyl)-ureido]-phenyl}-1-methyl-4-oxo-1,4,6,7-tetrahydro-pyrrolo[3,2-c]pyridine-5-carboxylic acid tert-butyl ester (15 mg, 0.023 mmol) was dissolved in 4 N HCl solution in dioxane (2 mL). After stirring for 1 hour at room temperature the suspension was evaporated to dryness, obtaining the desired product as yellow solid (quant.)

HPLC (254 nm): Rt: 5.11 min.

¹H-NMR (401 MHz, DMSO-$d_6$) δ=2.96 (t, J=6.75 Hz, 2H), 3.45-3.51 (m, 2H), 3.84 (s, 3H), 5.98 (d, J=6.46 Hz, 1H), 6.84 (d, J=7.92 Hz, 1H), 7.15 (br. s., 1H), 7.23 (t, J=7.92 Hz, 1H), 7.33 (br. s., 1H), 7.45 (d, J=7.92 Hz, 1H), 7.57-7.66 (m, 2H), 7.94 (d, J=6.46 Hz, 1H), 8.08 (s, 1H), 9.09 (br. s., 1H), 9.40 (br. s., 1H).

HRMS (ESI) calcd for C26H22ClF3N7O2 [M+H]+ 556.147. found 556.1486.

Example 3

1-{3-[2-(2-Amino-pyrimidin-4-yl)-1-methyl-4-oxo-4,5,6,7-tetrahydro-1H-pyrrolo-[3,2-c]pyridin-3-yl]-phenyl}-3-(4-trifluoromethyl-phenyl)-urea (Cpd. no 1)

[(I), R1=3-[3-(4-trifluoromethylphenyl)-ureido]phenyl, R2=H, R3=NH₂, R4=Me]

The above compound was prepared according to Methods A and D as described below.

Step o (Method A)

2-(2-Amino-pyrimidin-4-yl)-1-methyl-4-oxo-3-{3-[3-(4-trifluoromethyl-phenyl)-ureido]-phenyl}-1,4,6,7-tetrahydro-pyrrolo[3,2-c]pyridine-5-carboxylic acid tert-butyl ester

[(II)f, L₁=direct bond, R4=Me, R5'=4-trifluoromethylphenyl, Q=Boc]

To a solution of 3-(3-amino-phenyl)-2-(2-amino-pyrimidin-4-yl)-1-methyl-4-oxo-1,4,6,7-tetrahydro-pyrrolo[3,2-c]pyridine-5-carboxylic acid tert-butyl ester (40 mg, 0.092 mmol) (prepared as described in Example 1) in dichloromethane (1 mL), 1-isocyanato-4-trifluoromethyl-benzene (0.014 mL, 0.101 mmol) was added. The mixture was stirred until disappearance of the starting material. The solvent was evaporated and the residued was suspended in diethylether and filtered to give 35 mg of 2-(2-Amino-pyrimidin-4-yl)-1-methyl-4-oxo-3-{3-[3-(4-trifluoromethyl-phenyl)-ureido]-phenyl}-1,4,6,7-tetrahydro-pyrrolo[3,2-c]pyridine-5-carboxylic acid tert-butyl ester. (y: 61%)

HPLC (254 nm): Rt: 5.76 min.

¹H-NMR (401 MHz, DMSO-$d_6$) δ=1.43 (s, 9H), 3.00 (t, J=6.24 Hz, 2H), 3.71 (s, 3H), 4.01 (t, J=6.24 Hz, 2H), 5.93 (d, J=5.12 Hz, 1H), 6.64 (br. s., 2H), 6.77 (d, J=6.58 Hz, 1H), 7.19 (d, J=7.92 Hz, 1H), 7.20-7.24 (m, 1H), 7.46 (d, J=7.92 Hz, 1H), 7.58-7.68 (m., 4H), 7.97 (d, J=5.12 Hz, 1H), 875 (br. s., 1H), 8.99 (br. s., 1H).

HRMS (ESI) calcd for C31H31F3N7O4 [M+H]+ 622.2384. found 622.2372.

Operating in analogous way the following Boc derivatives were obtained:

2-(2-Amino-pyrimidin-4-yl)-1-methyl-4-oxo-3-[3-(3-phenyl-ureido)-phenyl]-1,4,6,7-tetrahydro-pyrrolo[3,2-c]pyridine-5-carboxylic acid tert-butyl ester

[(II)f, L₁=direct bond, R4=Me, R5'=phenyl, Q=Boc]

HPLC (254 nm): Rt: 6.08 min.

¹H-NMR (401 MHz, DMSO-$d_6$) δ=1.43 (s, 9H), 3.00 (t, J=6.22 Hz, 2H), 3.71 (s, 3H), 4.01 (t, J=6.22 Hz, 2H), 5.95 (d, J=5.12 Hz, 1H), 6.63 (br. s., 2H), 6.74 (d, J=7.80 Hz, 1H), 6.92-6.99 (m, 1H), 7.17 (t, J=7.80 Hz, 1H), 7.19-7.21 (m, 1H), 7.24-7.31 (m, 2H), 7.39-7.44 (m, 3H), 7.97 (d, J=5.12 Hz, 1H), 8.55 (br. s., 1H), 8.60 (br. s., 1H).

HRMS (ESI) calcd for C30H32N7O4 [M+H]+ 554.2511. found 554.2504.

2-(2-Amino-pyrimidin-4-yl)-1-methyl-4-oxo-3-[3-(3-m-tolyl-ureido)-phenyl]-1,4,6,7-tetrahydro-pyrrolo[3,2-c]pyridine-5-carboxylic acid tert-butyl ester

[(II)f, L₁=direct bond, R4=Me, R5'=3-methylphenyl, Q=Boc]

HPLC (254 nm): Rt: 6.33 min.
¹H-NMR (401 MHz, DMSO-d₆) δ=1.43 (s, 9H), 2.27 (s, 3H), 3.00 (t, J=6.22 Hz, 2H), 3.71 (s, 3H), 4.01 (t, J=6.22 Hz, 2H), 5.93 (d, J=5.12 Hz, 1H), 6.63 (br. s., 2H), 6.70-6.76 (m, 1H), 6.78 (d, J=7.44 Hz, 1H), 7.11-7.24 (m., 4H), 7.28 (s, 1H), 7.44 (d, J=7.44 Hz, 1H), 7.97 (d, J=5.12 Hz, 1H), 8.47 (br. s., 1H), 8.59 (br. s., 1H).
HRMS (ESI) calcd for C31H34N7O4 [M+H]+ 568.2667. found 568.2657.

Step a (Method D)

1-{3-[2-(2-Amino-pyrimidin-4-yl)-1-methyl-4-oxo-4,5,6,7-tetrahydro-1H-pyrrolo[3,2-c]pyridin-3-yl]-phenyl}-3-(4-trifluoromethyl-phenyl)-urea

[(I), R1=3-[3-(4-trifluoromethylphenyl)-ureido]phenyl, R2=H, R3=NH₂, R4=Me]

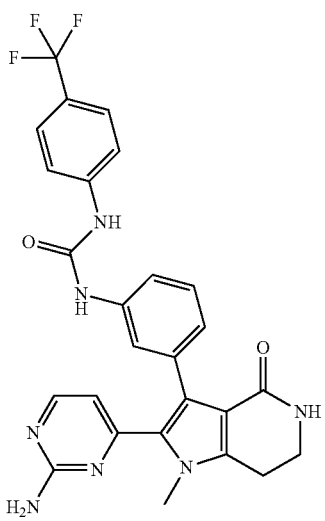 [SMILES: Cn1c2c(c(-c3cccc(NC(=O)Nc4ccc(C(F)(F)F)cc4)c3)c1-c1ccnc(N)n1)C(=O)NCC2]

2-(2-Amino-pyrimidin-4-yl)-1-methyl-4-oxo-3-{3-[3-(4-trifluoromethyl-phenyl)-ureido]-phenyl}-1,4,6,7-tetrahydro-pyrrolo[3,2-c]pyridine-5-carboxylic acid tert-butyl ester (15 mg, 0.024 mmol) was dissolved in 4 N HCl solution in dioxane (2 mL). After stirring for 1 hour at room temperature the suspension was evaporated to dryness, obtaining the desired product as yellow solid (quant.)
HPLC (254 nm): Rt: 5.50 min.
¹H-NMR (401 MHz, DMSO-d₆) δ=2.97 (t, J=6.75 Hz, 2H), 3.47-3.51 (m, 2H), 3.84 (s, 3H), 6.00 (d, J=6.46 Hz, 1H), 6.86 (dd, J=7.92 and 2.19 Hz, 1H), 7.17 (br. s., 1H), 7.24 (t, J=7.92 Hz, 1H), 7.33 (t, J=1.83 Hz, 1H) 7.43-7.49 (m., 1H), 7.62 (d, J=9.39 Hz, 2H), 7.65 (d, J=9.39 Hz, 2H), 7.96 (d, J=6.46 Hz, 1H), 8.01 (br. s., 1H), 9.06 (br. s., 1H), 9.30 (br. s., 1H).
HRMS (ESI) calcd for C26H23F3N7O2 [M+H]+ 522.1860. found 522.1864.

Operating in an analogous way the following compounds were prepared:

1-{3-[2-(2-Amino-pyrimidin-4-yl)-1-methyl-4-oxo-4,5,6,7-tetrahydro-1H-pyrrolo[3,2-c]pyridin-3-yl]-phenyl}-3-phenyl-urea

[(I), R1=3-[3-(phenyl)-ureido]phenyl, R2=H, R3=NH₂, R4=Me]

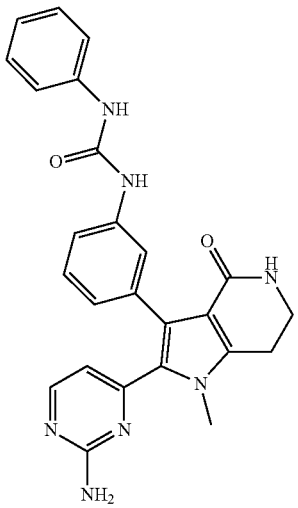 [SMILES: Cn1c2c(c(-c3cccc(NC(=O)Nc4ccccc4)c3)c1-c1ccnc(N)n1)C(=O)NCC2]

HPLC (254 nm): Rt: 4.65 min.
¹H-NMR (401 MHz, DMSO-d₆) δ=2.97 (t, J=6.75 Hz, 2H), 3.47-3.53 (m, 2H), 3.85 (s, 3H), 6.01 (d, J=6.58 Hz, 1H), 6.82 (d, J=7.80 Hz, 1H), 6.96 (t, J=7.32 Hz, 1H), 7.13 (br. s., 1H), 7.23 (t, J=7.80 Hz, 1H) 7.25-7.30 (m., 2H), 7.31-7.33 (m, 1H), 7.41-7.49 (m, 2H), 7.95 (d, J=6.58 Hz, 1H), 8.05 (br. s., 2H), 8.79 (br. s., 1H), 8.87 (br. s., 1H).
HRMS (ESI) calcd for C25H24N7O2 [M+H]+ 454.1986. found 454.1981.

1-{3-[2-(2-Amino-pyrimidin-4-yl)-1-methyl-4-oxo-4,5,6,7-tetrahydro-1H-pyrrolo[3,2-c]pyridin-3-yl]-phenyl}-3-m-tolyl-urea

[(I), R1=3-[3-(3-methylphenyl)-ureido]phenyl, R2=H, R3=NH₂, R4=Me]

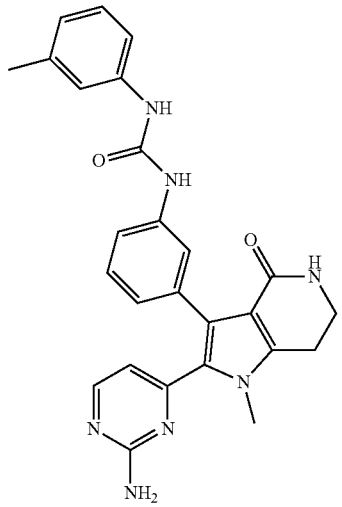 [SMILES: Cc1cccc(NC(=O)Nc2cccc(-c3c4c(n(C)c3-c3ccnc(N)n3)CCNC4=O)c2)c1]

HPLC (254 nm): Rt: 4.95 min.

$^1$H-NMR (401 MHz, DMSO-$d_6$) δ=2.27 (s, 3H), 2.97 (t, J=6.70 Hz, 2H), 3.47-3.52 (m, 2H), 3.86 (s, 3H), 6.01 (d, J=6.58 Hz, 1H), 6.78 (d, J=7.57 Hz, 1H), 6.81 (d, J=7.44 Hz, 1H), 7.14 (t, J=7.57 Hz, 1H), 7.18 (br. s., 1H), 7.20-7.29 (m., 2H), 7.33 (t, J=1.80 Hz, 1H), 7.44-7.88 (m, 2H), 7.95 (d, J=6.58 Hz, 1H), 8.09 (br. s., 2H), 8.79 (br. s., 1H), 8.94 (br. s., 1H).

HRMS (ESI) calcd for C26H26N7O2 [M+H]+ 468.2143. found 468.2145.

Example 4

N-{3-[2-(2-Amino-pyrimidin-4-yl)-1-methyl-4-oxo-4,5,6,7-tetrahydro-1H-pyrrolo[3,2-c]pyridin-3-yl]-phenyl}-3-fluoro-benzenesulfonamide

[(I), R1=3-(3-fluoro-benzenesulfonylamino)-phenyl, R2=H, R3=NH$_2$, R4=Me]

The above compound was prepared according to Methods A and D as described below.

Step k (Method A)

2-(2-amino-pyrimidin-4-yl)-3-[3-(3-fluoro-benzene-sulfonyl-amino)-phenyl]-1-methyl-4-oxo-1,4,6,7-tetrahydro-pyrrolo[3,2-c]pyridine-5-carboxylic acid tert-butyl ester

[(II)d, L$_1$=direct bond, R4=Me, R5'=3-fluorophenyl, Q=Boc]

To a solution of 3-(3-amino-phenyl)-2-(2-amino-pyrimidin-4-yl)-4-oxo-1,4,6,7-tetra-hydro-pyrrolo[3,2-c]pyridine-5-carboxylic acid tert-butyl ester (30 mg, 0.070 mmol) (prepared as described in Example 1) in dichloromethane (1 mL), 3-fluoro-benzene-sulfonyl chloride (0.010 mL, 0.077 mmol) and a drop of triethylamine were added. The mixture was stirred until disappearance of the starting material. The solvent was evaporated and the residued was suspended in diethylether and filtered to give 20 mg of 2-(2-amino-pyrimidin-4-yl)-3-[3-(3-fluoro-benzenesulfonylamino)-phenyl]-1-methyl-4-oxo-1,4,6,7-tetrahydro-pyrrolo[3,2-c]pyridine-5-carboxylic acid tert-butyl ester. (y: 50%)

HPLC (254 nm): Rt: 6.16 min.

$^1$H-NMR (401 MHz, DMSO-$d_6$) δ=1.43 (s, 9H), 2.96 (t, J=6.23 Hz, 2H), 3.69 (s, 3H), 3.99 (t, J=6.23 Hz, 2H), 3.79 (s, 3H), 5.61 (d, J=5.12 Hz, 1H), 6.65 (br. s., 2H), 6.81 (d, J=7.80 Hz, 1H), 6.94-6.99 (m, 1H), 7.00-7.03 (m, 1H), 7.13 (t, J=7.80 Hz, 1H), 7.44-7.63 (m, 4H), 7.82 (d, J=5.12 Hz, 1H), 10.25 (s, 1H).

HRMS (ESI) calcd for C29H30FN6O5S [M+H]+ 593.1977. found 593.1964.

Step a (Method D)

N-{3-[2-(2-Amino-pyrimidin-4-yl)-1-methyl-4-oxo-4,5,6,7-tetrahydro-1H-pyrrolo[3,2-c]pyridin-3-yl]-phenyl}-3-fluoro-benzenesulfonamide

[(I), R1=3-(3-fluoro-benzenesulfonylamino)-phenyl, R2=H, R3=NH$_2$, R4=Me]

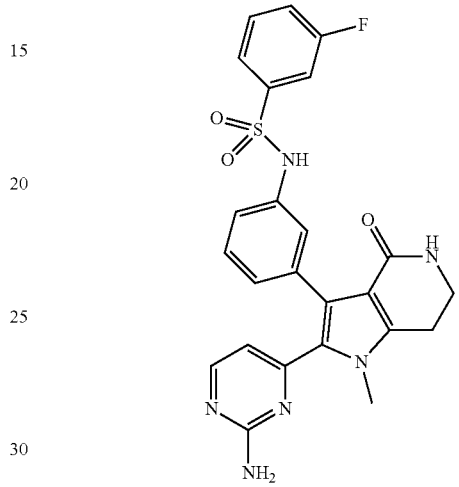

2-(2-amino-pyrimidin-4-yl)-3-[3-(3-fluoro-benzenesulfonylamino)-phenyl]-1-methyl-4-oxo-1,4,6,7-tetrahydro-pyrrolo[3,2-c]pyridine-5-carboxylic acid tert-butyl ester (20 mg, 0.034 mmol) was dissolved in 4 N HCl solution in dioxane (2 mL). After stirring for 1 hour at room temperature the suspension was evaporated to dryness, obtaining the desired product as yellow solid (quant.)

HPLC (254 nm): Rt: 4.70 min.

$^1$H-NMR (401 MHz, DMSO-$d_6$) δ=2.94 (t, J=6.75 Hz, 2H), 3.43-3.52 (m, 2H), 3.79 (s, 3H), 5.68 (d, J=6.34 Hz, 1H), 6.94 (d, J=7.80 Hz, 1H), 6.97-6.99 (m, 1H), 6.99-7.03 (m, 1H), 7.14 (br. s., 1H), 7.19 (t, J=7.80 Hz, 1H), 7.45-7.63 (m, 4H), 7.69 (d, J=6.34 Hz, 1H), 8.02 (br, s., 2H).

HRMS (ESI) calcd for C24H22FN6O3S [M+H]+ 493.1453. found 493.1464.

Example 5

Thiophene-2-carboxylic acid 3-[2-(2-amino-pyrimidin-4-yl)-1-methyl-4-oxo-4,5,6,7-tetrahydro-1H-pyrrolo[3,2-c]pyridin-3-yl]-phenyl ester

[(I), R1=3-(thiophene-2-carbonyloxy)-phenyl, R2=H, R3=NH$_2$, R4=Me]

The above compound was prepared according to Methods A and D as described below.

Step s (Method A)

2-(2-Amino-pyrimidin-4-yl)-1-methyl-4-oxo-3-[3-(thiophene-2-carbonyloxy)-phenyl]-1,4,6,7-tetrahydro-pyrrolo[3,2-c]pyridine-5-carboxylic acid tert-butyl ester

[(II)j, L₁=direct bond, R4=Me, R5'=2-thiophenyl, Q=Boc]

To a solution of 2-(2-amino-pyrimidin-4-yl)-3-(3-hydroxy-phenyl)-1-methyl-4-oxo-1,4,6,7-tetrahydro-pyrrolo[3,2-c]pyridine-5-carboxylic acid tert-butyl ester (108 mg, 0.234 mmol) (prepared as described in Example 1) in dry THF (2.3 mL) under argon atmosphere 2-thiophene-carbonylchloride (0.026 mL, 0.234 mmol, 1 eq) and DIPEA (0.061 mL, 0.350 mmol, 1.5 eq.) were added. After stirring for 3 h at room temperature the solvent was evaporated. The product was crystallized by refluxing in ethyl acetate/diethyl ether mixture and cooling slowly to room temperature affording 74 mg of white solid in 56% yield.

HPLC (254 nm): Rt: 6.56 min.

¹H-NMR (401 MHz, DMSO-d₆) δ=1.43 (s, 9H), 3.00 (t, 2H, J=6.1 Hz), 3.70 (s, 3H), 4.01 (t, 2H, J=6.1 Hz), 5.96 (d, 1H, J=5.1 Hz), 6.72 (bs, 2H), 7.08 (m, 2H), 7.19 (m, 1H), 7.30 (dd, 1H, J=4.8 Hz), 7.36 (m, 1H), 8.01 (m, 2H), 8.08 (dd, 1H, J=5.0 and 1.2 Hz).

HRMS (ESI) calcd for C28H28N5O5S [M+H]+ 546.1806. found 546.1796.

Step a (Method D)

Thiophene-2-carboxylic acid 3-[2-(2-amino-pyrimidin-4-yl)-1-methyl-4-oxo-4,5,6,7-tetrahydro-1H-pyrrolo[3,2-c]pyridin-3-yl]-phenyl ester

[(I), R1=3-(thiophene-2-carbonyloxy)-phenyl, R2=H, R3=NH₂, R4=Me]

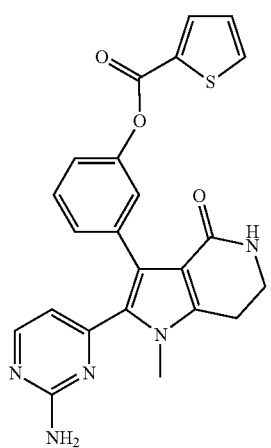 [SMILES: Cn1c2c(c(-c3cccc(OC(=O)c4cccs4)c3)c1-c1ccnc(N)n1)C(=O)NCC2]

2-(2-Amino-pyrimidin-4-yl)-1-methyl-4-oxo-3-[3-(thiophene-2-carbonyloxy)-phenyl]-1,4,6,7-tetrahydro-pyrrolo[3,2-c]pyridine-5-carboxylic acid tert-butyl ester (74 mg, 0.136 mmol) was dissolved in 1 ml of dioxane and treated with 10 equivalents of HCl 4 M in dioxane at room temperature. After 2 h the suspension has been evaporated and the residue crushed with diethyl ether filtered-off and dried giving the desired product as a yellow solid.

HPLC (254 nm): Rt: 4.98 min.

¹H-NMR (401 MHz, DMSO-d₆) δ=2.96 (t, 2H, J=6.7 Hz), 3.38 (t, 2H, J=6.7 Hz), 3.81 (s, 3H), 5.99 (d, 1H, J=6.2 Hz), 7.16-7.23 (m, 3H), 7.31 (dd, 1H, J=5.0 Hz), 7.39 (t, 1H, J=7.8 Hz), 7.75 (bs, 1H), 7.99 (d, 1H, J=6.2 Hz), 8.01 (m, 1H), 8.09 (dd, 1H, J=5.0 and 1.3 Hz).

HRMS (ESI) calcd for C23H21N5O3S [M+H]+ 446.1282. found: 446.1303.

Example 6

3-(3-Amino-benzyl)-2-(2-amino-pyrimidin-4-yl)-1-methyl-1,5,6,7-tetrahydro-pyrrolo[3,2c]pyridin-4-one hydrochloride

[(I), R1=3-amino-benzyl, R2=H, R3=NH₂, R4=Me]

The above compound was prepared according to Methods A and D as described below.

Preparation of 3-nitro-benzyl tributyl stannane

A solution of 1-Bromomethyl-3-nitro-benzene (3.90 g, 18.05 mmol), hexabutylditin (14.14 g, 24.37 mmol), palladium tetrakis(triphenylphosphine) (0.209 g, 0.181 mmol), in dry toluene (100 ml), was refluxed under argon for 24 h. The reaction mixture was washed with an aqueous solution of KF (20%), (2×50.0 ml) and the organic phase was dried over Na₂SO₄, filtered and the solvent was removed under vacuum. The crude was purified over silica (Hexane/Etylacetate 95:5) affording the desired 3-nitro-benzyl tributyl stannane.

Step h (Method A)

2-(2-Amino-pyrimidin-4-yl)-1-methyl-3-(3-nitro-benzyl)-4-oxo-1,4,6,7-tetrahydro-pyrrolo[3,2-c]pyridine-5-carboxylic acid tert-butyl ester

[14, L₁=CH₂, Q=Boc, R4=Me]

Cesium fluoride (0.048 g, 0.320 mmol), palladium tetrakis(triphenylphosphine) (0.018 g, 0.016 mmol) and CuI (0.0060 g, 0.032 mmol) were added to a solution of 2-(2-amino-pyrimidin-4-yl)-3-iodo-1-methyl-4-oxo-1,4,6,7-tetrahydro-pyrrolo[3,2-c]-pyridine-5-carboxylic acid tert-butyl ester (prepared as described in Example 1) (0.075 g, 0.160 mmol) and 3-nitro-benzyl tributyl stannane (0.102 g, 0.240 mmol) in dry DMF (1.5 ml) under an argon atmosphere. The reaction mixture was stirred at 120° C. under microwave irradiation for 1 h. The reaction mixture was diluted with purite water (2.0 ml) and the precipitate was filtered, dissolved into DCM and purified on silica gel (DCM/MeOH from 100:0 up to 85:15), affording 2-(2-Amino-pyrimidin-4-yl)-1-methyl-3-(3-nitro-benzyl)-4-oxo-1,4,6,7-tetrahydro-pyrrolo[3,2-c]pyridine-5-carboxylic acid tert-butyl ester (0.0558 g, 0.116 mmol, 73%).

HPLC (254 nm): R_t: 6.21 min.

¹H NMR (401 MHz, DMSO-d₆) δ=8.40-8.17 (m, 1H), 8.03-7.91 (m, 2H), 7.68-7.48 (m, 2H), 6.65 (br. s., 2H), 6.51 (d, J=4.5 Hz, 1H), 4.36 (s, 2H), 3.96 (t, J=6.3 Hz, 2H), 3.64 (s, 3H), 2.97 (t, J=6.3 Hz, 2H), 1.45 (s, 9H).

HRMS (ESI) calcd for C₂₄H₂₆N₆O₅ [M+H]+ 479.2038. found 479.2044.

Step j (Method A)

3-(3-Amino-benzyl)-2-(2-amino-pyrimidin-4-yl)-1-methyl-4-oxo-1,4,6,7-tetrahydro-pyrrolo[3,2-c]pyridine-5-carboxylic acid tert-butyl ester

[(II)c, L$_1$=—CH$_2$—, R4=Me, Q=Boc]

Zn (0.041 g, 0.632 mmol) and ammonium chloride (0.034 g, 1.58 mmol) were added to a solution of 2-(2-Amino-pyrimidin-4-yl)-1-methyl-3-(3-nitro-benzyl)-4-oxo-1,4,6,7-tetrahydro-pyrrolo[3,2-c]pyridine-5-carboxylic acid tert-butyl ester (0.075 g, 0.158 mmol) was dissolved in dioxane (5 ml) and purite water (1.0 ml) and the reaction mixture was stirred at 75° C. for 2 hours. A solution of Na$_2$HPO$_4$ (10 ml) was then added and the water layer was extracted with EtOAc (3×10 ml). The organic layers were dried over Na$_2$SO$_4$, filtered, and the solvent was removed under reduced pressure yielding 3-(3-Amino-benzyl)-2-(2-amino-pyrimidin-4-yl)-1-methyl-4-oxo-1,4,6,7-tetrahydro-pyrrolo-[3,2-c]pyridine-5-carboxylic acid tert-butyl ester (0.071 g, 0.158 mmol, 100%).

HPLC (254 nm): R$_t$: 5.41 min.

$^1$H NMR (401 MHz, DMSO-d$_6$) δ=8.21-8.17 (m, 1H), 6.98-6.89 (m, 2H), 6.66 (s, 2H), 6.53-6.36 (m, 5H), 4.10 (s, 2H), 4.0-3.92 (m, 2H), 3.66 (s, 3H), 3.02 (m, 2H), 1.45 (s, 9H).

HRMS (ESI) calcd for C$_{24}$H$_{28}$N$_6$O$_3$ [M+H]$^+$ 449.2296. found 449.2311.

Step a (Method D)

3-(3-Amino-benzyl)-2-(2-amino-pyrimidin-4-yl)-1-methyl-1,5,6,7-tetrahydro-pyrrolo[3,2-c]pyridin-4-one hydrochloride

[(I), R1=3-amino-benzyl, R2=H, R3=NH$_2$, R4=Me]

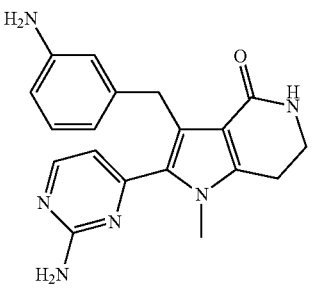 [SMILES: Cn1c2c(c(Cc3cccc(N)c3)c1-c1ccnc(N)n1)C(=O)NCC2]

A suspension of 3-(3-Amino-benzyl)-2-(2-amino-pyrimidin-4-yl)-1-methyl-4-oxo-1,4,6,7-tetrahydro-pyrrolo[3,2-c]pyridine-5-carboxylic acid tert-butyl ester (0.030 g, 0.066 mmol) in 4 N HCl in dioxane (2 ml) was stirred at room temperature for 1 h. The solvent was removed under vacuum, affording 3-(3-Amino-benzyl)-2-(2-amino-pyrimidin-4-yl)-1-methyl-1,5,6,7-tetrahydro-pyrrolo[3,2-c]pyridin-4-one hydrochloride (0.028 g, 0.062 mmol, 100%).

HPLC (254 nm): R$_t$: 3.75 min.

$^1$H-NMR (401 MHz, DMSO-d$_6$) δ=10.24-9.23 (br.s, 2H), 8.23 (d, J=6.2 Hz, 1H), 7.75 (br. s., 1H), 7.29 (t, J=7.8 Hz, 1H), 7.17 (br. s., 1H), 7.09 (d, J=8.4 Hz, 1H), 7.05 (s, 1H), 7.04 (d, J=7.2 Hz, 1H), 6.69 (d, J=6.2 Hz, 1H), 4.42 (s, 2H), 3.73 (s, 3H), 3.39 (m, 2H), 2.91 (t, J=6.8 Hz, 2H).

HRMS (ESI) calcd for C$_{16}$H$_{20}$N$_6$O [M+H]$^+$ 349.1772. found 349.1757.

Operating in an analogous way the following compound was prepared:

2-(2-Amino-pyrimidin-4-yl)-3-benzyl-1-methyl-1,5,6,7-tetrahydro-pyrrolo[3,2-c]pyridin-4-one

[(I), R1=benzyl, R2=H, R3=NH$_2$, R4=Me]

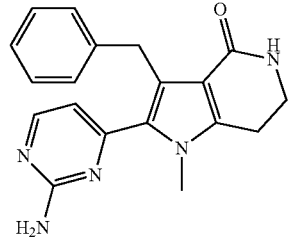 [SMILES: Cn1c2c(c(Cc3ccccc3)c1-c1ccnc(N)n1)C(=O)NCC2]

HPLC (254 nm): R$_t$: 4.44 min.

$^1$H-NMR (401 MHz, DMSO-d$_6$) δ=2.85 (t, J=6.83 Hz, 2H), 3.40 (td, J=6.83 and 2.84 Hz, 2H), 3.65 (s, 3H), 4.27 (s, 2H), 6.47 (d, J=5.24 Hz, 1H), 6.67 (br. s., 2H), 6.97 (br. s., 1H), 7.03-7.10 (m, 3H), 7.16 (d, J=7.46 Hz, 2H), 8.15 (d, J=5.24 Hz, 1H).

HRMS (ESI) calcd for C$_{19}$H$_{19}$N$_5$O [M+H]$^+$ 334.1663. found 334.1672.

Example 7

1-{3-[2-(2-Amino-pyrimidin-4-yl)-1-methyl-4-oxo-4,5,6,7-tetrahydro-1H-pyrrolo-[3,2-c]pyridin-3-ylmethyl]-phenyl}-3-(4-trifluoromethyl-phenyl)urea

[(I), R1=3-[3-(4-trifluoromethylphenyl)-ureido]phenylmethyl, R2=H, R3=NH$_2$, R4=Me]

The above compound was prepared according to Methods A and D as described below.

Step o (Method A): 2-(2-Amino-pyrimidin-4-yl)-1-methyl-4-oxo-3-{3-[3-(4-trifluoromethyl-phenyl)-ureido]-benzyl}-1,4,6,7-tetrahydro-pyrrolo[3,2-c]pyridine-5-carboxylic acid tert-butyl ester

[(II)f, L1=CH2, Q=Boc, R4=Me, R5'=4-trifluoromethylphenyl]

4-Trifluoromethyl-phenyl isocyanide (0.018 g, 0.096 mmol) was added to a solution of 3-(3-Amino-benzyl)-2-(2-amino-pyrimidin-4-yl)-1-methyl-4-oxo-1,4,6,7-tetrahydro-pyrrolo[3,2-c]pyridine-5-carboxylic acid tert-butyl ester (0.039 g, 0.088 mmol) (prepared as described in Example 6) in DCM (2.0 ml) and the reaction mixture was stirred at room temperature for 3 h, under an argon atmosphere. MTBE (5.0 ml) was added to the reaction mixture and the organic layer was washed with purite water (1×5.0 ml), brine (1×5.0 ml), dried over Na$_2$SO$_4$. The filtrate was dried under vacuum and the crude was purified by reverse phase chromatography, affording 2-(2-Amino-pyrimidin-4-yl)-1-methyl-4-oxo-3-{3-[3-(4-trifluoromethyl-phenyl)-ureido]-benzyl}-1,4,6,7-tetrahydro-pyrrolo[3,2-c]pyridine-5-carboxylic acid tert-butyl ester (0.051 g, 0.080 mmol, 93%).

HPLC (254 nm): R$_t$: 5.90 min.

$^1$H NMR (401 MHz, DMSO-d$_6$) δ=8.98 (s, 1H), 8.67 (s, 1H), 8.22 (d, J=5.1 Hz, 1H), 7.57-7.69 (m, 4H), 7.35 (dd, J=1.2, 8.1 Hz, 1H), 7.04-7.17 (m, 2H), 6.71 (d, J=8.0 Hz, 1H), 6.64 (s, 2H), 6.47 (d, J=5.1 Hz, 1H), 4.19 (s, 2H), 3.98 (t, J=6.3 Hz, 2H), 3.67 (s, 3H), 2.97 (t, J=6.2 Hz, 2H), 1.45 (s, 9H).

HRMS (ESI) calcd for C$_{32}$H$_{32}$F$_3$N$_7$O$_4$ [M+H]$^+$ 636.2541. found 636.2535.

Step a (Method D)

1-{3-[2-(2-Amino-pyrimidin-4-yl)-1-methyl-4-oxo-4,5,6,7-tetrahydro-1H-pyrrolo[3,2-c]pyridin-3-ylmethyl]-phenyl}-3-(4-trifluoromethyl-phenyl)urea

[(I), R1=3-[3-(4-trifluoromethylphenyl)-ureido]phenylmethyl, R2=H, R3=$NH_2$, R4=Me]

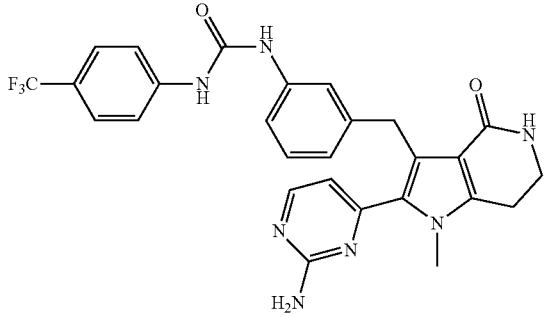 [SMILES: Cn1c2c(c(Cc3cccc(NC(=O)Nc4ccc(C(F)(F)F)cc4)c3)c1-c1ccnc(N)n1)C(=O)NCC2]

A suspension of 2-(2-Amino-pyrimidin-4-yl)-1-methyl-4-oxo-3-{3-[3-(4-trifluoro-methyl-phenyl)-ureido]-benzyl}-1,4,6,7-tetrahydro-pyrrolo[3,2-c]pyridine-5-carboxylic acid tert-butyl ester (0.020 g, 0.031 mmol) in HCl 4M/dioxane (1.0 ml) was stirred at room temperature for 1 h. The solvent was removed under vacuum, yielding 1-{3-[2-(2-Amino-pyrimidin-4-yl)-1-methyl-4-oxo-4,5,6,7-tetrahydro-1H-pyrrolo[3,2-c]pyridin-3-ylmethyl]-phenyl}-3-(4-trifluoromethyl-phenyl)urea (0.016 g, 0.0.29 mmol, 95%).

HPLC (254 nm): $R_t$: 4.62 min.
$^1$H NMR (401 MHz, DMSO-$d_6$) δ=9.21 (s, 1H), 8.85 (s, 1H), 8.23 (d, J=6.5 Hz, 1H), 7.86 (br. s., 2H), 7.64 (br.s., 4H), 7.27 (d, J=8.2 Hz, 1H), 7.19 (s, 1H), 7.12 (t, J=7.8 Hz, 1H), 6.85-6.73 (m, 2H), 4.42 (s, 2H), 3.76 (s, 3H), 3.39 (m, 2H), 2.93 (t, J=6.8 Hz, 2H).

HRMS (ESI) calcd for $C_{27}H_{24}F_3N_7O_2$ $[M+H]^+$ 536.2017. found 536.2015.

Example 8

2-(2-Amino-pyrimidin-4-yl)-3-(3-hydroxy-phenylamino)-1-methyl-1,5,6,7-tetrahydro-pyrrolo[3,2-c]pyridine-4-one

[(I), R1=3-hydroxyphenylamino, R2=H, R3=$NH_2$, R4=Me]

The above compound was prepared according to Method A as described below,

2-[2-(1,3-Dioxo-1,3-dihydro-isoindol-2-yl)-pyrimidin-4-yl]-3-iodo-1-methyl-4-oxo-1,4,6,7-tetrahydro-pyrrolo[3,2-c]pyridine-5-carboxylic acid tert-butyl ester Pthaloyl chloride (0.089 g, 0.437 mmol) was added to a cold (0° C.) solution of 2-(2-Amino-pyrimidin-4-yl)-3-iodo-1-methyl-4-oxo-1,4,6,7-tetrahydro-pyrrolo[3,2-c]-pyridine-5-carboxylic acid tert-butyl ester (prepared as described in Example 1) (0.158 g, 0.337 mmol) and pyridine (0.069 g, 0.875 mmol) in dry DCM (1.5 ml) and the reaction mixture was stirred at room temperature in argon atmosphere for 4 h. The organic layer was washed with a saturated solution of $NaHCO_3$ (1×2.0 ml), brine (1×2.0 ml), and it was dried over $Na_2SO_4$. The filtrate was evaporated to dryness to give the crude product, which was purified by flash chromatography, over silica gel (DCM/MeOH (9.8:0.2) as eluent), to afford 2-[2-(1,3-dioxo-1,3-dihydro-isoindol-2-yl)-pyrimidin-4-yl]-3-iodo-1-methyl-4-oxo-1,4,6,7-tetra-hydro-pyrrolo[3,2-c]pyridine-5-carboxylic acid tert-butyl ester (0.150 mg, 0.25 mmol, 74%).

HPLC (254 nm): $R_t$: 6.71 min.
$^1$H NMR (401 MHz, DMSO-$d_6$) δ=9.14 (d, J=5.2 Hz, 1H), 7.94-8.08 (m, 5H), 3.98 (t, J=6.3 Hz, 2H), 3.76 (s, 3H), 3.02 (t, J=6.3 Hz, 2H), 1.49 (s, 9H).

HRMS (ESI) calcd for $C_{25}H_{22}IN_5O_5$ $[M+H]+^+$ 600.0739. found 600.0732.

Step e (Method A): 2-(2-Amino-pyrimidin-4-yl)-3-(3-methoxy-phenylamino)-1-methyl-4-oxo-1,4,6,7-tetrahydro-pyrrolo[3,2-c]pyridine-5-carboxylic acid tert-butyl ester

[(II)z, PG=Me, $L_1$=—NH—, R4=Me, Q=Boc]

Cesium carbonate (0.154 g, 0.473 mmol), 4,5-bis(diphenylphoshino)-9,9-dimethylxanthene (0.027 g, 0.047 mmol), $Pd_2(dba)_3$ (0.0217 g, 0.023 mmol), 3-methoxy-phenylamine (0.038 g, 0.308 mmol) were added under argon to a solution of 2-[2-(1,3-Dioxo-1,3-dihydro-isoindol-2-yl)-pyrimidin-4-yl]-3-iodo-1-methyl-4-oxo-1,4,6,7-tetrahydro-pyrrolo[3,2-c]pyridine-5-carboxylic acid tert-butyl ester (0.142 mg, 0.237 mmol) in dry dioxane (4.0 ml) and the reaction mixture was stirred at 100° C. for 24 h under argon atmosphere. The solvent was removed under vacuum, the residue was taken up into DCM (5.0 ml), filtered, and the organic layer was washed with purite water (1×5.0 ml), dried over $Na_2SO_4$. The filtrate was purified over silica, using DCM/MeOH (9.5:0.5) as eluent, affording 2-(2-Amino-pyrimidin-4-yl)-3-(3-methoxy-phenylamino)-1-methyl-4-oxo-1,4,6,7-tetrahydro-pyrrolo[3,2-c]pyridine-5-carboxylic acid tert-butyl ester (0.025 g, 0.053 mmol, 23%).

HPLC (254 nm): $R_t$: 6.04 min.
$^1$H NMR (401 MHz, DMSO-$d_6$) δ=8.04 (d, J=5.2 Hz, 1H), 7.81 (s, 1H), 6.97-6.85 (m, 1H), 6.61 (d, J=5.2 Hz, 1H), 6.58 (br. s., 2H), 6.29-6.16 (m, 3H), 3.97 (t, J=6.2 Hz, 2H), 3.79 (s, 3H), 3.58 (s, 3H), 2.97 (t, J=6.2 Hz, 2H), 1.44 (s, 9H).

HRMS (ESI) calcd for $C_{24}H_{28}N_6O_4$ $[M+H]^+$ 465.2245. found 465.2245.

Step r (Method A): 2-(2-Amino-pyrimidin-4-yl)-3-(3-hydroxy-phenylamino)-1-methyl-1,5,6,7-tetrahydro-pyrrolo[3,2-c]pyridine-4-one

[(I), R1=3-hydroxyphenylamino, R2=H, R3=$NH_2$, R4=Me]

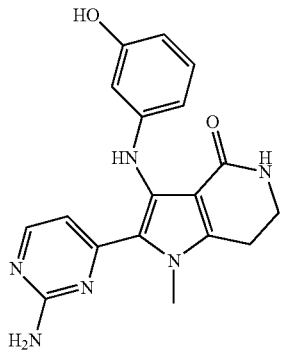

$BBr_3$ (0.860 g, 0.538 mmol) was added to a solution of 2-(2-Amino-pyrimidin-4-yl)-3-(3-methoxy-phenylamino)-1-methyl-4-oxo-1,4,6,7-tetrahydro-pyrrolo[3,2-c]pyridine-5-carboxylic acid tert-butyl ester (0.025 g, 0.054 mmol) in dry DCM (2 ml) at 0° C. and the reaction mixture was stirred at room temperature for 6 h. Purite water (5 ml) was added to the reaction vessel, the pH was adjusted to 7 and the water layer was extracted with DCM (3×5.0 ml), EtOAc (3×5.0 ml). The organic layers were combined, dried ($Na_2SO_4$), and the solvent was removed under vacuum, affording the pure product (0.0015 g, 0.004 mmol, 8%).

HPLC (254 nm): $R_t$: 3.78 min.

$^1$H NMR (401 MHz, DMSO-$d_6$) δ=8.91 (br. s., 1H), 7.99 (d, J=5.2 Hz, 1H), 7.49 (d, J=5.9 Hz, 1H), 7.08 (br. s., 1H), 6.79 (t, J=7.7 Hz, 1H), 6.64 (d, J=5.4 Hz, 1H), 6.47 (s, 2H), 6.17-5.93 (m, 3H), 3.84 (s, 3H), 3.48-3.37 (m, 2H), 2.87 (t, J=6.8 Hz, 2H).

HRMS (ESI) calcd for $C_{18}H_{18}N_6O_2$ [M+H]$^+$ 351.1564. found 351.1554.

Example 9

2-[2-Amino-5-(3-hydroxy-phenylethynyl)-pyrimidin-4-yl]-1-methyl-1,5,6,7-tetrahydro-pyrrolo[3,2-c]pyridin-4-one (Cpd. no 2)

[(I), R1=H, R2=3-hydroxyphenylethynyl, R3=NH$_2$, R4=Me]

The above compound was prepared according to Methods B and D as described below.

Step a (Method B)

2-(2-Amino-pyrimidin-4-yl)-1-methyl-4-oxo-1,4,6,7-tetrahydro-pyrrolo[3,2-c]pyridine-5-carboxylic acid tert-butyl ester

[(16), R4=Me, Q=Boc]

2-(2-Amino-pyrimidin-4-yl)-4-oxo-1,4,6,7-tetrahydro-pyrrolo[3,2-c]pyridine-5-carboxylic acid tert-butyl ester [(1), Q=Boc] (2 g, 6.07 mmol) was dissolved in dry DMF (70 mL) under nitrogen atmosphere. Cesium carbonate (2.37 g, 7.29 mmol, 1.2 eq) was added followed by methyl iodide (0.415 mL, 6.68 mmol, 1.1 eq) and the mixture was stirred at room temperature for 2 hours. The reaction mixture was then concentrated to small volume, diluted with ethyl acetate (70 mL) and washed with water (3×30 mL), dried over Na$_2$SO$_4$ and evaporated to dryness. The crude product was purified by flash chromatography on silica gel (DCM/MeOH 95/5) to obtain 1.75 g (84%) of the desired product as a white solid.

HPLC (254 nm): $R_t$: 5.09 min.

$^1$H NMR (401 MHz, DMSO-$d_6$) δ=8.17 (d, J=5.4 Hz, 1H), 7.10 (s, 1H), 6.91 (d, J=5.4 Hz, 1H), 6.58 (s, 2H), 3.98 (t, J=6.3 Hz, 2H), 3.94 (s, 3H), 2.96 (t, J=6.3 Hz, 2H), 1.48 (s, 9H).

HRMS (ESI) calcd for C17H22N5O3 [M+H]+ 344.1717. found 344.1707.

Step b (Method B)

2-(2-Amino-5-iodo-pyrimidin-4-yl)-1-methyl-4-oxo-1,4,6,7-tetrahydro-pyrrolo[3,2-c]pyridine-5-carboxylic acid tert-butyl ester

[(17), R4=Me, Q=Boc]

2-(2-Amino-pyrimidin-4-yl)-1-methyl-4-oxo-1,4,6,7-tetrahydro-pyrrolo[3,2-c]pyridine-5-carboxylic acid tert-butyl ester (1 g, 2.91 mmol) was dissolved in dry DMF (30 mL) under nitrogen atmosphere and the solution was cooled to 0° C. Silver trifluoroacetate (643 mg, 2.91 mmol, 1 eq) was added, followed by iodine (740 mg, 2.91 mmol, 1 eq) and the mixture was stirred at 0° C. for 1.5 hours. The silver salts were then filtered on a Celite pad and the Celite was thoroughly washed with ethyl acetate. The filtered solution was evaporated to dryness and the crude product was purified by flash chromatography on silica gel (DCM/EtOH 96:4) to give 840 mg of desired product as a pale yellow solid (62%).

HPLC (254 nm): $R_t$: 4.82 min.

$^1$H-NMR (401 MHz, DMSO-$d_6$) δ=8.57 (s, 1H), 7.02 (s, 1H), 6.87 (s, 2H), 3.99 (t, J=6.3 Hz, 2H), 3.62 (s, 3H), 2.98 (t, J=6.3 Hz, 2H), 1.48 (s, 9H).

HRMS (ESI) calcd for C17H21IN5O3 [M+H]+ 470.0684. found 470.0703.

Step d (Method B): 2-[2-Amino-5-(3-hydroxy-phenylethynyl)-pyrimidin-4-yl]-1-methyl-4-oxo-1,4,6,7-tetrahydro-pyrrolo[3,2-c]pyridine-5-carboxylic acid tert-butyl ester

[(II)s, L2'=C≡C, Q=Boc, R4=Me]

2-(2-Amino-5-iodo-pyrimidin-4-yl)-1-methyl-4-oxo-1,4,6,7-tetrahydro-pyrrolo[3,2-c]-pyridine-5-carboxylic acid tert-butyl ester (100 mg, 0.213 mmol) was suspended in dry acetonitrile (1.5 mL) in a dry screw cap Pirex tube. TEA (0.5 mL) was added and argon was bubbled through the mixture for 5 minutes. 3-Ethynylphenol (0.046 mL, 0.426 mmol, 2 eq) was then added followed by copper (I) iodide (2 mg, 0.11 mmol, 0.05 eq) and PdCl$_2$(PPh$_3$)$_2$ (8 mg, 0.011 mmol, 0.05 eq). The tube was closed and the mixture was stirred at 80° C. for 1.5 hours. After cooling to RT the solid was filtered and washed with acetonitrile and ether. The solid was then washed on the filter with a 9:1 water/methanol mixture (2 mL) and dried under high vacuum at 50° C. for 2 hours. 50 mg of the desired product were obtained as beige solid (51%).

HPLC (254 nm): $R_t$: 6.07 min.

$^1$H-NMR (401 MHz, DMSO-$d_6$) δ=9.65 (s, 1H), 8.46 (s, 1H), 7.51 (s, 1H), 7.19 (t, J=7.9 Hz, 1H), 7.10 (s, 2H), 6.89 (dt, J=1.1, 7.7 Hz, 1H), 6.77-6.83 (m, 2H), 4.00 (t, J=6.3 Hz, 2H), 3.84 (s, 3H), 2.99 (t, J=6.3 Hz, 2H), 1.47 (s, 9H).

HRMS (ESI) calcd for C25H26N5O4 [M+H]+ 460.1980. found 460.1981.

Operating in an analogous way the following Boc-protected intermediates were obtained:

2-(2-Amino-5-phenylethynyl-pyrimidin-4-yl)-1-methyl-4-oxo-1,4,6,7-tetrahydro-pyrrolo[3,2-c]pyridine-5-carboxylic acid tert-butyl ester

[(II)k, L2'=C≡C, Q=Boc, R4=Me]

HPLC (254 nm): $R_t$: 6.73 min.

$^1$H-NMR (401 MHz, DMSO-$d_6$) δ=8.48 (s, 1H), 7.56 (s, 1H), 7.37-7.51 (m, 5H), 7.13 (s, 2H), 4.01 (t, J=6.2 Hz, 2H), 3.86 (s, 3H), 3.00 (t, J=6.3 Hz, 2H), 1.48 (s, 9H).

HRMS (ESI) calcd for C25H26N5O3 [M+H]+ 444.2030. found 444.2042.

2-[2-Amino-5-(3-amino-phenylethynyl)-pyrimidin-4-yl]-1-methyl-4-oxo-1,4,6,7-tetrahydro-pyrrolo[3,2-c]pyridine-5-carboxylic acid tert-butyl ester

[(II)m, L2'=C≡C, Q=Boc, R4=Me]

HPLC (254 nm): $R_t$: 6.01 min.

$^1$H-NMR (401 MHz, DMSO-$d_6$) δ=8.43 (s, 1H), 7.53 (s, 1H), 7.08 (s, 2H), 7.03 (t, J=7.7 Hz, 1H), 6.69 (t, J=1.8 Hz, 1H), 6.62 (dt, J=1.2, 7.5 Hz, 1H), 6.58 (ddd, J=1.0, 2.3, 8.1 Hz, 1H), 5.17 (s, 2H), 4.01 (t, J=6.3 Hz, 2H), 3.85 (s, 3H), 3.00 (t, J=6.3 Hz, 2H), 1.48 (s, 9H).

HRMS (ESI) calcd for C25H27N6O3 [M+H]+ 459.2139. found 459.2136.

Step a (Method D)

2-[2-Amino-5-(3-hydroxy-phenylethynyl)-pyrimidin-4-yl]-1-methyl-1,5,6,7-tetrahydro-pyrrolo[3,2-c]pyridin-4-one hydrochloride

[(I), R1=H, R2=3-hydroxyphenylethynyl, R3=NH$_2$, R4=Me]

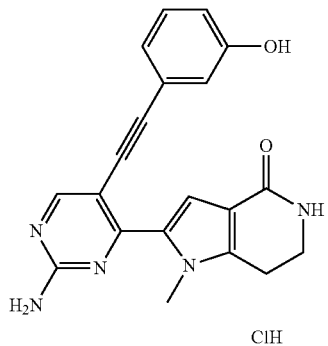 [SMILES: Cn1c(-c2nc(N)ncc2C#Cc2cccc(O)c2)cc2c1CCNC2=O ; Cl]

2-[2-Amino-5-(3-hydroxy-phenylethynyl)-pyrimidin-4-yl]-1-methyl-4-oxo-1,4,6,7-tetrahydro-pyrrolo[3,2-c]pyridine-5-carboxylic acid tert-butyl ester (22 mg, 0.048 mmol) was suspended in dry dioxane (1 mL) under nitrogen atmosphere and 4 N HCl solution in dioxane (0.120 mL, 0.48 mmol, 10 eq) was added. After stirring for 45 minutes at room temperature the suspension was evaporated to dryness, taken up with methanol and evaporated to dryness (3×2 mL). The residue was diluted with ethyl ether and evaporated to dryness (3×2 mL). The desired product was obtained as hydrochloride (21 mg, yellow solid).

HPLC (254 nm): R$_t$: 4.55 min.
$^1$H-NMR (401 MHz, DMSO-d$_6$) (selected signals) δ=9.70 (br. s., 1H), 8.46 (s, 1H), 7.53 (s, 1H), 7.20 (t, J=7.9 Hz, 1H), 7.15 (br. s., 1H), 6.92 (ddd, J=1.0, 1.2, 7.7 Hz, 1H), 6.83-6.85 (m, 1H), 6.80 (ddd, J=1.0, 2.3, 8.2 Hz, 1H), 3.87 (s, 3H), 3.43-4.50 (m, 2H), 2.91 (t, J=6.8 Hz, 2H).
HRMS (ESI) calcd for C20H18N5O2 [M+H]$^+$ 360.1455. found 360.1468.

Operating in an analogous way the following compounds were synthesized:

2-(2-Amino-5-phenylethynyl-pyrimidin-4-yl)-1-methyl-1,5,6,7-tetrahydro-pyrrolo[3,2-c]pyridin-4-one hydrochloride

[(I), R1=H, R2=phenylethynyl, R3=NH$_2$, R4=Me]

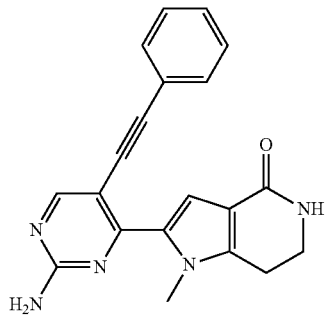 [SMILES: Cn1c(-c2nc(N)ncc2C#Cc2ccccc2)cc2c1CCNC2=O]

HPLC (254 nm): R$_t$: 4.97 min.
$^1$H-NMR (401 MHz, DMSO-d$_6$) (selected signals) δ=8.49 (s, 1H), 7.62 (s, 1H), 7.48-7.52 (m, 2H), 7.38-7.46 (m, 3H), 7.18 (br. s., 1H), 3.87 (s, 3H), 3.46 (m, 2H), 2.91 (t, J=6.8 Hz, 2H).
HRMS (ESI) calcd for C20H18N5O [M+H]$^+$ 344.1506. found 344.1498.

2-(2-Amino-5-phenylethynyl-pyrimidin-4-yl)-1-methyl-1,5,6,7-tetrahydro-pyrrolo[3,2-c]pyridin-4-one

[(I), R1=H, R2=3-aminophenylethynyl, R3=NH$_2$, R4=Me]

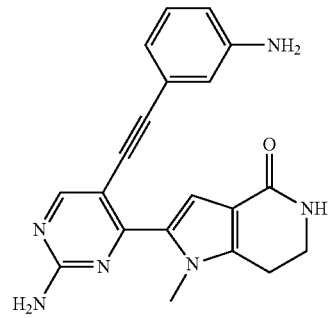 [SMILES: Cn1c(-c2nc(N)ncc2C#Cc2cccc(N)c2)cc2c1CCNC2=O]

The crude was treated with 7 N ammonia in methanol and evaporated to dryness. The free base was purified by flash chromatography on silica gel (DCM/EtOH/NH$_3$ in MeOH 90:10:1)(80% yield).
$^1$H-NMR (401 MHz, DMSO-d$_6$) δ=8.40 (s, 1H), 7.46 (s, 1H), 7.13 (s, 1H), 6.96-7.07 (m, 3H), 6.72 (t, J=1.8 Hz, 1H), 6.62 (dt, J=1.2, 7.5 Hz, 1H), 6.57 (ddd, J=1.0, 2.3, 8.1 Hz, 1H), 5.17 (s, 2H), 3.85 (s, 3H), 3.44 (td, 2H), 2.89 (t, J=6.9 Hz, 2H).
HRMS (ESI) calcd for C20H19N6O [M+H]$^+$ 359.1615. found 359.1618.

2-[2-Amino-5-(3-chloro-phenylethynyl)-pyrimidin-4-yl]-1-methyl-1,5,6,7-tetrahydro-pyrrolo[3,2-c]pyridin-4-one

[(I), R1=H, R2=3-chlorophenylethynyl, R3=NH$_2$, R4=Me]

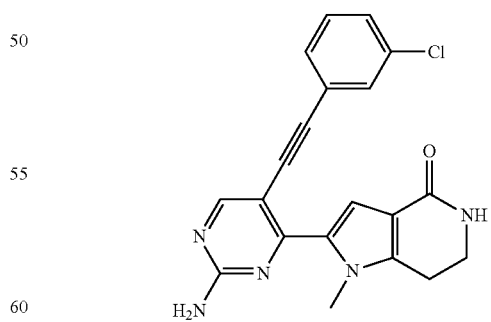

HPLC (254 nm): R$_t$: 5.49 min.
$^1$H-NMR (401 MHz, DMSO-d$_6$) (selected signals) δ=8.45 (s, 1H), 7.50-7.51 (m, 1H), 7.46 (s, 1H), 7.41-7.47 (m, 3H), 7.12 (br.s., 3H), 3.85 (s, 3H), 3.45 (td, J=2.4, 6.8 Hz, 2H), 2.89 (t, J=6.8 Hz, 2H).

HRMS (ESI) calcd for C20H17ClN5O [M+H]+ 378.1116. found 378.1112.

Example 10

2-[2-Amino-5-(3-hydroxy-phenylethynyl)-pyrimidin-4-yl]-1-(2-fluoro-ethyl)-1,5,6,7-tetrahydro-pyrrolo[3,2-c]pyridin-4-one (Cpd. no 3)

[(I), R1=H, R2=3-hydroxyphenylethynyl, R3=NH₂, R4=2-fluoroethyl]

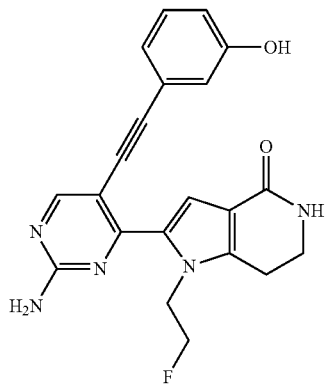 [SMILES: Nc1ncc(C#Cc2cccc(O)c2)c(-c2cc3c(n2CCF)CCNC3=O)n1]

The above compound was prepared according to Methods 8 and E as described below.

Step b (Method 8)

2-(2-Amino-5-iodo-pyrimidin-4-yl)-1-(2-fluoro-ethyl)-4-oxo-1,4,6,7-tetrahydro-pyrrolo[3,2-c]pyridine-5-carboxylic acid tert-butyl ester

[(17), R4=CH₂—CH₂F, Q=Boc]

2-(2-Amino-pyrimidin-4-yl)-1-(2-fluoro-ethyl)-4-oxo-1,4,6,7-tetrahydro-pyrrolo[3,2-c]pyridine-5-carboxylic acid tert-butyl ester (100 mg, 0.266 mmol) was dissolved in dry DMF (3 mL) and cooled to 0° C. Silver trifluoroacetate (59 mg, 0.266 mmol, 1 eq) was added, followed by iodine (68 mg, 0.266 mmol, 1 eq) and the reaction mixture was stirred at 0° C. for 1 h. It was then allowed to warm to room temperature and diluted with ethyl acetate. Silver salts were filtered over a Celite pad and washed with ethyl acetate. The filtrate was washed with water (4×5 mL), dried over sodium sulphate and evaporated to dryness. The crude product was treated with DCM/MeOH 1:1 (2 mL), filtered and dried under high vacuum at 40° C. for 2 hours. 100 mg of the desired product were obtained as yellow solid (75% yield).

HPLC (254 nm): R$_t$: 5.82 min.
$^1$H-NMR (401 MHz, DMSO-d₆) δ=8.58 (s, 1H), 7.06 (s, 1H), 6.87 (s, 2H), 4.56-4.76 (m, 2H), 4.38-4.53 (m, 2H), 3.99 (t, J=6.2 Hz, 2H), 2.99 (t, J=6.3 Hz, 2H), 1.48 (s, 9H).
HRMS (ESI) calcd for C18H22FIN5O3 [M+H]+ 502.0746. found 502.0739.

Step d (Method B)

2-[2-Amino-5-(3-hydroxy-phenylethynyl)-pyrimidin-4-yl]-1-(2-fluoro-ethyl)-4-oxo-1,4,6,7-tetrahydro-pyrrolo[3,2-c]pyridine-5-carboxylic acid tert-butyl ester

[(II)k, L2'=C≡C, Q=Boc, R4=2-fluoroethyl]

2-(2-Amino-5-iodo-pyrimidin-4-yl)-1-(2-fluoro-ethyl)-4-oxo-1,4,6,7-tetrahydro-pyrrolo[3,2-c]pyridine-5-carboxylic acid tert-butyl ester (95 mg, 0.190 mmol) was suspended in dry acetonitrile (2 mL) under nitrogen atmosphere. TEA (0.265 mL, 1.9 mmol, 10 eq) was added followed by 3-ethynylphenol (0.041 mL, 0.380 mmol, 2 eq) and argon was bubbled through the mixture for 5 minutes. Copper (I) iodide (2 mg, 0.010 mmol, 0.05 eq) and PdCl₂(PPh₃)₂ (7 mg, 0.010 mmol, 0.05 eq) were then added and the mixture was stirred at room temperature for 4 hours. The solid was filtered and washed with acetonitrile (1 mL), a 9:1 water/methanol mixture (2 mL) and ether (2 mL) After drying under high vacuum at room temperature for 2 hours, 58 mg of the desired product were obtained as beige solid (62%).

HPLC (254 nm): R$_t$: 6.27 min.
$^1$H-NMR (401 MHz, DMSO-d₆) δ=9.68 (s, 1H), 8.47 (s, 1H), 7.69 (s, 1H), 7.21 (t, J=7.9 Hz, 1H), 7.11 (s, 2H), 6.93 (ddd, J=1.0, 1.2, 7.7 Hz, 1H), 6.77-6.85 (m, 2H), 4.66-4.89 (m, 4H), 4.00 (t, J=6.2 Hz, 2H), 3.00 (t, J=6.2 Hz, 2H), 1.48 (s, 9H).
HRMS (ESI) calcd for C26H27FN5O4 [M+H]+ 492.2042. found 492.2035.

Step a (Method D)

2-[2-Amino-5-(3-hydroxy-phenylethynyl)-pyrimidin-4-yl]-1-(2-fluoro-ethyl)-1,5,6,7-tetrahydro-pyrrolo[3,2-c]pyridin-4-one

[(I), R1=H, R2=3-hydroxyphenylethynyl, R3=NH₂, R4=2-fluoroethyl]

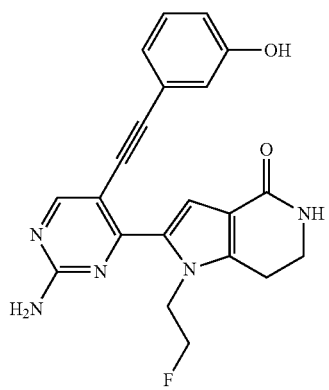 [SMILES: Nc1ncc(C#Cc2cccc(O)c2)c(-c2cc3c(n2CCF)CCNC3=O)n1]

2-[2-Amino-5-(3-hydroxy-phenylethynyl)-pyrimidin-4-yl]-1-(2-fluoro-ethyl)-4-oxo-1,4,6,7-tetrahydro-pyrrolo[3,2-c]pyridine-5-carboxylic acid tert-butyl ester (55 mg, 0.112 mmol) was suspended in dry dioxane (2 mL) under nitrogen atmosphere and 4 N HCl solution in dioxane (0.280 mL, 1.12 mmol, 10 eq) was added. After stirring for 1.5 hours at room temperature the solid was filtered and washed with ethyl ether. After drying under high vacuum at 50° C. for 3 hours, the desired product was obtained as hydrochloride (41 mg, yellow solid).

HPLC (254 nm): $R_t$: 4.75 min.

$^1$H-NMR (401 MHz, DMSO-$d_6$) δ=9.63 (br. s., 1H), 8.47 (s, 1H), 7.73 (s, 1H), 7.21 (t, J=7.9 Hz, 1H), 7.18-7.32 (br. s. 3H), 6.95 (ddd, J=1.0, 1.2, 7.7 Hz, 1H), 6.85-6.87 (m, 1H), 6.81 (ddd, J=0.9, 2.5, 8.2 Hz, 1H), 4.69-4.87 (m, 4H), 3.38-3.47 (m, 2H), 2.92 (t, J=6.8 Hz, 2H).

HRMS (ESI) calcd for C21H19FN5O2 [M+H]$^+$ 392.1518. found 392.1533.

Example 11

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(4-trifluoromethyl-phenyl)-urea

[(I), R1=H, R2=3-[3-(4-trifluoromethylphenyl)ureido]phenylethynyl, R3=NH$_2$, R4=methyl]

The above compound was prepared according to Methods B and D as described below.

Step j (Method B): 2-(2-Amino-5-{(3-[3-(4-trifluoromethyl-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester

[(II)p, L2'=C≡C, R4=Me, R5'=4-trifluoromethylphenyl, Q=Boc]

2-[2-Amino-5-(3-amino-phenylethynyl)-pyrimidin-4-yl]-1-methyl-4-oxo-1,4,6,7-tetra-hydro-pyrrolo[3,2-c]pyridine-5-carboxylic acid tert-butyl ester (prepared as described in Example 9) (98 mg, 0.214 mmol) was suspended in a 1:1 DCM/dioxane mixture (4 mL) under a nitrogen atmosphere. 4-Trifluoromethylphenylisocyanate (0.033 mL, 0.235 mmol, 1.1 eq) was added and the mixture was stirred at room temperature for 2 hours. After a further addition of 4-trifluoromethylphenylisocyanate (0.010 mL, 0.071 mmol, 0.33 eq) the reaction was stirred at room temperature overnight and then evaporated to dryness. The residue was taken up with methanol and evaporated to dryness (2×2 mL). It was taken up with ethyl ether (3 mL) and stirred at room temperature for 1 h. The solid was filtered and washed with ethyl ether. After drying at 40° C. under vacuum for 2 hours, 117 mg of the desired product were obtained as off-white solid (85%).

HPLC (254 nm): $R_t$: 7.90 min.

$^1$H-NMR (401 MHz, DMSO-$d_6$) δ=9.13 (s, 1H), 8.90 (s, 1H), 8.50 (s, 1H), 7.60-7.71 (m, 5H), 7.50 (s, 1H), 7.38-7.43 (m, 1H), 7.34 (t, J=7.9 Hz, 1H), 7.14 (s, 2H), 7.11 (dt, J=1.3, 7.5 Hz, 1H), 4.02 (t, J=6.3 Hz, 2H), 3.85 (s, 3H), 3.01 (t, J=6.3 Hz, 2H), 1.45 (s, 9H).

HRMS (ESI) calcd for C33H31F$_3$N7O4 [M+H]$^+$ 646.2384. found 646.2388.

Step a (Method D)

1-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-3-(4-trifluoromethyl-phenyl)-urea

[(I), R1=H, R2=3-[3-(4-trifluoromethylphenyl)ureido]phenylethynyl, R3=NH$_2$, R4=methyl]

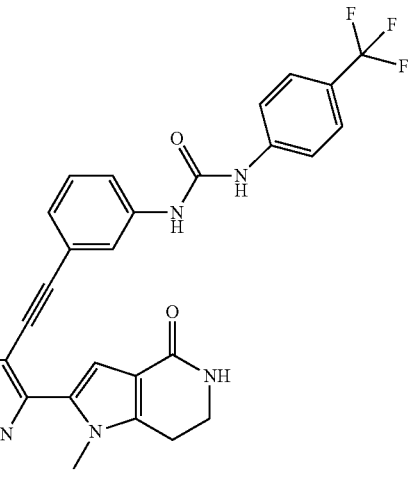

2-(2-Amino-5-{3-[3-(4-trifluoromethyl-phenyl)-ureido]-phenylethynyl}-pyrimidin-4-yl)-1-methyl-4-oxo-1,4,6,7-tetrahydro-pyrrolo[3,2-c]pyridine-5-carboxylic acid tert-butyl ester (115 mg, 0.178 mmol) was suspended in dry dioxane (2 mL) under nitrogen atmosphere and 4 N HCl solution in dioxane (0.450 mL, 1.8 mmol, 10 eq) was added. After stirring for 3 hours at room temperature the mixture was evaporated to dryness and the residue was purified by chromatography on silica gel (DCM/EtOH/7M NH$_3$ in methanol 95:5: 1.68 mg of the desired product were obtained (70%), part of which were suspended in a 1:1 DCM/EtOH mixture and stirred for 10 minutes. The solid was filtered and dried at 45° C. under high vacuum, obtaining 30 mg of white solid.

HPLC (254 nm): $R_t$: 6.38 min.

$^1$H-NMR (401 MHz, DMSO-$d_6$) δ=9.16 (s, 1H), 8.91 (s, 1H), 8.47 (s, 1H), 7.63-7.70 (m, 4H), 7.62-7.63 (m, 1H), 7.44 (s, 1H), 7.43 (dd, J=0.9, 2.1 Hz, 1H), 7.33 (t, J=7.9 Hz, 1H), 7.10-7.14 (m, 2H), 7.08 (s, 2H), 3.86 (s, 3H), 3.46 (td, J=2.6, 6.8 Hz, 2H), 2.90 (t, J=6.9 Hz, 2H).

HRMS (ESI) calcd for C28H23F$_3$N7O2 [M+H]$^+$ 546.1860. found 546.1853.

Example 12

N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-2,5-difluoro-benzenesulfonamide

[(I), R1=H, R2=3-(2,5-difluorobenzensulfonylamino)phenylethynyl, R3=NH$_2$, R4=methyl]

The above compound was prepared according to Methods B and D as described below.

Step i (Method B)

2-{2-Amino-5-[3-(2,5-difluoro-benzenesulfonylamino)-phenyl-ethynyl]-pyrimidin-4-yl}-1-methyl-4-oxo-1,4,6,7-tetrahydro-pyrrolo[3,2-c]-pyridine-5-carboxylic acid tert-butyl ester

[(II)n, R1=H, R2=3-(2,5-difluorobenzensulfonylamino)phenylethynyl, R3=NH$_2$, R4=methyl, Q=Boc]

2-[2-Amino-5-(3-amino-phenylethynyl)-pyrimidin-4-yl]-1-methyl-4-oxo-1,4,6,7-tetra-hydro-pyrrolo[3,2-c]pyridine-5-carboxylic acid tert-butyl ester (prepared as described in Example 9) (96 mg, 0.210 mmol) was dissolved in dry pyridine (2 mL) under nitrogen atmosphere. 2,5-Difluorobenzenesulfonyl chloride (0.030 mL, 0.226 mmol, 1.07 eq) and N-methylmorpholine (0.030 mL, 0.272 mmol, 1.3 eq) were added and the mixture was stirred at room temperature for 16 hours. The solvent was evaporated to dryness and the residue was taken up with DCM (10 mL), washed with water (3×3 mL) and brine (3 mL), dried over Na$_2$SO$_4$ and evaporated to dryness.

Step a (Method D)

N-{3-[2-Amino-4-(1-methyl-4-oxo-4,5,6,7-tetrahydro-1H-pyrrolo[3,2-c]pyridin-2-yl)-pyrimidin-5-ylethynyl]-phenyl}-2,5-difluoro-benzenesulfonamide

[(I), R1=H, R2=3-(2,5-difluorobenzensulfonylamino)phenylethynyl, R3=NH$_2$, R4=methyl]

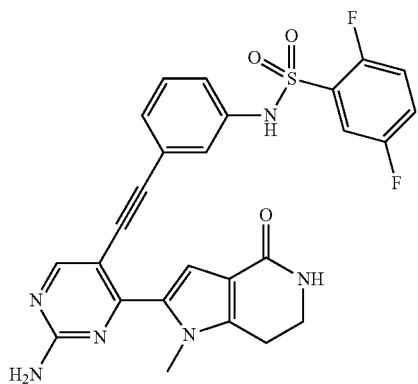 [SMILES: Cn1c(-c2nc(N)ncc2C#Cc2cccc(NS(=O)(=O)c3cc(F)ccc3F)c2)cc2c1CCNC2=O]

Crude 2-{2-amino-5-[3-(2,5-difluoro-benzenesulfonylamino)-phenyl-ethynyl]-pyrimi-din-4-yl}-1-methyl-4-oxo-1,4,6,7-tetrahydro-pyrrolo[3,2-c]-pyridine-5-carboxylic acid tert-butyl ester was suspended in dry dioxane (2 mL) under nitrogen atmosphere and 4 N HCl solution in dioxane (0.550 mL, 2.1 mmol, 10 eq) was added. After stirring for 1 h at room temperature the mixture was evaporated to dryness and the residue was purified by chromatography on silica gel (DCM/EtOH/7M NH$_3$ in methanol 92:7:1. The purified product was suspended in DCM and stirred for 10 minutes. The solid was filtered and dried at 45° C. under high vacuum, obtaining 20 mg of pale yellow solid (18%).

HPLC (254 nm): R$_t$: 4.45 min.

$^1$H-NMR (401 MHz, DMSO-d$_6$) δ=10.87 (s, 1H), 8.44 (s, 1H), 7.66-7.75 (m, 1H), 7.46-7.63 (m, 2H), 7.37 (s, 1H), 7.29 (t, J=7.3 Hz, 1H), 7.06-7.20 (m, 6H), 3.84 (s, 3H), 3.41-3.49 (m, 2H), 2.89 (t, J=6.9 Hz, 2H).

HRMS (ESI) calcd for C26H21F$_2$N$_6$O$_3$S [M+H]$^+$ 535.1359. found 535.1346.

Example 13

Thiophene-2-carboxylic acid 3-[2-amino-4-(1-methyl-4-oxo-4,5,6,7-tetrahydro-1H-pyrrolo[3,2-c]pyridin-2-yl)-pyrimidin-5-ylethynyl]-phenyl ester

[(I), R1=H, R2=3-(thiophene-2-carbonyloxy)phenylethynyl, R3=NH$_2$, R4=methyl]

The above compound was prepared according to Methods B and D as described below.

Step n (Method B): 2-{2-Amino-5-[3-(thiophene-2-carbonyloxy)-phenylethynyl]-pyrimidin-4-yl}-1-methyl-4-oxo-1,4,6,7-tetrahydro-pyrrolo[3,2-c]pyridine-5-carboxylic acid tert-butyl ester

[(II)t, L2'=C≡C, R4=Me, R5=2-thiophenyl, Q=Boc]

To a solution of 2-[2-amino-5-(3-hydroxy-phenylethynyl)-pyrimidin-4-yl]-1-methyl-4-oxo-1,4,6,7-tetrahydro-pyrrolo[3,2-c]pyridine-5-carboxylic acid tert-butyl ester (0.087 mmol, 1 eq)(prepared as described in Example 9) in 1 mL of dry THF under argon atmosphere were added at room temperature 2-thiophene-carbonylchloride (0.19 mmol, 2.2 eq) and DIPEA (0.13 mmol, 1.5 eq). After stirring for 3 h at room temperature the solvent was evaporated. The product was crystallized by refluxing in ethyl acetate and cooling slowly to room temperature affording 22 mg of white solid in 45% yield.

$^1$H-NMR (401 MHz, DMSO-d$_6$) δ=1.44 (s, 9H), 3.00 (t, 2H, J=6.4 Hz), 3.86 (s, 3H), 4.00 (t, 2H, J=6.4 Hz), 7.08 (m, 1H), 7.18 (bs, 2H), 7.32-7.42 (m, 4H), 7.51 (m, 1H), 7.56 (s, 1H), 8.05 (dd, 1H, J=3.8 and 1.3 Hz), 8.11 (dd, 1H, J=5.0 and 1.3 Hz), 8.49, (s, 1H).

Step a (Method D)

Thiophene-2-carboxylic acid 3-[2-amino-4-(1-methyl-4-oxo-4,5,6,7-tetrahydro-1H-pyrrolo[3,2-c]pyridin-2-yl)-pyrimidin-5-ylethynyl]-phenyl ester

[(I), R1=H, R2=3-(thiophene-2-carbonyloxy)phenylethynyl, R3=NH$_2$, R4=methyl]

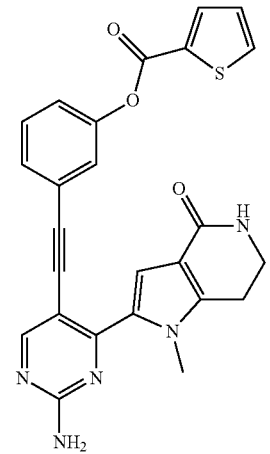 [SMILES: Cn1c(-c2nc(N)ncc2C#Cc2cccc(OC(=O)c3cccs3)c2)cc2c1CCNC2=O]

To a solution of starting material (0.04 mmol, 1 eq.) in 0.8 ml of dioxane were added at room temperature 10 equivalents of HCl 4M in dioxane. After stirring 2 h the solvent was evaporated affording a white solid in 90% yield.

HPLC (254 nm): R$_t$: 5.78 min.

$^1$H-NMR (401 MHz, DMSO-d$_6$) δ=2.90 (t, 2H, J=6.7 Hz), 3.45 (t, 2H, J=6.7 Hz), 3.87 (s, 3H), 7.15 (bs, 2H), 7.31-7.37 (m, 2H), 7.39-7.45 (m, 2H), 7.51 (m, 1H), 7.57 (s, 1H), 8.06 (dd, 1H, J=3.8 and 1.3 Hz), 8.12 (dd, 1H, J=5 and 1.3 Hz), 8.49 (dd, 1H, J=5 and 1.3 Hz).

HRMS (ESI) calcd for C25H20N5O3S [M+H]$^+$ 470.1282. found 470.1292.

Operating in an analogous way the following compound was synthesized.

4-Methyl-thiophene-2-carboxylic acid 3-[2-amino-4-(1-methyl-4-oxo-4,5,6,7-tetrahydro-1H-pyrrolo[3,2-c]pyridin-2-yl)-pyrimidin-5-ylethynyl]-phenyl ester

[(I), R1=H, R2=3-(4-methylthiophene-2-carbonyloxy)phenylethynyl, R3=NH$_2$, R4=methyl]

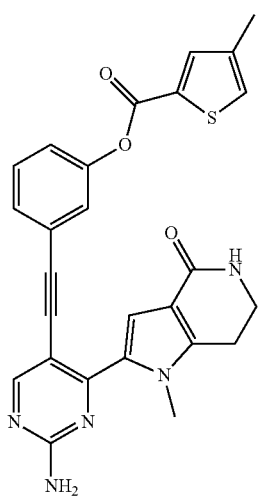 [SMILES: Cc1csc(C(=O)Oc2cccc(C#Cc3cnc(N)nc3-c3cc4c(n3C)CCNC4=O)c2)c1]

HPLC (254 nm): R: 6.14 min.

$^1$H-NMR (401 MHz, DMSO-d$_6$) δ=2.31 (s, 3H), 2.90 (t, 2H, J=6.8 Hz), 3.45 (t, 2H, J=6.8 Hz), 3.87 (s, 3H), 7.14 (bs, 2H), 7.33-7.42 (m, 3H), 7.50 (m, 1H), 7.56 (s, 1H), 7.71 (m, 1H), 7.89 (dd, 1H, J=1.6 and 0.3 Hz), 8.49 (s, 1H).

HRMS (ESI) calcd for C26H22N5O3S [M+H]$^+$ 484.1438. found 484.1420.

Example 14

2-{(2-Amino-5-[2-(3-hydroxy-phenyl)-ethyl]-pyrimidin-4-yl}-1-methyl-1,5,6,7-tetrahydro-pyrrolo[3,2-c]pyridin-4-one

[(I), R1=H, R2=2-(3-hydroxyphenyl)-ethyl, R3=NH$_2$, R4=methyl]

The above compound was prepared according to Methods C and D as described below.

2-{(2-Amino-5-[2-(3-hydroxy-phenyl)-ethyl]-pyrimidin-4-yl}-1-methyl-4-oxo-1,4,6,7-tetrahydro-pyrrolo[3,2-c]-pyridine-5-carboxylic acid tert-butyl ester

[(II)s', L2=CH$_2$CH$_2$, A=O, R5=H, R4=Me, Q=Boc]

2-[2-Amino-5-(3-hydroxy-phenylethynyl)-pyrimidin-4-yl]-1-methyl-4-oxo-1,4,6,7-tetrahydro-pyrrolo[3,2-c]pyridine-5-carboxylic acid tert-butyl ester (obtained as described in Example 9) (25 mg, 0.054 mmol) was dissolved in a methanol (25 mL) and the solution was submitted to continuous hydrogenation in a H-Cube apparatus equipped with a Pd/C 10% cartridge (1 atm of hydrogen, 40° C., flux: 1 mL/min). The solution was then evaporated to dryness and the crude product was purified by chromatography on silica gel (DCM/EtOH 95:5). 2-{2-Amino-5-[2-(3-hydroxy-phenyl)-ethyl]-pyrimidin-4-yl}-1-methyl-4-oxo-1,4,6,7-tetrahydro-pyrrolo[3,2-c]-pyridine-5-carboxylic acid tert-butyl ester were obtained as a white solid (19 mg, 76%).

Step a (Method D)

2-{2-Amino-5-[2-(3-hydroxy-phenyl)-ethyl]-pyrimidin-4-yl}-1-methyl-1,5,6,7-tetrahydro-pyrrolo[3,2-c]pyridin-4-one

[(I), R1=H, R2=2-(3-hydroxyphenyl)-ethyl, R3=NH$_2$, R4=methyl]

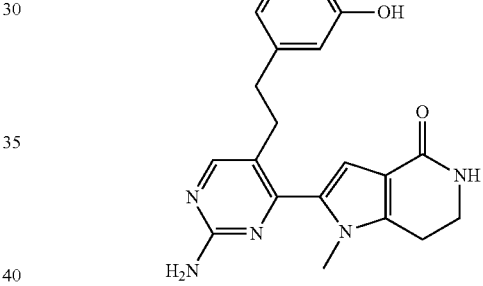

2-{2-Amino-5-[2-(3-hydroxy-phenyl)-ethyl]-pyrimidin-4-yl}-1-methyl-4-oxo-1,4,6,7-tetrahydro-pyrrolo[3,2-c]-pyridine-5-carboxylic acid tert-butyl ester (19 mg, 0.041 mmol) was dissolved in dry dioxane (1 mL) under nitrogen atmosphere and 4 N HCl solution in dioxane (0.100 mL, 0.410 mmol, 10 eq) was added. After stirring for 45 minutes at room temperature the suspension was evaporated to dryness, taken up with methanol and evaporated to dryness (3×2 mL). The residue was diluted with ethyl ether and evaporated to dryness (3×2 mL). After drying at 40° C. under high vacuum for 3 hours, the desired product was obtained as the hydrochloride (20 mg, yellow solid).

HPLC (254 nm): R$_t$: 4.01 min.

$^1$H-NMR (401 MHz, DMSO-d$_6$) (selected signals) δ=9.25 (br.s., 1H), 8.19 (s, 1H), 7.23 (br. s., 1H), 7.04 (t, J=7.7 Hz, 1H), 6.98 (s, 1H), 6.52-6.61 (m, 3H), 3.67 (s, 3H), 2.88-3.00 (m, 4H), 2.74 (t, J=7.7 Hz, 2H).

HRMS (ESI) calcd for C20H22N5O2 [M+H]$^+$ 364.1768. found 364.1785.

Operating in an analogous way the following compound were synthesized:

2-(2-Amino-5-phenethyl-pyrimidin-4-yl)-1-methyl-1,5,6,7-tetrahydro-pyrrolo[3,2-c]pyridin-4-one

[(I), R1=H, R2=2-phenyl-ethyl, R3=NH$_2$, R4=methyl]

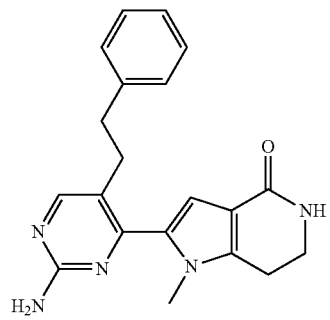 [SMILES: Cn1c(-c2nc(N)ncc2CCc2ccccc2)cc2c1CCNC2=O]

HPLC (254 nm): R$_t$: 4.66 min.

$^1$H-NMR (401 MHz, DMSO-d$_6$) δ=8.15 (s, 1H), 7.20-7.27 (m, 2H), 7.13-7.20 (m, 1H), 7.10 (d, J=1.5 Hz, 2H), 7.00-7.06 (m, 1H), 6.57 (s, 1H), 6.39 (s, 2H), 3.51 (s, 3H), 3.40-3.45 (m, 2H), 2.81-2.90 (m, 4H), 2.75 (t, J=7.8 Hz, 2H).

HRMS (ESI) calcd for C20H22N$_5$O [M+H]$^+$ 348.1819. found 348.1822.

Example 15

4-Methyl-thiophene-2-carboxylic acid [4-(1-methyl-4-oxo-4,5,6,7-tetrahydro-1H-pyrrolo[3,2-c]pyridin-2-yl)-pyrimidin-2-yl]-amide (Cpd. no 14)

[(I), R1=H, R2=H, R3=(4-methylthiophene-2-carbonylamino), R4=methyl]

The above compound was prepared according to Methods C and D as described below.

Step a (Method C)

1-methyl-2-{2-[(4-methyl-thiophene-2-carbonyl)-amino]-pyrimidin-4-yl}-4-oxo-1,4,6,7-tetrahydro-pyrrolo[3,2-c]pyridine-5-carboxylic acid tert-butyl ester

[(II)u, R4=Me, R5=4-methylthiophen-2-yl, Q=Boc]

2-(2-Amino-pyrimidin-4-yl)-1-methyl-4-oxo-1,4,6,7-tetrahydro-pyrrolo[3,2-c]pyridine-5-carboxylic acid tert-butyl ester (prepared as described in Example 9) (300 mg, 0.873 mmol) was suspended in dry pyridine under nitrogen atmosphere and sonicated for 2 minutes. 4-Methyl-thiophene-2-carbonyl chloride (0.142 mL, 1.135 mmol, 1.3 eq) and DMAP (10 mg, 0.087 mmol, 0.1 eq) were added and the mixture was stirred at room temperature for 3 hours. Pyridine was then evaporated and the residue was taken up with saturated aqueous NaHCO$_3$ (10 mL) and extracted with ethyl acetate (3×10 mL). Combined organic layers were washed with brine (3×10 mL), dried over Na$_2$SO$_4$ and evaporated to dryness. The crude product was purified by chromatography on silica gel (gradient n-hexane/ethyl acetate 1:1 to pure ethyl acetate) to obtain 394 mg of 1-methyl-2-{2-[(4-methyl-thiophene-2-carbonyl)-amino]-pyrimidin-4-yl}-4-oxo-1,4,6,7-tetrahydro-pyrrolo[3,2-c]pyridine-5-carboxylic acid tert-butyl ester (85%).

Step a (Method D)

4-Methyl-thiophene-2-carboxylic acid [4-(1-methyl-4-oxo-4,5,6,7-tetrahydro-1H-pyrrolo[3,2-c]pyridin-2-yl)-pyrimidin-2-yl]-amide

[(I), R1=H, R2=H, R3=(4-methylthiophene-2-carbonylamino), R4=methyl]

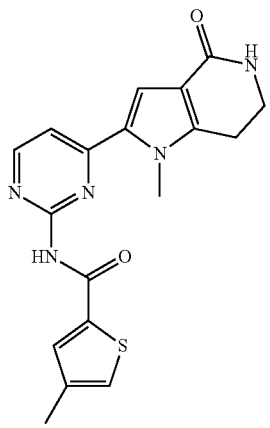 [SMILES: Cc1csc(C(=O)Nc2nccc(-c3cc4c(n3C)CCNC4=O)n2)c1]

This intermediate was dissolved in dry dioxane (15 mL) under nitrogen atmosphere and 4 N HCl solution in dioxane (2.1 mL, 8.4 mmol, 10 eq) was added. After stirring for 1 h at room temperature solvent was evaporated and the residue was taken up with methanol and evaporated to dryness (2×5 mL). The yellow solid was then treated with 7N NH$_3$ in methanol (5 mL) and evaporated to dryness. The crude product was purified by chromatography on silica gel (DCM/MeOH 92:8) to give an off-white solid, which was slurried in ethyl ether (5 mL) and filtered. After drying at 40° C. under high vacuum for 5 hours, 227 mg of 4-methyl-thiophene-2-carboxylic acid [4-(1-methyl-4-oxo-4,5,6,7-tetrahydro-1H-pyrrolo[3,2-c]pyridin-2-yl)-pyrimidin-2-yl]-amide were obtained as a white solid (73%).

HPLC (254 nm): R$_t$: 4.79 min.

$^1$H-NMR (401 MHz, DMSO-d$_6$) δ=10.89 (s, 1H), 8.55 (d, J=5.5 Hz, 1H), 7.99 (d, J=0.9 Hz, 1H), 7.56 (d, J=5.5 Hz, 1H), 7.50-7.51 (m, 1H), 7.27 (s, 1H), 7.15 (br. s., 1H), 4.09 (s, 3H), 3.44 (td, J=1.8, 6.8 Hz, 2H), 2.89 (t, J=6.8 Hz, 2H), 2.27 (s, 3H).

HRMS (ESI) calcd for C18H18N5O$_2$S [M+H]$^+$ 368.1176. found 368.1170.

Operating in an analogous way the following compound was obtained:

3-Chloro-N-[4-(1-methyl-4-oxo-4,5,6,7-tetrahydro-1H-pyrrolo[3,2-c]pyridin-2-yl)-pyrimidin-2-yl]-benzamide (Cpd. no 10)

[(I), R1=H, R2=H, R3=(3-chlorophenyl-carbonylamino), R4=methyl]

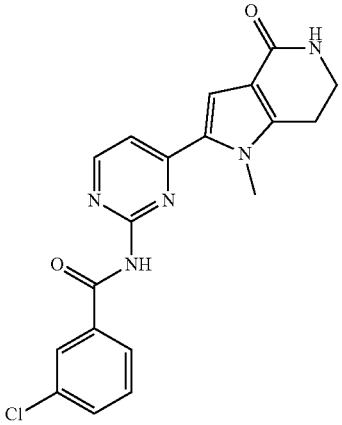 [SMILES: Cn1c(-c2ccnc(NC(=O)c3cccc(Cl)c3)n2)cc2c1CCNC2=O]

HPLC (254 nm): R$_t$: 5.01 min.
$^1$H-NMR (401 MHz, DMSO-d$_6$) δ=11.06 (s, 1H), 8.57 (d, J=5.5 Hz, 1H), 8.01 (t, J=1.8 Hz, 1H), 7.93 (ddd, J=0.8, 1.1, 7.5 Hz, 1H), 7.69 (ddd, J=1.0, 2.1, 8.0 Hz, 1H), 7.58 (d, J=5.5 Hz, 1H), 7.56 (t, J=7.9 Hz, 1H), 7.28 (s, 1H), 7.15 (br. s., 1H), 4.08 (s, 3H), 3.44 (td, J=2.5, 6.9 Hz, 2H), 2.89 (t, J=6.9 Hz, 2H).
HRMS (ESI) calcd for C19H17ClN5O2 [M+H]$^+$ 382.1066. found 382.1072.

Example 16

Furan-2-carboxylic acid [4-(1-methyl-4-oxo-4,5,6,7-tetrahydro-1H-pyrrolo[3,2-c]pyridin-2-yl)-pyrimidin-2-yl]-amide

[(I), R1=H, R2=H, R3=(furyl-2-carbonylamino), R4=methyl]
The above compound was prepared according to Methods C and D as described below.

Step a (Method C)

2-{2-[(Furan-2-carbonyl)-amino]-pyrimidin-4-yl}-1-methyl-4-oxo-1,4,6,7-tetrahydro-pyrrolo[3,2-c]pyridine-5-carboxylic acid tert-butyl ester

[(II)u, R4=Me, R5=2-furyl, Q=Boc]
To a solution of 2-(2-amino-pyrimidin-4-yl)-4-oxo-1,4,6,7-tetrahydro-pyrrolo[3,2-c]-pyridine-5-carboxylic acid tert-butyl ester (prepared as described in Example 9) (0.255 mmol, 1 eq) in 2.5 mL of dry DCM and TEA (1.617 mmol, 6.3 eq) under argon atmosphere, 2-furane-carbonylchloride (0.803 mmol, 3.15 eq) was added at room temperature within 10 minutes. After stirring for 3 h at room temperature, the solvent was evaporated, the crude dissolved in 2 ml of MeOH and treated with 2.1 equivalents of NaOH 1N. The mixture was stirred for 2 h at room temperature until HPLC revealed conversion of starting diacylated product into the monoacylated; finally stoichiometric amount of HCl 2N was added. The methanol was evaporated under vacuum and the crude was washed with water and extracted twice with CH$_2$Cl$_2$, dried over Na2SO4 and evaporated to dryness. The residue was then purified by flash column chromatography (98:2 CH2Cl2:MeOH) affording 2-{2-[(furan-2-carbonyl)-amino]-pyrimidin-4-yl}-1-methyl-4-oxo-1,4,6,7-tetrahydro-pyrrolo[3,2-c]pyridine-5-carboxylic acid tert-butyl ester as a white solid in 24% yield.

Step a (Method D)

Furan-2-carboxylic acid [4-(1-methyl-4-oxo-4,5,6,7-tetrahydro-1H-pyrrolo[3,2-c]pyridin-2-yl)-pyrimidin-2-yl]-amide

[(I), R1=H, R2=H, R3=(furyl-2-carbonylamino), R4=methyl]

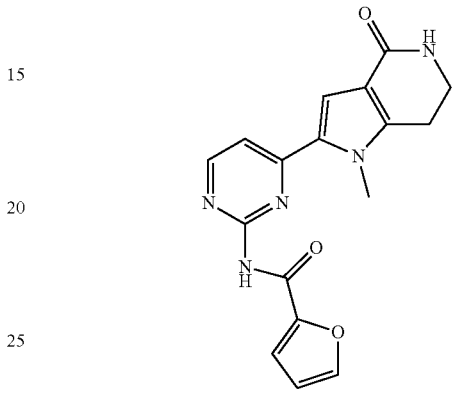

The Boc-protected intermediate was dissolved in 1 mL dioxane, then 0.16 mL HCl 4 M in dioxane were added at room temperature overnight. The final suspension was evaporated under vacuum, the residue triturate in Et2O then dried affording 28.8 mg of the product as a yellow solid.
HPLC (254 nm): R$_t$: 3.29 min.
$^1$H-NMR (401 MHz, DMSO-d$_6$) δ=2.91 (t, 2H, J=6.70 Hz), 3.45 (t, 2H, J=6.70 Hz), 4.10 (s, 3H), 6.73 (dd, 1H, J=1.71 and 3.60 Hz), 7.19 (bs, 1H), 7.34 (s, 1H), 7.59 (dd, 1H, J=0.73 and 3.52), 7.60 (d, 1H, J=5.61 Hz), 7.99 (dd, 1H, J=0.73 and 1.78), 8.53 (d, 1H, J=5.61 Hz), 10.91 (bs, 1H).
HRMS (ESI) calcd for C17H16N5O3 [M+H]$^+$ 338.1248. found 338.1235.
Operating in an analogous way the following compounds were prepared:

Thiophene-2-carboxylic acid [4-(1-methyl-4-oxo-4,5,6,7-tetrahydro-1H-pyrrolo[3,2-c]pyridin-2-yl)-pyrimidin-2-yl]-amide (Cpd. no 11)

[(I), R1=H, R2=H, R3=(thiophene-2-carbonylamino), R4=methyl]

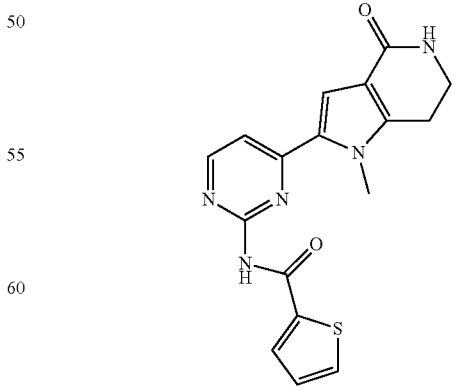

HPLC (254 nm): R$_t$: 3.29 min.
1H-NMR (401 MHz, DMSO-d6) δ=2.91 (t, 2H, J=6.70 Hz), 3.45 (t, 2H, J=6.70 Hz), 4.11 (s, 3H), 7.19 (bs, 1H), 7.25

(dd, 1H, J=3.78 and 5.20), 7.33 (s, 1H), 7.61 (d, 1H, J=5.61 Hz), 7.94 (dd, 1H, J=1.19 and 5.03), 8.19 (dd, 1H, J=1.10 and 3.83), 8.55 (d, 1H, J=5.61 Hz), 11.16 (bs, 1H).

HRMS (ESI) calcd for C17H16N5O2S [M+H]+ 354.1019. found 354.1009.

5-Phenyl-thiophene-2-carboxylic acid [4-(1-methyl-4-oxo-4,5,6,7-tetrahydro-1H-pyrrolo[3,2-c]pyridin-2-yl)-pyrimidin-2-yl]-amide

[(I), R1=H, R2=H, R3=(5-phenyl-thiophene-2-carbonylamino), R4=methyl]

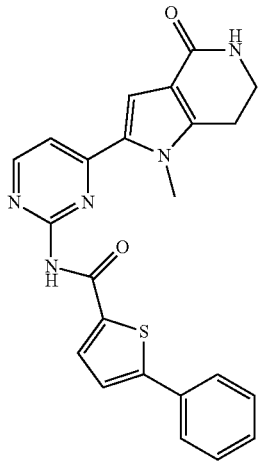 [SMILES: Cn1c(-c2ccnc(NC(=O)c3ccc(-c4ccccc4)s3)n2)cc2c1CCNC2=O]

HPLC (254 nm): R$_t$: 5.71 min.

$^1$H-NMR (401 MHz, DMSO-d6) δ=2.90 (t, 2H, J=6.83 Hz), 3.45 (td, 2H, J=2.56 and 7.07), 4.12 (s, 3H), 7.15 (bt, 1H, J=2.56 Hz), 7.28 (s, 1H), 7.41 (tt, 1H, J=1.22 and 7.44), 7.49 (m, 2H), 7.57 (d, 1H, J=5.36), 7.63 (d, 1H, J=4.02), 7.77 (m, 2H), 8.18 (d, 1H, J=4.02), 8.57 (d, 1H, J=5.49 Hz), 11.03 (s, 1H).

HRMS (ESI) calcd for C23H20N5O2S [M+H]+ 430.1332. found 430.1332.

4-Bromo-thiophene-2-carboxylic acid[4-(1-methyl-4-oxo-4,5,6,7-tetrahydro-1H-pyrrolo[3,2-c]pyridin-2-yl)-pyrimidin-2-yl]-amide (Cpd. no 4)

[(I), R1=H, R2=H, R3=(4-bromo-thiophene-2-carbonylamino), R4=methyl]

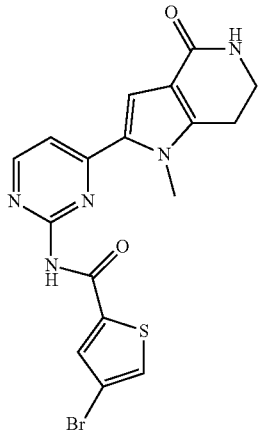 [SMILES: Cn1c(-c2ccnc(NC(=O)c3cc(Br)cs3)n2)cc2c1CCNC2=O]

HPLC (254 nm): R$_t$: 5.08 min.

$^1$H-NMR (401 MHz, DMSO-d6) δ=2.90 (t, 2H, J=6.9 Hz), 3.45 (t, 2H, J=6.9 Hz), 4.10 (s, 3H), 7.18 (bs, 1H), 7.31 (s, 1H), 7.60 (d, 1H, J=5.5 Hz), 8.06 (d, 1H, J=1.5 Hz), 8.25 (d, 1H, J=1.5 Hz), 8.56 (d, 1H, J=5.5 Hz), 11.16 (bs, 1H).

HRMS (ESI) calcd for C17H15BrN5O2S [M+H]+ 432.0125. found 432.0123.

N-[4-(1-Methyl-4-oxo-4,5,6,7-tetrahydro-1H-pyrrolo[3,2-c]pyridin-2-yl)-pyrimidin-2-yl]-benzamide

[(I), R1=H, R2=H, R3=benzoylamino, R4=methyl]

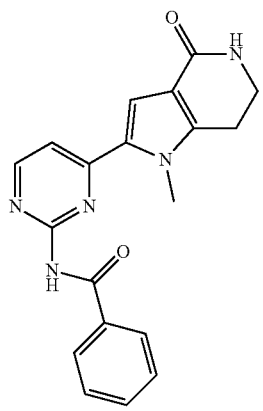 [SMILES: Cn1c(-c2ccnc(NC(=O)c3ccccc3)n2)cc2c1CCNC2=O]

HPLC (254 nm): R$_t$: 4.46 min.

$^1$H-NMR (401 MHz, DMSO-d6) δ=2.89 (t, 2H, J=6.83 Hz), 3.44 (t, 2H, J=6.83 Hz), 4.07 (s, 3H), 7.18 (bs, 1H), 7.35 (s, 1H), 7.54 (m, 2H), 7.60-7.65 (m, 2H), 7.93-8.00 (m, 2H), 8.53 (d, 1H, J=5.82), 11.14 (bs, 1H).

HRMS (ESI) calcd for C19H18N5O2 [M+H]+ 348.1455. found 348.1463.

Thiophene-3-carboxylic acid [4-(1-methyl-4-oxo-4,5,6,7-tetrahydro-1H-pyrrolo-[3,2-c]pyridin-2-yl)-pyrimidin-2-yl]-amide (Cpd. no 12)

[(I), R1=H, R2=H, R3=thiophene-3-carbonylamino, R4=methyl]

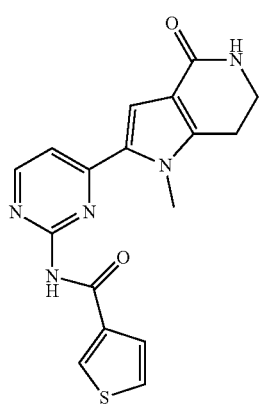 [SMILES: Cn1c(-c2ccnc(NC(=O)c3ccsc3)n2)cc2c1CCNC2=O]

HPLC (254 nm): R$_t$: 4.33 min.

$^1$H-NMR (401 MHz, DMSO-d6) δ=2.90 (t, 2H, J=6.8 Hz), 3.45 (t, 2H, J=6.8 Hz), 4.11 (s, 3H), 7.17 (bs, 1H), 7.30 (s, 1H), 7.58 (d, 1H, J=5.5 Hz), 7.64-7.68 (m, 2H), 8.53 (m, 1H), 8.55 (d, 1H, J=5.5), 10.86 (bs, 1H).

HRMS (ESI) calcd for C17H16N5O2S [M+H]+ 354.1019. found 354.1020.

Cyclopentanecarboxylic acid [4-(1-methyl-4-oxo-4,5,6,7-tetrahydro-1H-pyrrolo[3,2-c]pyridin-2-yl)-pyrimidin-2-yl]-amide

[(I), R1=H, R2=H, R3=cyclopentylcarbonylamino, R4=methyl]

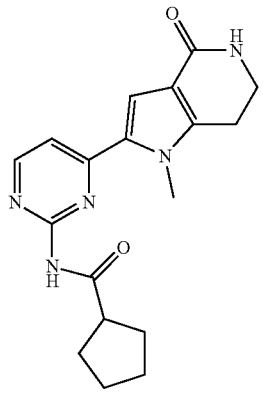 [SMILES: Cn1c(-c2ccnc(NC(=O)C3CCCC3)n2)cc2c1CCNC2=O]

HPLC (254 nm): R$_t$: 4.52 min.
$^1$H-NMR (401 MHz, DMSO-d6) δ=1.4-91.98 (m, 8H), 2.92 (t, 2H, J=6.95 Hz), 3.08 (m, 1H), 3.45 (t, 2H, J=6.95 Hz), 4.08 (s, 3H), 7.26 (bs, 1H), 7.46 (s, 1H), 7.64 (d, 1H, J=6.1 Hz), 8.41 (d, 1H, J=6.1 Hz), 11.18 (bs, 1H).
HRMS (ESI) calcd for C18H22N5O2 [M+H]+ 340.1768. found 340.1760.

Example 17

Thiophene-2-carboxylic acid {4-[1-(2-fluoro-ethyl)-4-oxo-4,5,6,7-tetrahydro-1H-pyrrolo[3,2-c]pyridin-2-yl]-pyrimidin-2-yl}-amide (Cpd. no 5)

[(I), R1=H, R2=H, R3=thiophene-2-carbonylamino, R4=2-fluoroethyl]

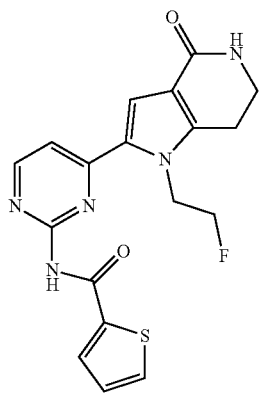 [SMILES: O=C(Nc1nccc(-c2cc3c(n2CCF)CCNC3=O)n1)c1cccs1]

The above compound was prepared according to Methods C and D as described below.
To a solution of 2-(2-amino-pyrimidin-4-yl)-1-(2-fluoro-ethyl)-4-oxo-1,4,6,7-tetra-hydro-pyrrolo[3,2-c]pyridine-5-carboxylic acid tert-butyl ester (synthesised as reported in Example 9) (0.4 mmol, 1 eq) in 3 mL of dry DCM under argon atmosphere were added at room temperature the 2-tiophene-carbonylchloride (0.84 mmol, 2.1 eq) and DIPEA (1.2 mmol, 3 eq), After stirring for 2 h at room temperature, the solvent was evaporated, the crude was used without any further purification and dissolved in 3 ml of MeOH, treated with 3.5 equivalents of NaOH 1N. The mixture was warmed for 2 h at 40° C. until HPLC revealed conversion of starting diacylated product into the monoacylated; finally stoichiometric amount of HCl 2N was added. After evaporated the crude to dryness 2 ml of HCl 4M in dioxane were added and the suspension stirred at room temperature for 3 h. Finally the solvent was removed under vacuum affording 30 mg of an orange solid in 33% yield.

HPLC (254 nm): R$_t$: 4.82 min.
$^1$H-NMR (401 MHz, DMSO-d6) δ=2.90 (t, 2H, J=6.8 Hz), 3.38-3.48 (m, 2H), 4.71 (m, 2H), 5.10 (m, 2H), 7.21 (bs, 1H), 7.23 (d, 1H, J=5 Hz), 7.41 (s, 1H), 7.63 (d, 1H, J=5.5 Hz), 7.92 (dd, 1H, J=5 and 1.1 Hz), 8.18 (dd, 1H, J=5 and 1.1 Hz), 8.56 (d, 1H, J=5.5 Hz), 11.05 (bs, 1H).
HRMS (ESI) calcd for C18H17FN5O2S [M+H]+ 386.1082. found 386.1091.

Operating in an analogous way the following compound was synthesized:

Furan-2-carboxylic acid {4-[1-(2-fluoro-ethyl)-4-oxo-4,5,6,7-tetrahydro-1H-pyrrolo[3,2-c]pyridin-2-yl]-pyrimidin-2-yl}-amide (Cpd. no 13)

[(I), R1=H, R2=H, R3=furyl-2-carbonylamino, R4=2-fluoro-ethyl]

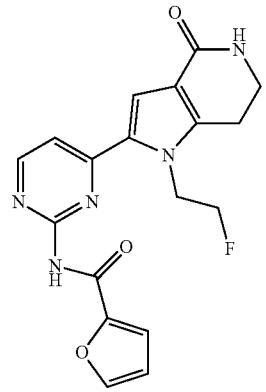 [SMILES: O=C(Nc1nccc(-c2cc3c(n2CCF)CCNC3=O)n1)c1ccco1]

The Boc-derivative (0.153 mmol, 1 eq.) was dissolved in 1.5 ml of dioxane and treated with 10 equivalents of HCl 4 M in dioxane at room temperature. After 4 h the suspension has been evaporated and the residue crushed with diethyl ether, filtered-off and dried giving the desired product as a white solid.
HPLC (254 nm): R$_t$: 4.41 min.
$^1$H-NMR (401 MHz, DMSO-d6) δ=2.91 (t, 2H, J=6.8 Hz), 3.42 (t, 2H, J=6.8 Hz), 4.66 (t, 1H, J=4.4 Hz), 4.78 (t, 1H, J=4.4 Hz), 5.05 (t, 1H, J=4.4 Hz), 5.13 (t, 1H, J=4.4 Hz), 6.72 (dd, 1H, J=3.6 and 1.7 Hz), 7.24 (bs, 1H), 7.45 (s, 1H), 7.60 (dd, 1H, J=3.6 and 0.7 Hz), 7.65 (d, 1H, J=5.6 Hz), 7.98 (dd, 1H, J=1.7 and 0.7 Hz), 8.54 (d, 1H, J=5.6 Hz), 10.87 (bs, 1H).
HRMS (ESI) calcd for C18H17N5O3F [M+H]+ 370.1310. found 370.1322.

Example 18

1-{4-[1-(2-Fluoro-ethyl)-4-oxo-4,5,6,7-tetrahydro-1H-pyrrolo[3,2-c]pyridin-2-yl]-pyrimidin-2-yl}-3-phenyl-urea

[(I), R1=H, R2=H, R3=3-phenyl-ureido, R4=2-fluoroethyl]
The above compound was prepared according to Methods C and D as described below.

Step b (Method C)

1-(2-Fluoro-ethyl)-4-oxo-2-[2-(3-phenyl-ureido)-pyrimidin-4-yl]-1,4,6,7-tetrahydro-pyrrolo[3,2-c]pyridine-5-carboxylic acid tert-butyl ester

[(II)v, R4=2-fluoroethyl, R5=phenyl, Q=Boc]

To a solution of 2-(2-amino-pyrimidin-4-yl)-1-(2-fluoro-ethyl)-4-oxo-1,4,6,7-tetra-hydro-pyrrolo[3,2-c]pyridine-5-carboxylic acid tert-butyl ester (synthesised as reported in Example 9) (0.29 mmol, 1 eq) in 3 mL of dry DCM under argon atmosphere were added at room temperature the phenyl-isocyanate (0.44 mmol, 1.5 eq) and DIPEA (0.44 mmol, 1.5 eq). After stirring at reflux temperature for 2 days the solvent was removed under vacuum and the residue purified by flash column chromatography (DCM/MeOH 9:1) affording 90 mg of a white solid in 65% yield.

HPLC (254 nm): R: 6.96 min.
$^1$H-NMR (401 MHz, DMSO-d6) δ=1.49 (s, 9H), 3.00 (t, 2H, J=6.25 Hz), 3.99 (t, 2H, J=6.25 Hz), 4.75 (m, 2H), 5.00 (m, 2H), 7.07 (m, 1H), 7.35 (m, 2H), 7.57 (s, 1H), 7.59 (m, 3H), 8.53 (d, 1H, J=5.5 Hz), 10.14 (bs, 1H), 11.38 (bs, 1H).
HRMS (ESI) calcd for C25H28N6O4F [M+H]+ 495.2151. found 495.2155.

Step a (Method D)

1-{4-[1-(2-Fluoro-ethyl)-4-oxo-4,5,6,7-tetrahydro-1H-pyrrolo-[3,2-c]pyridin-2-yl]-pyrimidin-2-yl}-3-phenyl-urea

[(I), R1=H, R2=H, R3=3-phenyl-ureido, R4=2-fluoroethyl]

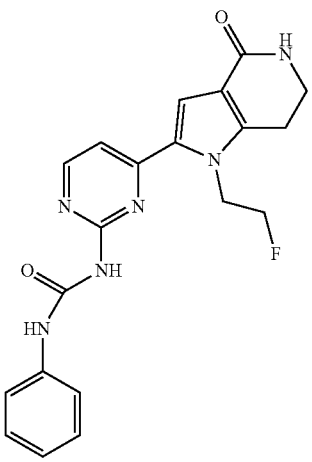 [SMILES: O=C(Nc1ccccc1)Nc1nccc(-c2cc3c(n2CCF)CCNC3=O)n1]

To a solution of 1-(2-fluoro-ethyl)-4-oxo-2-[2-(3-phenyl-ureido)-pyrimidin-4-yl]-1,4,6,7-tetrahydro-pyrrolo[3,2-c]pyridine-5-carboxylic acid tert-butyl ester (0.18 mmol, 1 eq) in 2 ml of dioxane were added at room temperature 10 equivalents of HCl 4M in dioxane. After stirring 24 h the solvent was evaporated affording a white solid in 90% yield.

HPLC (254 nm): R$_t$: 5.36 min.
$^1$H-NMR (401 MHz, DMSO-d6) δ=2.91 (t, 2H, J=6.8 Hz), 3.44 (t, 2H, J=6.8 Hz), 4.76 (m, 2H), 4.99 (m, 2H), 7.08 (m, 1H), 7.28 (bs, 1H), 7.35 (t, 2H, J=7.5 Hz), 7.52 (s, 1H), 7.58 (t, 3H, J=7.5 Hz), 8.45 (d, 1H, J=5.7 Hz), 10.36 (bs, 1H), 11.32 (bs, 1H).
HRMS (ESI) calcd for C20H20N6O2F [M+H]+ 395.1627. found 395.1628.

Example 19

1-[4-(1-Methyl-4-oxo-4,5,6,7-tetrahydro-1H-pyrrolo[3,2-c]pyridin-2-yl)-pyrimidin-2-yl]-3-phenyl-urea

[(I), R1=H, R2=H, R3=3-phenyl-ureido, R4=methyl]

The above compound was prepared according to Methods C and D as described below.

Step b (Method C)

1-Methyl-4-oxo-2-[2-(3-phenyl-ureido)-pyrimidin-4-yl]-1,4,6,7-tetrahydro-pyrrolo[3,2-c]pyridine-5-carboxylic acid tert-butyl ester

[(II)v, R4=methyl, R5=phenyl, Q=Boc]

To a solution of 2-(2-amino-pyrimidin-4-yl)-1-methyl-4-oxo-1,4,6,7-tetrahydro-pyrrolo-[3,2-c]pyridine-5-carboxylic acid tert-butyl ester (synthesised as reported in Example 9) (0.32 mmol, 1 eq) in 3 mL of dry DCM under argon atmosphere were added at room temperature the phenyl-isocyanate (1.44 mmol, 4.5 eq). After stirring at room temperature for 2 days the solvent was removed under vacuum and the residue purified by flash column chromatography (DCM/MeOH 9:1) affording 60 mg of a white solid in 40% yield.

HPLC (254 nm): R$_t$: 6.71 min.
$^1$H-NMR (401 MHz, DMSO-d6) δ=1.48 (s, 9H), 3.00 (t, 2H, J=6.25 Hz), 3.98 (t, 2H, J=6.25 Hz), 4.00 (s, 3H), 7.07 (m, 1H), 7.35 (m, 2H), 7.41 (s, 1H), 7.49 (d, 1H, J=6 Hz), 7.60 (m, 2H), 8.54 (d, 1H, J=6 Hz), 10.14 (bs, 1H), 11.41 (bs, 1H).
HRMS (ESI) calcd for C24H27N6O4 [M+H]+ 463.2089. found 463.2084.

Step a (Method D)

1-[4-(1-Methyl-4-oxo-4,5,6,7-tetrahydro-1H-pyrrolo[3,2-c]pyridin-2-yl)-pyrimidin-2-yl]-3-phenyl-urea

[(I), R1=H, R2=H, R3=3-phenyl-ureido, R4=methyl]

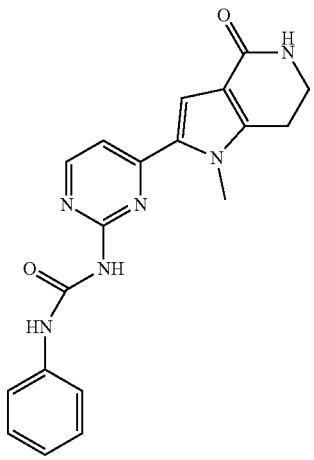 [SMILES: Cn1c(-c2ccnc(NC(=O)Nc3ccccc3)n2)cc2c1CCNC2=O]

To a solution of 1-methyl-4-oxo-2-[2-(3-phenyl-ureido)-pyrimidin-4-yl]-1,4,6,7-tetra-hydro-pyrrolo[3,2-c]pyridine-5-carboxylic acid tert-butyl ester (0.11 mmol, 1 eq) in 2 mL of dioxane were added at room temperature 10 equivalents of HCl 4M in dioxane. After stirring 2 h the solvent was evaporated affording a white solid in 90% yield.

HPLC (254 nm): R$_t$: 5.13 min.

¹H-NMR (401 MHz, DMSO-d6) δ=2.91 (t, 2H, J=6.8 Hz), 3.44 (t, 2H, J=6.8 Hz), 4.00 (s, 3H), 7.08 (m, 1H), 7.20 (bs, 1H), 7.35 (m, 3H), 7.47 (d, 1H, J=5.7 Hz), 7.59 (m, 2H), 8.48 (d, 1H, J=5.7 Hz), 10.21 (bs, 1H), 11.35 (bs, 1H).

HRMS (ESI) calcd for C19H19N6O2 [M+H]+ 363.1564. found 363.1577.

Example 20

2-[2-(3-Chloro-benzylamino)-pyrimidin-4-yl]-1-methyl-1,5,6,7-tetrahydro-pyrrolo[3,2-c]pyridin-4-one hydrochloride (Cpd. no 6)

[(I), R1, R2=H, R3=3-chloro-benzyl-amino, R4=Me]

The above compound was prepared according to Methods C and D as described below.

Step c (Method C)

2-[2-(3-Chloro-benzylamino)-pyrimidin-4-yl]-1-methyl-4-oxo-1,4,6,7-tetrahydro-pyrrolo[3,2-c]pyridine-5-carboxylic acid tert-butyl ester

[(II)w, R4=Me, R5=3-chloro-phenyl, Q=Boc]

Trifluoroacetic acid (0.740 g, 3.49 mmol) and sodium triacetoxyborohydride (0.740 g, 3.49 mmol) were added to a solution of 2-(2-amino-pyrimidin-4-yl)-1-methyl-4-oxo-1,4,6,7-tetrahydro-pyrrolo[3,2-c]pyridine-5-carboxylic acid tert-butyl ester (synthesised as reported in Example 9) (0.400 g, 1.16 mmol) in dry DMF (20.0 ml) and the reaction mixture was stirred at room temperature for 1 h. Sodium triacetoxyborohydride (0.740 g, 3.49 mmol) was then added and the mixture was stirred at room temperature for 24 h. In order to affect completion, a further of addition of 3-chloro-benzaldehyde (0.327 g, 2.33 mmol) and of sodium triacetoxyborohydride (0.740 g, 3.49 mmol) was done together with stirring at room temperature for 24 h. A solution of sodium hydroxide (1N, 40.0 ml) was added and the crude product, 2-[2-(3-Chloro-benzylamino)-pyrimidin-4-yl]-1-methyl-4-oxo-1,4,6,7-tetrahydro-pyrrolo[3,2-c]pyridine-5-carboxylic acid tert-butyl ester, precipitated as a yellow solid (0.530 g, 1.13 mmol, 97%).

HPLC (254 nm): Rt: 6.05 min.

¹H-NMR (401 MHz, DMSO-d6) δ=8.23 (d, J=5.2 Hz, 1H), 7.80-7.72 (m, 1H), 7.39-7.23 (m, 4H), 7.13 (s, 1H), 6.97 (d, J=5.2 Hz, 1H), 4.53 (d, J=6.1 Hz, 2H), 3.93 (m, 2H), 3.67 (br.s, 3H), 2.95-2.90 (m, 2H), 1.48-1.44 (m, 9H).

HRMS (ESI) calcd for C24H26ClN5O3 [M+H]+ 468.1797. found 468.1803.

Operating in an analogous way the following Boc-protected intermediate was prepared:

2-[2-(3-Hydroxy-benzylamino)-pyrimidin-4-yl]-1-methyl-4-oxo-1,4,6,7-tetrahydro-pyrrolo[3,2-c]pyridine-5-carboxylic acid tert-butyl ester

[(II)w, R4=Me, R5=3-Hydroxy-phenyl, Q=Boc]

HPLC (254 nm): Rt: 4.84 min.

¹H-NMR (401 MHz, DMSO-d6) δ=9.24 (s, 1H), 8.21 (d, J=5.2 Hz, 1H), 7.66 (br, s., 1H), 7.12 (s, 1H), 7.07 (t, J=8.0 Hz, 1H), 6.94 (d, J=5.2 Hz, 1H), 6.75-6.68 (m, 2H), 6.58 (dd, J=1.5, 7.9 Hz, 1H), 4.45 (d, J=6.3 Hz, 2H), 4.00-3.91 (m, 2H), 3.70 (br. s., 3H), 2.99-2.85 (m, 2H), 1.46 (s, 9H).

HRMS (ESI) calcd for C24H27N5O4 [M+H]+ 450.2136. found 450.2155.

Step a (Method D)

2-[2-(3-Chloro-benzylamino)-pyrimidin-4-yl]-1-methyl-1,5,6,7-tetrahydro-pyrrolo[3,2-c]pyridin-4-one hydrochloride

[(I), R1, R2=H, R3=3-chloro-benzyl-amino, R4=Me]

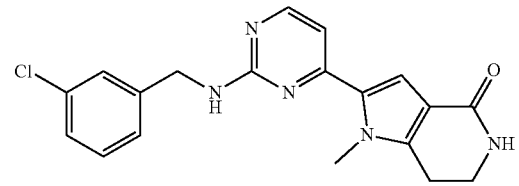 [SMILES: Cn1c(-c2ccnc(NCc3cccc(Cl)c3)n2)cc2c1CCNC2=O]

A suspension of 2-[2-(3-chloro-benzylamino)-pyrimidin-4-yl]-1-methyl-4-oxo-1,4,6,7-tetrahydro-pyrrolo[3,2-c]pyridine-5-carboxylic acid tert-butyl ester (0.510 g, 1.09 mmol) in 4M HCl in dioxane (20.0 ml) was stirred at room temperature for 3 h. The solvent was removed under vacuum affording the product as yellow solid (0.250 g, 0.618 mmol, 57%), after crystallization from methanol.

HPLC (254 nm): Rt: 4.31 min.

¹H-NMR (401 MHz, DMSO-d6) δ=8.49 (br. s., 1H), 8.19 (d, J=6.0 Hz, 1H), 7.41 (s, 1H), 7.39-7.14 (m, 5H), 7.23 (br. s., 1H), 4.64 (br. s., 2H), 3.71 (br. s., 3H), 3.38 (br. s., 2H), 2.91-2.82 (m, 2H).

HRMS (ESI) calcd for C19H18ClN5O [M+H]+ 368.1273. found 368.1277.

Operating in an analogous way the following compounds were synthesized:

2-{2-[(4-Bromo-thiophen-2-ylmethyl)-amino]-pyrimidin-4-yl}-1-methyl-1,5,6,7-tetrahydro-pyrrolo[3,2-c]pyridin-4-one hydrochloride (Cpd. no 7)

[(I), R1, R2=H, R3=4-bromo-thiophen-2-ylmethyl-amino, R4=Me]

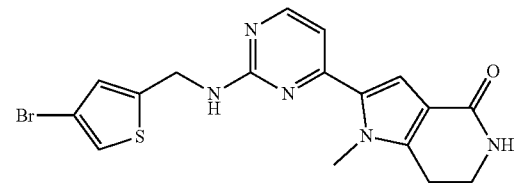 [SMILES: Cn1c(-c2ccnc(NCc3cc(Br)cs3)n2)cc2c1CCNC2=O]

HPLC (254 nm): Rt: 5.44 min.

¹H-NMR (401 MHz, DMSO-d₆) (selected signals) δ=8.45 (br. s., 1H), 8.20 (d, J=6.1 Hz, 1H), 7.51 (d, J=1.2 Hz, 1H), 7.40 (br, s., 1H), 7.22 (br. s., 2H), 7.06 (s, 1H), 4.75 (br. s., 2H), 3.87 (br. s., 3H), 2.88 (t, J=6.8 Hz, 2H).

HRMS (ESI) calcd for C17H17BrN5OS [M+H]+ 418.0332. found 418.0344.

2-[2-(3-Hydroxy-benzylamino)-pyrimidin-4-yl]-1-methyl-1,5,6,7-tetrahydro-pyrrolo[3,2-c]pyridin-4-one hydrochloride

[(I), R1, R2=H, R3=3-hydroxy-benzylamino, R4=Me]

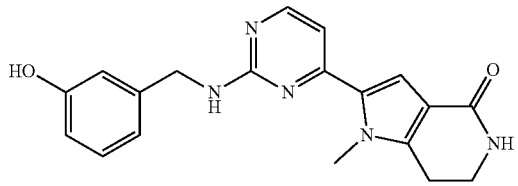 [SMILES: Cn1c(-c2ccnc(NCc3cccc(O)c3)n2)cc2c1CCNC2=O]

HPLC (254 nm): Rt: 4.4 min.
$^1$H-NMR (401 MHz, DMSO-$d_6$) (selected signals) δ=9.37 (br. s., 1H), 8.54 (br. s., 1H), 8.18 (d, J=5.4 Hz, 1H), 7.25 (br. s., 2H), 7.12 (t, J=7.7 Hz, 1H), 6.77-6.71 (m, 2H), 6.64 (dd, J=1.3, 8.1 Hz, 1H), 4.61-4.50 (m, 2H), 3.76 (br. s., 3H), 3.37 (m, 2H), 2.87 (t, J=6.8 Hz, 2H).
HRMS (ESI) calcd for C19H20N5O2 [M+H]+ 350.1612. found 350.1603.

Example 21

2-[2-(3-Chloro-phenylethynyl)-pyrimidin-4-yl]-1-methyl-1,5,6,7-tetrahydro-pyrrolo[3,2-c]pyridin-4-one (Cpd. no 8)

[(I), R1, R2=H, R3=3-chloro-phenylethynyl, R4=Me]

The above compound was prepared according to Methods C and D as described below.

Step d (Method C)

2-(2-Iodo-pyrimidin-4-yl)-4-oxo-1,4,6,7-tetrahydro-pyrrolo-[3,2-c]pyridine-5-carboxylic acid tert-butyl ester

[(24), R4=Me, Q=Boc]

Cesium iodide (1.29 g, 4.97 mmol), iodine (0.63 g, 2.48 mmol), copper iodide (0.283 g, 1.48 mmol) and amyl nitrite (0.87 g, 7.45 mmol) were added under argon to a solution of 2-(2-amino-pyrimidin-4-yl)-1-methyl-4-oxo-1,4,6,7-tetrahydro-pyrrolo[3,2-c]-pyridine-5-carboxylic acid tert-butyl ester (synthesised as reported in Example 9) (1.137 g, 3.30 mmol) in DME (30.0 ml). The reaction mixture was stirred at 80° C. for 4 h. DCM was added to the solution (20 ml) and the organic layer was washed with a saturated solution of NaHCO3 (1×30 ml), with a saturated solution of Na2S2O3 (1×30 ml), with purite water (1×30 ml) and it was dried over Na2SO4. The filtrate was purified by flash chromatography, over silica gel, using DCM/MeOH (9.8:0.2) as eluent, to afford 2-(2-iodo-pyrimidin-4-yl)-4-oxo-1,4,6,7-tetrahydro-pyrrolo[3,2-c]pyridine-5-carboxylic acid tert-butyl ester (0.240 g, 0.53 mmol, 16%) as a yellow solid.
HPLC (254 nm): Rt: 5.52 min.
$^1$H-NMR (401 MHz, DMSO-$d_6$) δ=8.41 (d, J=5.5 Hz, 1H), 7.91 (d, J=5.5 Hz, 1H), 7.43 (s, 1H), 3.99 (t, 2H), 3.89 (s, 3H), 2.99 (t, J=6.4 Hz, 2H), 1.48 (s, 9H).

HRMS (ESI) calcd for C17H19IN4O3 [M+H]+ 455.0575. found 455.0581.

Step e (Method C)

2-[2-(3-Chloro-phenylethynyl)-pyrimidin-4-yl]-1-methyl-4-oxo-1,4,6,7-tetrahydro-pyrrolo[3,2-c]pyridine-5-carboxylic acid tert-butyl ester

[(II)x, L3'=C≡C, R4=Me, R5=3-chlorophenyl, Q=Boc]

1-Chloro-3-ethynyl-benzene (0.018 g, 0.132 mmol), copper iodide (0.0012 g, 0.006 mmol) and PdCl2(PPh3)2 (0.0023 g, 0.003 mmol) were added under argon to a solution of 2-(2-iodo-pyrimidin-4-yl)-4-oxo-1,4,6,7-tetrahydro-pyrrolo[3,2-c]pyridine-5-carboxylic acid tert-butyl ester (0.030 g, 0.066 mmol) and triethylamine (0.170 ml) in dry ACN (0.500 ml). The reaction mixture was stirred at 80° C. for 3 h in argon atmosphere. The solvent was removed under vacuum and the crude residue was purified by flash chromatography, over silica gel, using DCM/MeOH (9.8:0.2) as eluent, to afford 2-[2-(3-chloro-phenylethynyl)-pyrimidin-4-yl]-1-methyl-4-oxo-1,4,6,7-tetra-hydro-pyrrolo[3,2-c]pyridine-5-carboxylic acid tert-butyl ester (0.018 g, 0.04 mmol, 60%).
HPLC (254 nm): Rt: 7.58 min.
$^1$H-NMR (401 MHz, DMSO-$d_6$) δ=8.72 (d, J=5.6 Hz, 1H), 7.87 (d, J=5.5 Hz, 1H), 7.76 (t, J=1.6 Hz, 1H), 7.65 (dt, J=1.3, 7.6 Hz, 1H), 7.62-7.58 (m, 1H), 7.52 (t, J=8.1 Hz, 1H), 7.41 (s, 1H), 4.00 (t, J=6.3 Hz, 2H), 3.97 (s, 3H), 3.00 (t, J=6.3 Hz, 2H), 1.48 (s, 9H).
HRMS (ESI) calcd for C25H23ClN4O3 [M+H]+ 463.1532. found 463.1536.

Step a (Method D)

2-[2-(3-Chloro-phenylethynyl)-pyrimidin-4-yl]-1-methyl-1,5,6,7-tetrahydro-pyrrolo[3,2-c]pyridin-4-one

[(I), R1, R2=H, R3=3-chloro-phenylethynyl, R4=Me]

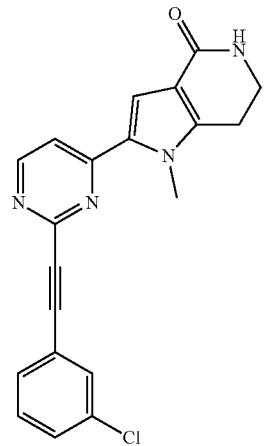 [SMILES: Cn1c(-c2ccnc(C#Cc3cccc(Cl)c3)n2)cc2c1CCNC2=O]

A suspension of 2-[2-(3-chloro-phenylethynyl)-pyrimidin-4-yl]-1-methyl-4-oxo-1,4,6,7-tetrahydro-pyrrolo[3,2-c]pyridine-5-carboxylic acid tert-butyl ester (0.018 g, 0.05 mmol) in 4M HCl in dioxane (3.0 ml) was stirred at room temperature for 2 h. The solvent was removed under vacuum and the crude was purified by column chromatography over silica gel, using DCM/MeOH (9.8:0.2) as eluent, affording 2-[2-(3-Chloro-phenylethynyl)-pyrimidin-4-yl]-1-methyl-1,5,6,7-tetrahydro-pyrrolo[3,2-c]pyridin-4-one as a yellow solid (0.007 g, 0.02 mmol, 50%).

HPLC (254 nm): Rt: 5.99 min.

$^1$H-NMR (401 MHz, DMSO-$d_6$) δ=8.67 (d, J=5.5 Hz, 1H), 7.83 (d, J=5.6 Hz, 1H), 7.75 (t, J=1.7 Hz, 1H), 7.65 (dt, J=1.3, 7.7 Hz, 1H), 7.60 (ddd, J=1.2, 2.2, 8.2 Hz, 1H), 7.51 (t, J=8.0 Hz, 1H), 7.31 (s, 1H), 7.18 (br. s., 1H), 3.98 (s, 3H), 3.44 (td, J=2.6, 6.8 Hz, 2H), 2.89 (t, J=6.8 Hz, 2H).

HRMS (ESI) calcd for C20H15ClN4O [M+H]+ 363.1007. found 363.1004.

Example 22

2-{2-[(E)-2-(3-Chloro-phenyl)-vinyl]-pyrimidin-4-yl}-1-methyl-1,5,6,7-tetrahydro-pyrrolo[3,2-c]pyridin-4-one (Cpd. no 9)

[(I), R1, R2=H, R3=(E)-2-(3-chloro-phenyl)-ethenyl, R4=Me]

The above compound was prepared according to Methods C and D as described below.

Step e (Method C)

2-{2-[(E)-2-(3-Chloro-phenyl)-vinyl]-pyrimidin-4-yl}-1-methyl-4-oxo-1,4,6,7-tetrahydro-pyrrolo[3,2-c]pyridine-5-carboxylic acid tert-butyl ester

[(II)x, L$_3$'=ethenyl, R4=Me, R5=3-chloro-phenyl, Q=Boc]

Cesium carbonate (0,143 g, 0.438 mmol), palladium tetrakis (0.051 g, 0.042 mmol) and 2-[(E)-2-(3-Chloro-phenyl)-vinyl]-4,4,5,5-tetramethyl-[1,3,2]dioxaborolane (0.116 g, 0.440 mmol) were added to a solution of 2-(2-Iodo-pyrimidin-4-yl)-1-methyl-4-oxo-1,4,6,7-tetrahydro-pyrrolo[3,2-c]pyridine-5-carboxylic acid tert-butyl ester (synthesised as reported in Example 9) (0.100 g, 0.22 mmol) in dioxane (5.0 ml) under argon atmosphere. Argon was bubbled for 5 minutes, the vial was closed and the reaction mixture was heated by microwave irradiation for 30 minute at 100° C. for two cycles. In order to affect completion, a refresh of the catalyst and the base and two more cycles at the microwaves were carried on. The solvent was removed under vacuum, the residue was taken into DCM (5.0 ml), which was washed with a saturated solution of NaHCO3 (1×5.0 ml), brine (1×5.0 ml), and it was dried over Na2SO4. The filtrate was evaporated to dryness to give the crude product, which was purified by flash chromatography, over silica gel, using DCM/MeOH (9.9:0.1) as eluent, to afford 2-{2-[(E)-2-(3-Chloro-phenyl)-vinyl]-pyrimidin-4-yl}-1-methyl-4-oxo-1,4,6,7-tetrahydro-pyrrolo[3,2-c]pyridine-5-carboxylic acid tert-butyl ester yellow solid (0.051 g, 0.110 mmol, 50%).

Step a (Method D)

2-{2-[(E)-2-(3-Chloro-phenyl)-vinyl]-pyrimidin-4-yl}-1-methyl-1,5,6,7-tetrahydro-pyrrolo[3,2-c]pyridin-4-one

[(I), R1, R2=H, R3=(E)-2-(3-chloro-phenyl)-ethenyl, R4=Me]

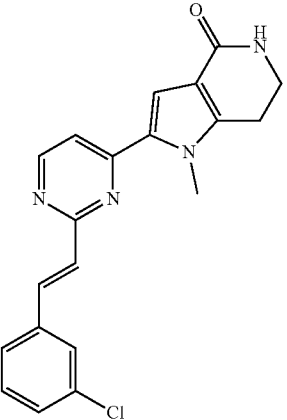 [SMILES: Cn1c(-c2ccnc(/C=C/c3cccc(Cl)c3)n2)cc2c1CCNC2=O]

A suspension of 2-{2-[(E)-2-(3-Chloro-phenyl)-vinyl]-pyrimidin-4-yl}-1-methyl-4-oxo-1,4,6,7-tetrahydro-pyrrolo[3,2-c]pyridine-5-carboxylic acid tert-butyl ester (0.050 g, 0.107 mmol) in 4M HCl/dioxane (2.0 ml) was stirred at room temperature for 1 h. The solvent was removed under vacuum and the product was purified by crystallisation from methanol, yielding 2-{2-[(E)-2-(3-Chloro-phenyl)-vinyl]-pyrimidin-4-yl}-1-methyl-1,5,6,7-tetrahydro-pyrrolo[3,2-c]pyridin-4-one as a yellow solid (0.015 g, 0.041 mmol, 38%).

HPLC (254 nm): Rt: 6.17 min.

$^1$H-NMR (401 MHz, DMSO-$d_6$) δ=8.66 (d, J=5.5 Hz, 1H), 7.91 (d, J=16.1 Hz, 1H), 7.87 (t, J=1.6 Hz, 1H), 7.73 (dt, J=1.4, 7.2 Hz, 1H), 7.68 (d, J=5.5 Hz, 1H), 7.46 (t, J=7.9 Hz, 1H), 7.43 (dt, J=1.7, 7.9 Hz, 1H), 7.35 (d, J=16.1 Hz, 1H), 7.28 (s, 1H), 7.17 (br. s., 1H), 4.06 (s, 3H), 3.46 (t, J=6.8 Hz, 2H), 2.91 (t, J=6.8 Hz, 2H).

HRMS (ESI) calcd for C20H17ClN4O [M+H]+ 365.1164. found 365.116.

The invention claimed is:

1. A method for treating a disease selected from the group consisting of melanoma, stomach cancer, liver cancer, colorectal cancer, pancreatic cancer, breast cancer, ovarian cancer, lung cancer, thyroid cancer, cervical cancer, myeloma and leukemia, which comprises administering to a mammal in need thereof an effective amount of a compound of formula (I):

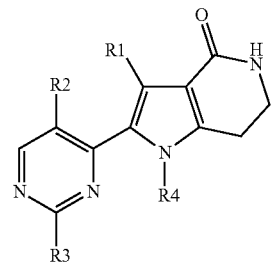

wherein:
R1 is hydrogen or R1', wherein R1' is

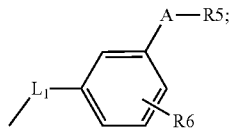

R2 is hydrogen or R2', wherein R2' is

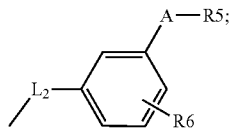

R3 is NH2 or R3', wherein R3' is L$_3$-R5,
wherein
L$_1$ is direct bond, CH$_2$, CH=CH, O, NH or N(CH$_3$);
L$_2$ is CH$_2$CH$_2$, CH=CH or C≡C;
L$_3$ is NHCO, NHCH$_2$, NHCONH, CH=CH or C≡C;
A is direct bond, O, OCH2, OCO, CON(Y), CON(Y)O, CON(Y)N(Y), CON(Y)SO$_2$, N(Y), N(Y)CO, N(Y)SO$_2$—, N(Y)CON(Y), N(Y)CSN(Y), N(Y)CON(Y)N(Y), N(Y)COO, N(Y)CON(Y)SO$_2$ or N(Y)SO$_2$N(Y);
Y is hydrogen or an optionally substituted straight or branched (C$_1$-C$_3$) alkyl;
R5 is hydrogen or an optionally substituted group selected from straight or branched (C$_1$-C$_8$) alkyl, (C$_2$-C$_8$) alkenyl, (C$_2$-C$_8$) alkynyl, (C$_3$-C$_8$) cycloalkyl, heterocyclyl, aryl and heteroaryl;
R6 is selected from hydrogen, halogen, trifluoromethyl, (C$_1$-C$_3$) alkyl and (C$_1$-C$_3$) alkoxy;
R4 is an optionally substituted group selected from straight or branched C$_1$-C$_6$ alkyl, C$_2$-C$_6$ alkenyl, C$_2$-C$_6$ alkynyl, C$_3$-C$_6$ cycloalkyl and heterocyclyl;
with the proviso that
only one of R1, R2 and R3 is respectively R1', R2' or R3' as defined above, and pharmaceutically acceptable salts.

2. The method according to claim 1 further comprising subjecting the mammal in need thereof to a radiation therapy or chemotherapy regimen in combination with at least one cytostatic or cytotoxic agent.

3. The method according to claim 1 wherein the mammal in need thereof is a human.

4. An method for inhibiting BRaf protein activity which comprises contacting the said protein with an effective amount of a compound of formula (I) as defined in claim 1.

5. The method according to claim 1 which provides tumor angiogenesis and metastasis inhibition.

\* \* \* \* \*